(12) United States Patent
Uesaka et al.

(10) Patent No.: US 9,714,257 B2
(45) Date of Patent: Jul. 25, 2017

(54) THERAPEUTIC AGENT FOR MOTOR DISORDERS

(71) Applicant: KYOWA HAKKO KIRIN CO., LTD., Chiyoda-ku, Tokyo (JP)

(72) Inventors: Noriaki Uesaka, Shizuoka (JP); Takashi Sawada, Shizuoka (JP); Tomoyuki Kanda, Shizuoka (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/691,982

(22) Filed: Apr. 21, 2015

(65) Prior Publication Data
US 2015/0225417 A1   Aug. 13, 2015

Related U.S. Application Data

(63) Continuation of application No. 13/266,152, filed as application No. PCT/JP2010/057563 on Apr. 28, 2010, now abandoned.

(30) Foreign Application Priority Data

Apr. 28, 2009   (JP) .................................. 2009/109434

(51) Int. Cl.
| | |
|---|---|
| A61K 31/4439 | (2006.01) |
| A61K 31/506 | (2006.01) |
| A61K 31/427 | (2006.01) |
| A61K 31/4709 | (2006.01) |
| A61K 31/4355 | (2006.01) |
| A61K 31/435 | (2006.01) |
| A61K 31/4365 | (2006.01) |
| A61K 31/198 | (2006.01) |
| C07D 495/04 | (2006.01) |
| A61K 31/436 | (2006.01) |
| A61K 31/5377 | (2006.01) |
| C07D 417/14 | (2006.01) |
| C07D 491/048 | (2006.01) |
| C07D 491/052 | (2006.01) |

(52) U.S. Cl.
CPC .......... *C07D 495/04* (2013.01); *A61K 31/198* (2013.01); *A61K 31/427* (2013.01); *A61K 31/435* (2013.01); *A61K 31/436* (2013.01); *A61K 31/4355* (2013.01); *A61K 31/4365* (2013.01); *A61K 31/4439* (2013.01); *A61K 31/4709* (2013.01); *A61K 31/506* (2013.01); *A61K 31/5377* (2013.01); *C07D 417/14* (2013.01); *C07D 491/048* (2013.01); *C07D 491/052* (2013.01)

(58) Field of Classification Search
None
See application file for complete search history.

(56) References Cited

U.S. PATENT DOCUMENTS

| | | | |
|---|---|---|---|
| 7,713,985 B2 | 5/2010 | Clasby et al. | |
| 7,718,808 B2 | 5/2010 | Nakajima et al. | |
| 7,727,994 B2 | 6/2010 | Kase et al. | |
| 7,851,478 B2 | 12/2010 | Kadowaki et al. | |
| 7,880,013 B2 | 2/2011 | Nakajima et al. | |
| 7,910,613 B2 | 3/2011 | Larsen et al. | |
| 7,928,098 B2 | 4/2011 | Uesaka et al. | |
| 8,420,827 B2 | 4/2013 | Nakajima et al. | |
| 2007/0105919 A1 | 5/2007 | Nakajima et al. | |
| 2009/0005568 A1 | 1/2009 | Cole et al. | |
| 2010/0280023 A1 | 11/2010 | Sugawara et al. | |

(Continued)

FOREIGN PATENT DOCUMENTS

| | | |
|---|---|---|
| EP | 1 700 856 | 9/2006 |
| EP | 1 894 930 | 3/2008 |

(Continued)

OTHER PUBLICATIONS

Brown et al., "Recent advances in the treatment of L-DOPA-induced dyskinesia"; IDrugs, vol. 5, No. 5 (2002) 454-68.
Bruns et al., "Characterization of the A2 Adenosine Receptor Labeled by [3H]NECA in Rat Striatal Membranes", Mol. Pharmacol. vol. 29 (1986) 331-46.
Bruns, et al., "Binding of the A1-selective adenosine antagonist 8-cyclopetyl-1,3-dipropylxanthine to rat brain membranes", Arch. Pharmacol., vol. 335, No. 1 (1987) 59-63.
Burns, et al., "A primate model of parkinsonism: Selective destruction of dopaminergic neurons in the pars compacta of the substantia nigra by N-methyl-4-phenyl-1,2,3,6-tetrahydropyridine", Proc. Natl. Acad. Sci., vol. 80 (1983) 4546-50.

(Continued)

*Primary Examiner* — Jeffrey S Lundgren
*Assistant Examiner* — Michael Schmitt
(74) *Attorney, Agent, or Firm* — Fitzpatrick Cella Harper and Scinto

(57) ABSTRACT

Provided are an agent for the treatment and/or prophylaxis of a movement disorder, the agent for the treatment and/or prophylaxis wherein the movement disorder is extrapyramidal syndrome, the agent for the treatment and/or prophylaxis wherein the movement disorder is bradykinesia, gait disturbance, dystonia, dyskinesia or tardive dyskinesia, the agent for the treatment and/or prophylaxis wherein the movement disorder is a side effect of L-DOPA and/or dopamine agonist therapy, and the like, each containing a thiazole derivative represented by the formula (I) wherein $R^1$ represents aryl and the like, and $R^2$ represents pyridyl or the like, or a pharmaceutically acceptable salt thereof as an active ingredient.

(I)

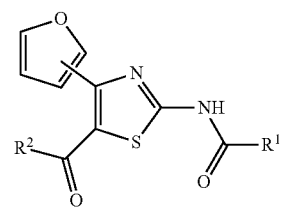

9 Claims, 1 Drawing Sheet

(56) References Cited

U.S. PATENT DOCUMENTS

2011/0105465 A1  5/2011  Ouchi et al.
2011/0183992 A1  7/2011  Ikeda et al.

FOREIGN PATENT DOCUMENTS

| EP | 1 902 716 | 3/2008 |
|---|---|---|
| JP | 2005-523898 | 8/2005 |
| WO | 03/063876 | 8/2003 |
| WO | 2005/063743 | 7/2005 |
| WO | 2006/032273 | 3/2006 |
| WO | 2007/015528 | 2/2007 |
| WO | 2007/022415 | 2/2007 |
| WO | 2008/002596 | 1/2008 |
| WO | 2009/145289 | 12/2009 |

OTHER PUBLICATIONS

Ferré, et al., "Adenosine A2A receptors in ventral striatum, hypothalamus and nociceptive circuitry: Implications for drug addiction, sleep and pain", Progress in Neurobiology, vol. 83 (2007) 332-47.
Gjerstad, et al., "Excessive daytime sleepiness in Parkinson disease. Is it the drugs or the disease?", Neurology, vol. 67 (2006) 853-58.
Goetz, et al., "Movement Disorders Society-Sponsored Revision of the Unified Parkinson's Disease Rating Scale (MDS-UPDRS): Process, Format and Clinimetric Testing Plan", Movement Disorders, vol. 22, No. 1 (2006) 41-7.
Golembiowska, et al., "Effect of adenosine A2A receptor antagonist 8-(3-chlorostyryl)caffeine on L-DOPA biotransformation in rat striatum", Brain Research, vol. 998, No. 2 (2004) 208-17.
Grondin et al., "Antiparkinsonian effect of a new selective adenosine A2A receptor antagonist in MPTP-treated monkeys", Neurology, vol. 52, No. 8 (1999) 1673-77.
Hauser, et al., "Study of Istradefylline in Patients with Parkinson's Disease on Levodopa with Motor Fluctuations", Movement Disorders, vol. 23, No. 15 (2008) 2177-185.
Huang, et al., "Adenosine A2A, but not A1, receptors mediate the arousal effect of caffeine", Nature Neuroscience, vol. 8, No. 7 (2005) 858-59.
Jacobson, et al., "Adenosine receptor as therapeutic targets", Nature Reviews., vol. 5 (2006) 247-64.
Jenner, et al., "Adenosine, adenosine A2A antagonists, and Parkinson's disease", Parkinsonism and Related Disorders, vol. 15 (2009) 406-13.
Kanda et al., "Adenosine A2A Antagonist: A Novel Antiparkinsonian Agent that Does Not Provoke Dyskinesia in Parkinsonian Monkeys", Ann. Neurol., vol. 43, No. 4 (1998) 507-13.
Kanda et al., "Combined Use of the Adenosine A2A Antagonist KW-6002 with L-DOPA or with Selective D1 or D2 Dopamine Agonists Increases Antiparkinsonian Activity but Not Dyskinesia in MPTP-Treated Monkeys", Exp. Neurol., vol. 162 (2000) 321-27.
LeWitt, et al., "Adenosine A2A Receptor Antagonist Instradefylline (KW-6002) Reduces "Off" Time in Parkinson's Disease: A Double-Blind, Randomized, Multicenter Clinical Trial (6002-US-005)", Annals of Neurology, vol. 63, No. 3 (2008) 295-302.
Mardsen, et al., "Fluctuations of disability in Parkinson's disease—clinical aspects", Neurology 2, Movement Disorders, Butterworths International Medical Reviews (1982) 96-122.
Matsubara, et al., "The Treatment of Parkinson's disease—adenosine A2A receptor antagonists", Jpn. J. Clin. Med., vol. 60, No. 1 (2002) 112-16.
Mori, et al., "Adenosine A2A kikkoyaku no KoParkinson's disease Sayo", Folia Pharmacologica Japonica, vol. 129, No. 5 (2007) 390-91.
Nomoto, et al., The Dopamined D2 Agonist LY 141865, but not the D1 Agonist SKF 38393, Reverses Parkinsonism induced by 1-methyl-4-phenyl-1,2,3,6-tetrahydropyridine (MPTP) in the Common Marmoset, Neurosci. Lett., vol. 57 (1985) 37-41.
Nonaka, et al., "KW-3902, a selective high affinity antagonist for adenosine A1 receptors", Brit. J. Pharmacol., vol. 117, No. 8 (1996) 1645-52.
Olanow, et al., "An algorithm (decision tree) for the management of Parkinson's disease (2001): Treatment Guidelines", Neurology, vol. 56 Suppl. 5. (2001) S1-S88.
Parkinson Study Group, "Impact of Deprenyl and Tocopherol Treatment on Parkinson's Disease in DATATOP Patients Requiring Levodopa", Ann. Neurol., vol. 39, No. 1 (1996) 37-45.
Rascol et al., "A Five Year Study of the Incidence of Dyskinesia in Patients with Early Parkinson's Disease Who Were Treated with Ropinirole or Levodopa", N. Eng. J. Med., vol. 342, No. 20 (2000) 1484-91.
Rose, et al., "The novel adenosine A2a antagonist ST1535 potentiates the effects of a threshold dose of L-dopa in unilaterally 6-OHDA-lesioned rats", Brain Research, vol. 1133, No. 16 (2007) 110-14.
Rose, et al., "The novel adenosine A2a receptor antagonist ST1535 potentiates the effects of a threshold dose of L-DOPA in MPTP treated common marmosets", European Journal of Pharmacology, vol. 546, No. 1-3 (2006) 82-87.
Schapira, et al., "Novel pharmacological targets for treatment of Parkinson's disease", Nature Reviews, vol. 5 (2006) 845-54.
Simola, et al., "Adenosine A2A Receptor Antagonists and Parkinson's Disease: State of the Art and Future Directions", Curr. Pharm. Design, vol. 14 (2008) 1475-89.
Suzuki, et al., "Effects of the Adenosine A1-Receptor Antagonist on Defecation, Small Intestinal Propulsion and Gastric Emptying in Rats", Jpn. J. Pharmacol., vol. 68 (1995) 119-23.
Varani, et al., "Pharmacological and biochemical characterization of purified A2a adenosine receptors in human platelet membranes by [3H]-CGS 21680 binding", Brit. J. Pharmacol., vol. 117 (1996) 1693-1701.
Wardas, et al., "SCH 58261, an A2A Adenosine Receptor Antagonist, Counteracts Parkinsonian-Like Muscle Rigidity in Rats", Synapse, vol. 41, No. 2 (2001) 160-71.
Winne, et al., "Closed rat jejunal segment in situ: role of pre-epithelial diffusion resistance (unstirred layer) in the absorption process and model analysis", Arch Pharmacol., vol. 335, No. 2 (1987) 204-15.

THERAPEUTIC AGENT FOR MOTOR DISORDERS

This application is a continuation of application Ser. No. 13/266,152 filed Dec. 21, 2011, which in turn is a 371 of PCT Application No. PCT/JP2010/057563 filed Apr. 28, 2010, which claims benefit of Japanese Application No. 109434/2009 filed Apr. 28, 2009. The subject matter of each of these applications is hereby incorporated by reference herein.

TECHNICAL FIELD

The present invention relates to an agent for the treatment and/or prophylaxis of a movement disorder, an agent for the treatment and/or prophylaxis of Parkinson's disease and the like.

BACKGROUND ART

Parkinson's disease is a brain disease characterized by tremor, bradykinesia, difficulty in gait and coordinated movement and the like. This disease is associated with damage of a part of brain which governs muscle movements. Generally, the first symptom of Parkinson's disease is a limb tremor (shaking or trembling) particularly when the body is at rest. Tremor often begins in the hemibody, and frequently occurs in one of the hands. Other common symptoms include slow movement (bradykinesia), an inability to move (akinesia), a rigidity of trunk and limbs, a shuffling gait, and a stooped posture and the like. Patients with Parkinson's disease are poor in facial expression, and tend to speak in a soft voice. Parkinson's disease can cause secondary symptoms such as depression, anxiety, personality change, cognitive impairment, dementia, sleep disturbances, speech impairments or sexual dysfunction. The drug therapy of Parkinson's disease currently employed clinically mainly controls the parkinsonian symptoms by controlling the imbalance among neurotransmitters. Early stage patients of Parkinson's disease mostly respond well to a symptomatic therapy by a dopamine replacement therapy; however, the disability increases with progression of the disease.

Although currently available medications for Parkinson's disease generally provide adequate symptomatic control for several years, however, many patients develop motor fluctuations and dyskinesias that compromise clinical response (The New England Journal of Medicine (N. Eng. J. Med.), vol. 342, p. 1484 (2000) and the like).

Although more than thirty years have passed since discovering L-DOPA, it is still the best agent for treatment of Parkinson's disease. In the early stages of Parkinson's disease, patients usually enjoy a good response to L-DOPA. As the disease progresses, however, L-DOPA tends to become less helpful. This is not due to the loss of efficacy of L-DOPA, but rather, for example, to development of motor complications such as end-of-dose deterioration or adverse fluctuation in motor response including "wearing-off phenomenon", "on-off fluctuations", and dyskinesias.

The "on-off fluctuations" is an event wherein therapeutic benefit of a medication ("on" state, during which the patients are relatively free from the symptoms of Parkinson's disease) is suddenly and unacceptably lost, and the parkinsonian state ("off" state) appears. Such condition occurs when patients with Parkinson's disease are under L-DOPA therapy and exposed to L-DOPA in an amount sufficient to express the efficacy. However, even if such symptoms are expressed, the treatment effect may recover all of a sudden.

The "wearing-off phenomenon" is a phenomenon wherein the duration of L-DOPA action is decreased in patients with Parkinson's disease, even though they are under L-DOPA therapy and exposed to L-DOPA in an amount sufficient to express the efficacy. The phenomenon is characterized by the gradual reappearance of the "off" state, and shortening of the "on" state. That is, it refers to a phenomenon where the duration of the treatment effect of L-DOPA gradually becomes shorter (duration of the treatment effect after administration of L-DOPA becomes shorter), which is remarkably seen in an advanced stage of the disease in patients with Parkinson's disease under L-DOPA therapy.

Dyskinesia can be broadly classified into chorea-like symptoms (hyperactive, purposeless dance-like movement) and dystonia (sustained, abnormal muscle contraction). In 1974, Duvoisin first focused on these abnormal involuntary movements, and found that half or more of patients with Parkinson's disease develop dyskinesia within 6 months of the treatment. With increasing period of treatment, both the frequency and severity of dyskinesia increase. In a study of the potential benefits of possible neuroprotectants in Parkinson's disease-DATATOP trial-, L-DOPA induced dyskinesia was observed in 20-30% of patients who received L-DOPA treatment for a mean of 20.5 months. Ultimately, most L-DOPA treated patients experienced dyskinesia; up to 80% of the patients developed dyskinesia within 5 years. (Annals of Neurology (Ann. Neurol.), vol. 39, p. 37 (1966); The New England Journal of Medicine (N. Eng. J. Med.), vol. 342, p. 1484 (2000)). Most dyskinesias occur when L-DOPA or other dopamine receptor agonists have a concentration in the brain that is sufficient to hypersensitive dopamine receptors in the putamen (peak dose dyskinesia). However, dyskinesia also occurs when the dopamine concentration is low (off-dystonia), or in a stage wherein the concentration of dopamine rises or falls (biphasic dyskinesia).

On the other hand, it is known that adenosine is widely distributed in the whole body, and exhibits a variety of physiological actions on the central nervous system, the cardiac muscle, the kidneys, the smooth muscle, and the like through its receptors (see non-patent document 1), and that an antagonist thereof is useful for the treatment and/or prophylaxis of various diseases.

For example, adenosine $A_1$ antagonists are known to facilitate defecation (The Japanese Journal of Pharmacology (Jpn. J. Pharmacol.), Vol. 68, p. 119 (1995)). Further, the adenosine $A_{2A}$ receptors are known to be involved particularly in the central nervous system, and the antagonists of the adenosine $A_{2A}$ receptors are known to be useful as, for example, therapeutic drugs for Parkinson's disease etc. (see non-patent document 2), therapeutic drugs for sleep disturbance (see Nature Neuroscience, p. 858 (2005); patent document 1) and the like. There are many reports concerning the relationship between adenosine receptors and Parkinson's disease (see, for example, non-patent documents 3 and 4).

In addition, (i) a method of reducing or suppressing side effects of L-DOPA therapy, (ii) a treatment method by reducing the dose of L-DOPA in L-DOPA therapy, (iii) a method of prolonging the duration of effectiveness of the treatment of Parkinson's disease in L-DOPA therapy, (iv) a method of treating a movement disorder and the like, each using an adenosine $A_{2A}$ receptor antagonist, are known (see patent document 2). To be specific, it is known that movement disorders such as tremor, bradykinesia, gait disturbance, akinesia and the like can be suppressed by administering an adenosine $A_{2A}$ receptor antagonist represented by the formula (A) and L-DOPA to patients with Parkinson's disease, and adenosine $A_{2A}$ receptor antagonist represented by the formula (A) suppresses dyskinesia developed by administration of L-DOPA, and the like. Furthermore, it is known that an adenosine $A_{2A}$ receptor antagonist represented by the formula (A) shows an antiparkinson effect in MPTP-treated common marmoset (see non-patent document 5), does not provoke dyskinesia (see non-patent document 6), and does not provoke dyskinesia but potentiates an antiparkinson effect when used in combination with L-DOPA and/or a dopamine agonist (see non-patent document 7).

(A)

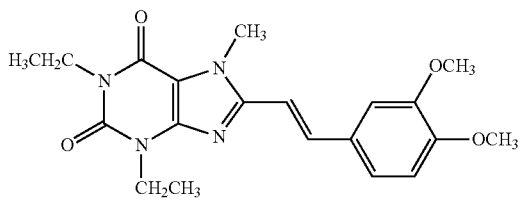

On the other hand, for example, compounds represented by the formulas (IA), (IB), (IC), (ID) and the like are known to have affinity to adenosine $A_{2A}$ receptors and have a therapeutic effect for Parkinson's disease (see patent document 3). Moreover, thiazole derivatives having an adenosine $A_{2A}$ receptor antagonistic activity are known (see patent document 4). It is also known that these compounds are useful as an agent for the treatment and/or prophylaxis of sleep disturbance (see patent document 1), an agent for the treatment and/or prophylaxis of migraine (see patent document 5), an analgesic tolerance inhibitor (see patent document 6) and the like.

(IA)

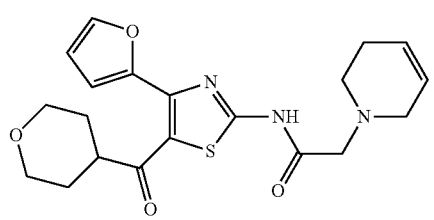

(IB)

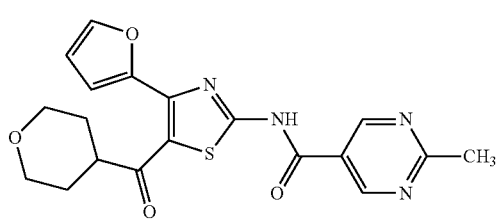

(IC)

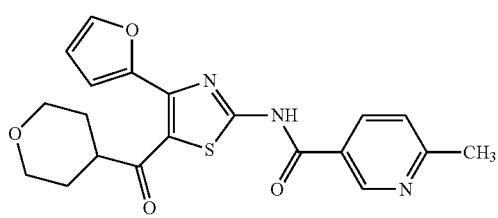

(ID)

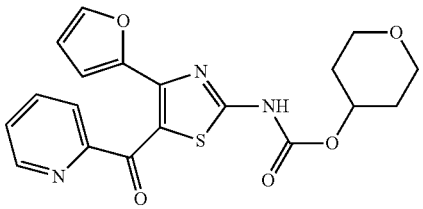

PRIOR DOCUMENT LIST

Patent Documents

[patent document 1] WO2007/015528
[patent document 2] WO2003/063876
[patent document 3] WO2005/063743
[patent document 4] WO2006/137527
[patent document 5] WO2010/010908
[patent document 6] WO2009/145289

Non-Patent Documents

[non-patent document 1] Nature Reviews Drug Discovery, 2006, vol. 5, p. 247
[non-patent document 2] Progress in Neurobiology, 2007, vol. 83, p. 332
[non-patent document 3] Nature Reviews Drug Discovery, 2006, vol. 5, p. 845
[non-patent document 4] Current Pharmaceutical Design, 2008, vol. 14, p. 1475
[non-patent document 5] Neurology, 1999, vol. 52, p. 1673
[non-patent document 6] Annals of Neurology, 1998, vol. 43, p. 507
[non-patent document 7] EXPERIMENTAL NEUROLOGY, 1999, vol. 162, p. 321

SUMMARY OF THE INVENTION

Problems to be Solved by the Invention

An object of the present invention is to provide an agent for the treatment and/or prophylaxis of a movement disorder such as a motor control disorder (e.g., extrapyramidal syndrome or the like), hypermobility (e.g., dystonia, dyskinesia, tardive dyskinesia, tremor, chorea, ballism, akathisia, athetosis, bradykinesia, gait disturbance, freezing, rigidity, postural instability, myoclonus, tics or Tourette syndrome, postural reflex disorder or the like), side effects of L-DOPA and/or dopamine agonist therapy (e.g., wearing-off phenomenon, dyskinesia or the like), or the like, an agent for the treatment and/or prophylaxis of Parkinson's disease and the like. Another object is to provide a thiazole derivative or a pharmaceutically acceptable salt thereof having a selective adenosine $A_{2A}$ antagonist, and useful as the above-mentioned agent for the treatment and/or prevention, or a pharmaceutically acceptable salt thereof.

Means of Solving the Problems

The present invention relates to the following (1)-(100).
(1) An agent for the treatment and/or prophylaxis of a movement disorder, comprising a thiazole derivative represented by the formula (I)

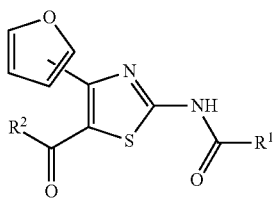
(I)

wherein R¹ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof as an active ingredient.

(2) The agent of (1), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.

(3) The agent of (1), wherein R¹ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(4) The agent of any one of (1)-(3), wherein R² is pyridyl.

(5) The agent of any one of (1)-(3), wherein R² is tetrahydropyranyl.

(6) The agent of (1), wherein the thiazole derivative represented by the formula (I) is a compound represented by any one of the following formulas (IA)-(IAA).

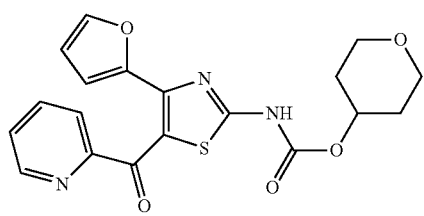
(ID)

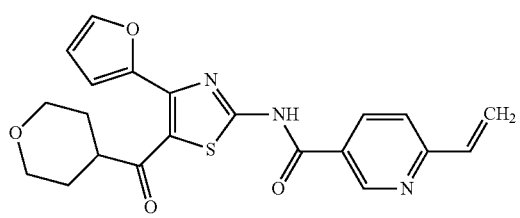
(IE)

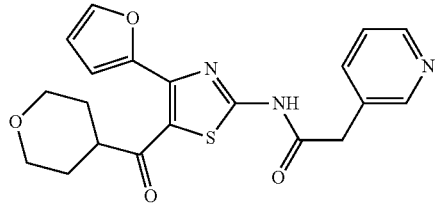
(IF)

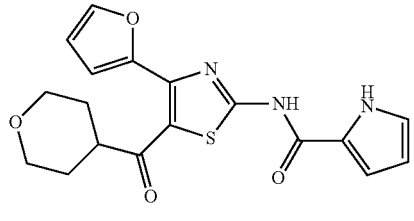
(IG)

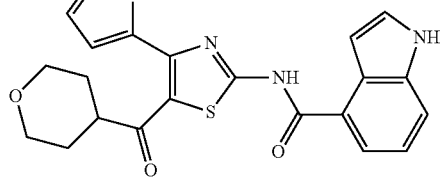
(IH)

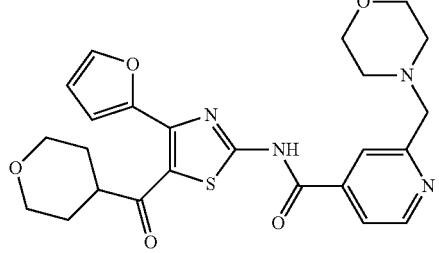
(II)

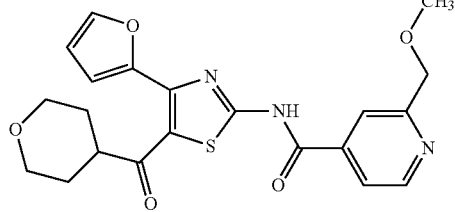
(IJ)

(7) The agent of any one of (1)-(6), wherein the movement disorder is an extrapyramidal syndrome.

(8) The agent of any one of (1)-(6), wherein the movement disorder is bradykinesia, gait disturbance, dystonia, dyskinesia or tardive dyskinesia.

(9) The agent of any one of (1)-(6), wherein the movement disorder is a side effect of L-DOPA and/or dopamine agonist therapy.

(10) The agent of (9), wherein the side effect is a motor complication.

(11) The agent of (10), wherein the motor complication is wearing-off phenomenon.

(12) The agent of (10), wherein the motor complication is on-off fluctuation.

(13) The agent of (10), wherein the motor complication is dyskinesia.

(14) The agent of any one of (1)-(13), wherein the movement disorder is that developed in an advanced stage of Parkinson's disease.

(15) A pharmaceutical composition comprising (a) a thiazole derivative represented by the formula (I)

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and $R^2$ represents pyridyl or tetrahydropyranyl, or a pharmaceutically acceptable salt thereof, and (b) L-DOPA and/or a dopamine agonist.

(16) The pharmaceutical composition of (15), wherein $R^1$ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and $R^2$ is pyridyl or tetrahydropyranyl.

(17) The pharmaceutical composition of (15), wherein $R^1$ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(18) The pharmaceutical composition of any one of (15)-(17), wherein $R^2$ is pyridyl.

(19) The pharmaceutical composition of any one of (15)-(17), wherein $R^2$ is tetrahydropyranyl.

(20) The pharmaceutical composition of (15), wherein the thiazole derivative represented by the formula (I) is a compound represented by any one of the following formulas (IA)-(IAA).

(IC)
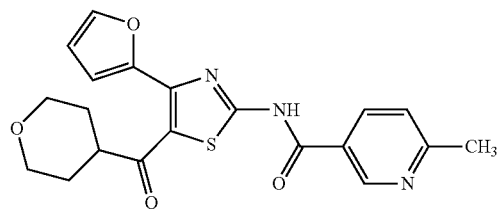
(ID)
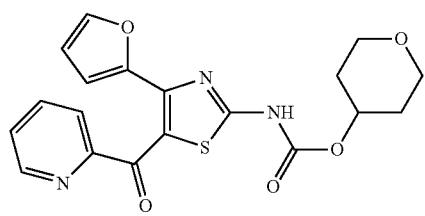
(IE)
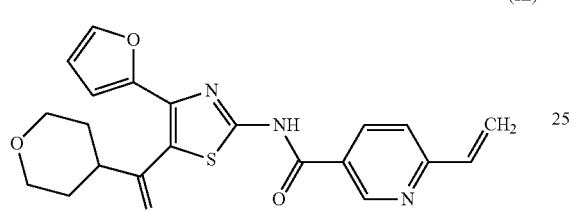
(IF)
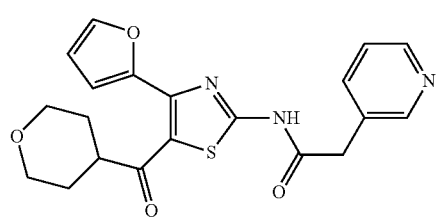
(IG)
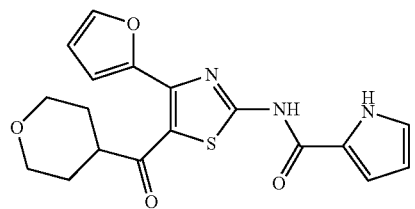
(IH)
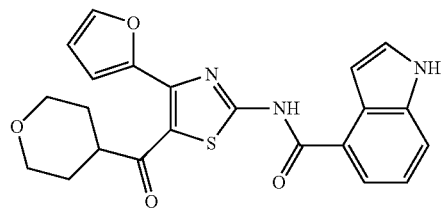
(II)
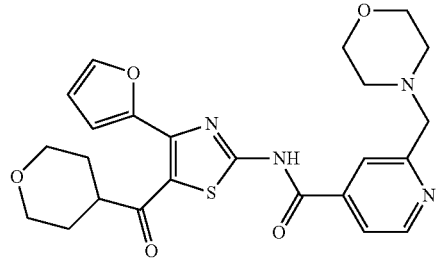
(IJ)
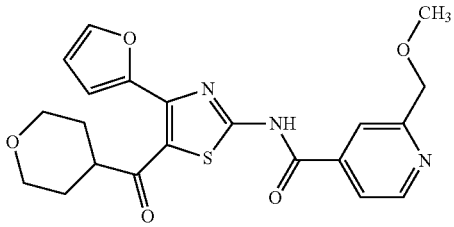
(IK)
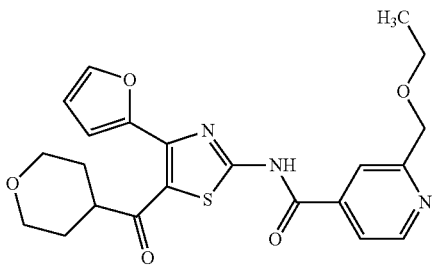
(IL)
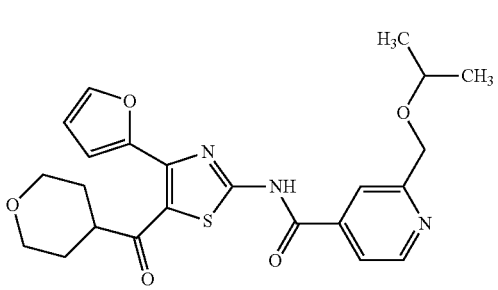
(IM)
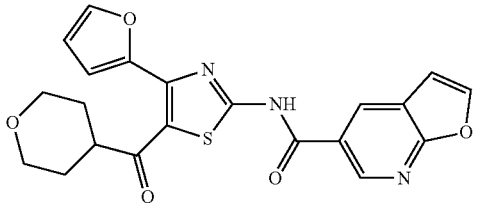
(IN)
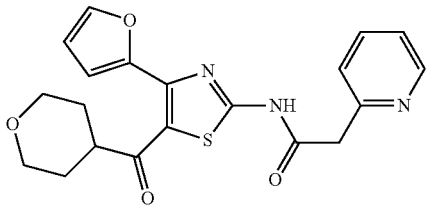
(IO)
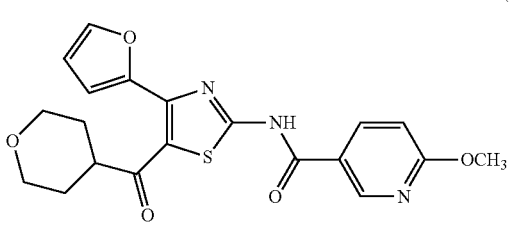

(IP)
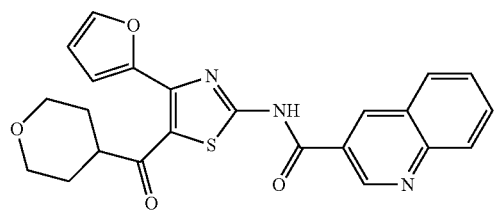

(IQ)
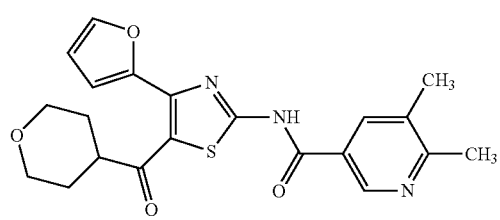

(IR)
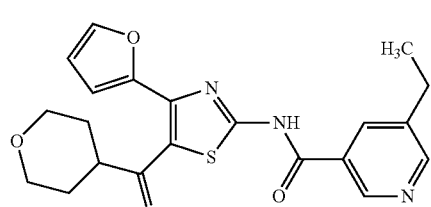

(IS)
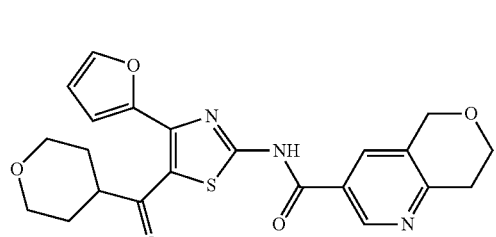

(IT)
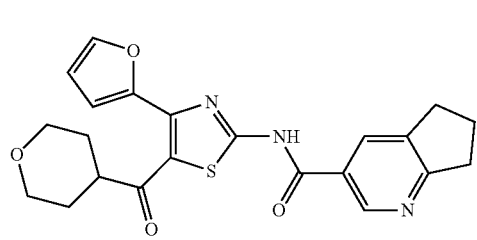

(IU)
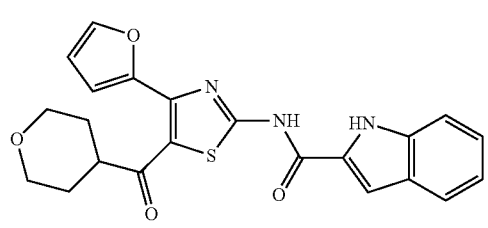

(IV)
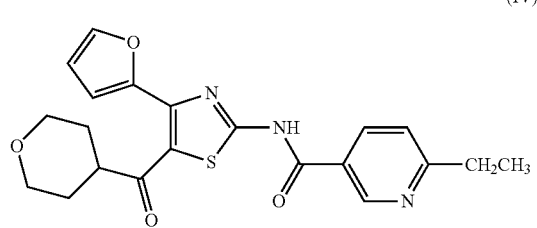

(IW)
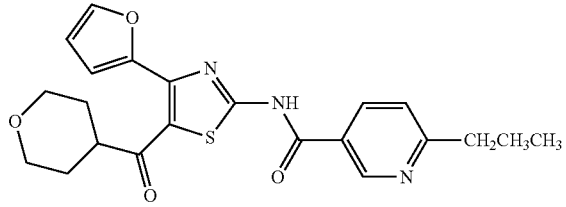

(IX)
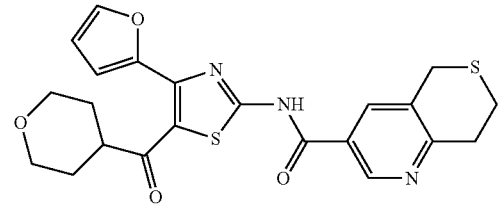

(IY)
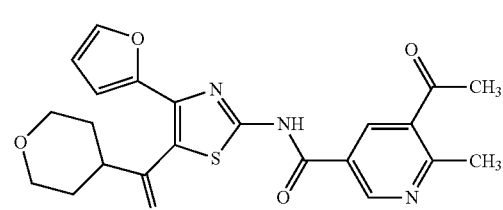

(IZ)
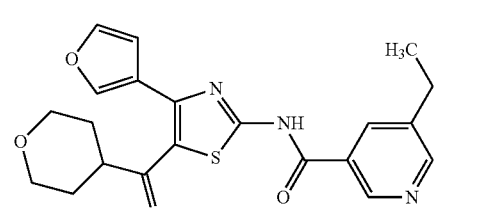

(IAA)
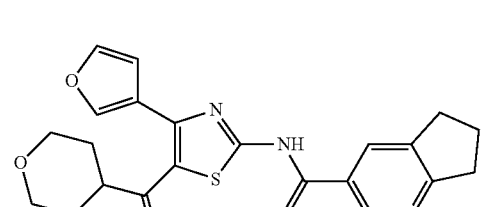

(21) An agent for the treatment and/or prophylaxis of Parkinson's disease, comprising (a) a thiazole derivative represented by the formula (I)

(I)
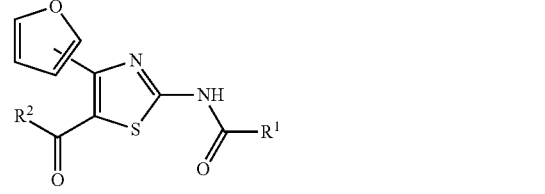

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof, and (b) L-DOPA and/or a dopamine agonist in combination.

(22) The agent of (21), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.

(23) The agent of (21), wherein R¹ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(24) The agent of any one of (21)-(23), wherein R² is pyridyl.

(25) The agent of any one of (21)-(23), wherein R² is tetrahydropyranyl.

(26) The agent of (21), wherein the thiazole derivative represented by the formula (I) is a compound represented by any one of the following formulas (IA)-(IAA).

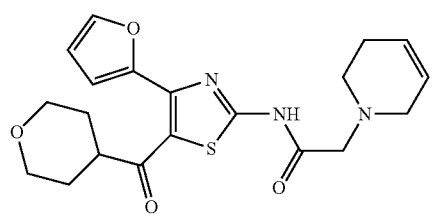
(IA)

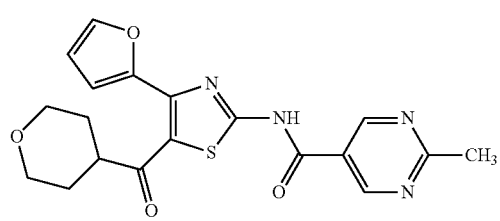
(IB)

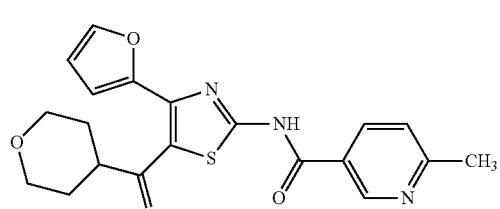
(IC)

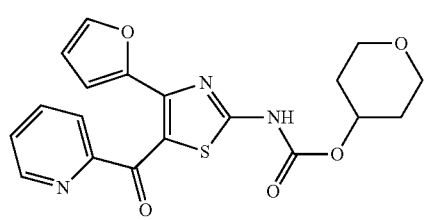
(ID)

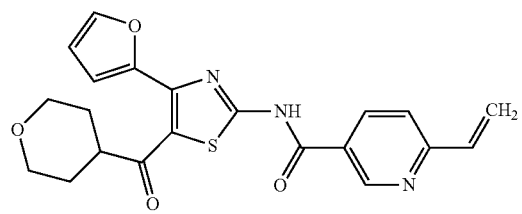
(IE)

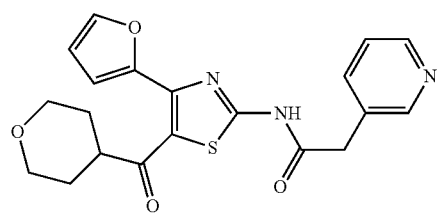
(IF)

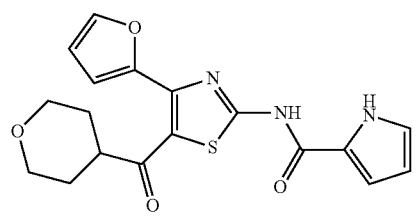
(IG)

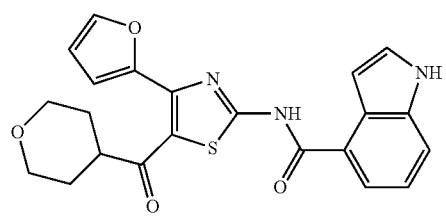
(IH)

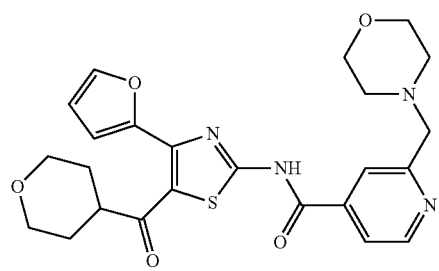
(II)

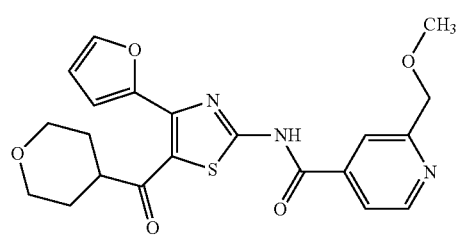
(IJ)

-continued (IK)
(IL)
(IM)
(IN)
(IO)
(IP)
(IQ)
(IR)
(IS)
(IT)
(IU)
(IV)
(IW)

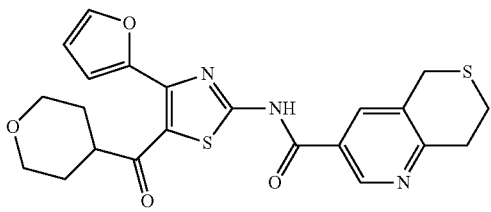
(IX)

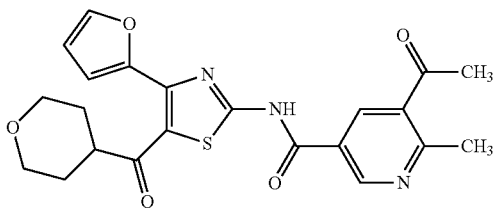
(IY)

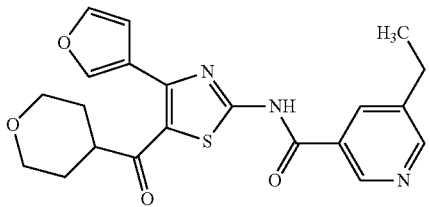
(IZ)

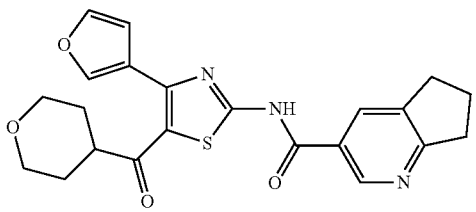
(IAA)

(27) The agent of any one of (21)-(26), for administering (a) and (b) simultaneously or separately at an interval.
(28) The agent of any one of (21)-(27), wherein the Parkinson's disease is that in an advanced stage.
(29) A kit comprising (a) a first component comprising a thiazole derivative represented by the formula (I)

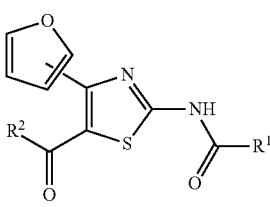
(I)

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and $R^2$ represents pyridyl or tetrahydropyranyl, or a pharmaceutically acceptable salt thereof, and (b) a second component comprising L-DOPA and/or a dopamine agonist.
(30) The kit of (29), wherein $R^1$ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and $R^2$ is pyridyl or tetrahydropyranyl.
(31) The kit of (29), wherein $R^1$ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.
(32) The kit of any one of (29)-(31), wherein $R^2$ is pyridyl.
(33) The kit of any one of (29)-(31), wherein $R^2$ is tetrahydropyranyl.
(34) The kit of (29), wherein the thiazole derivative represented by the formula (I) is a compound represented by any one of the following formulas (IA)-(IAA).

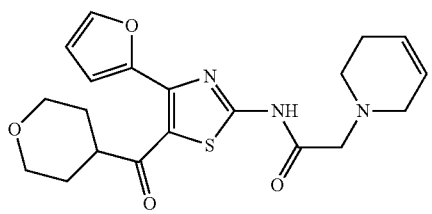
(IA)

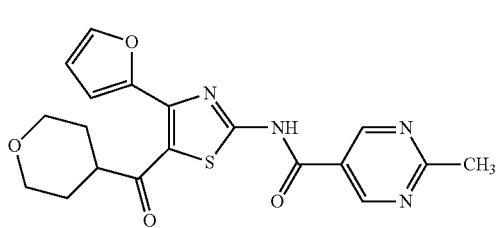
(IB)

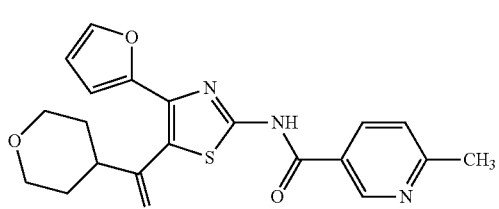
(IC)

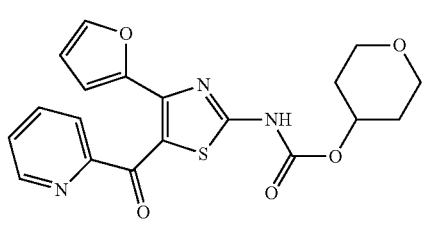
(ID)

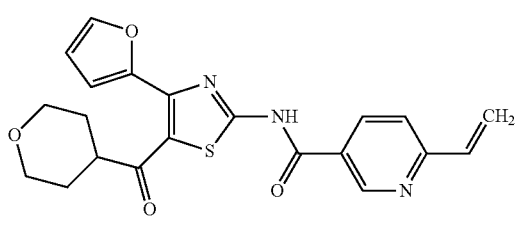
(IE)

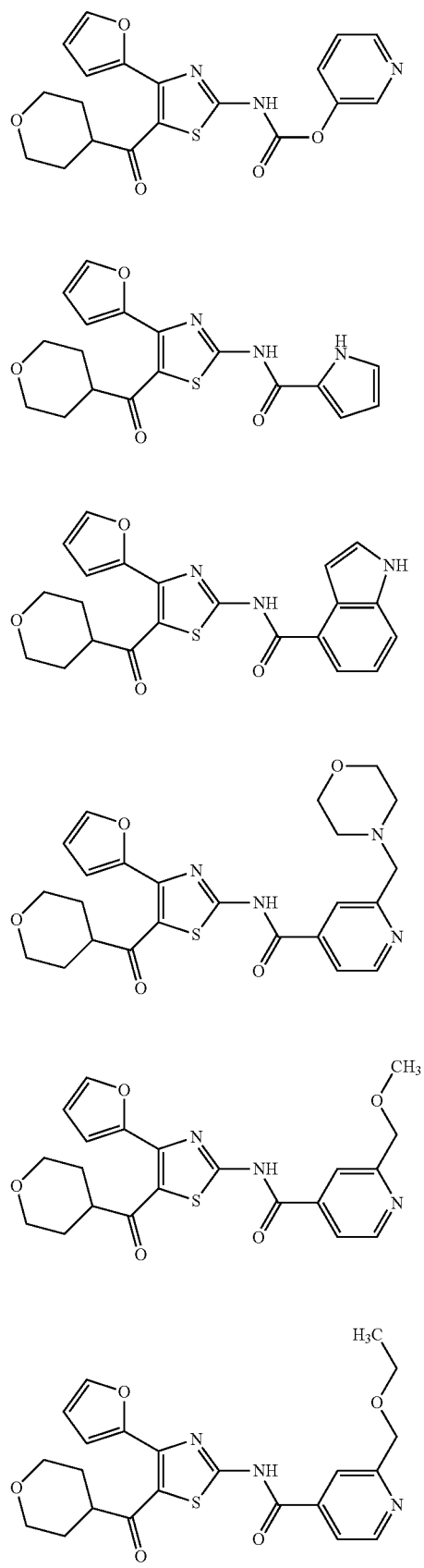
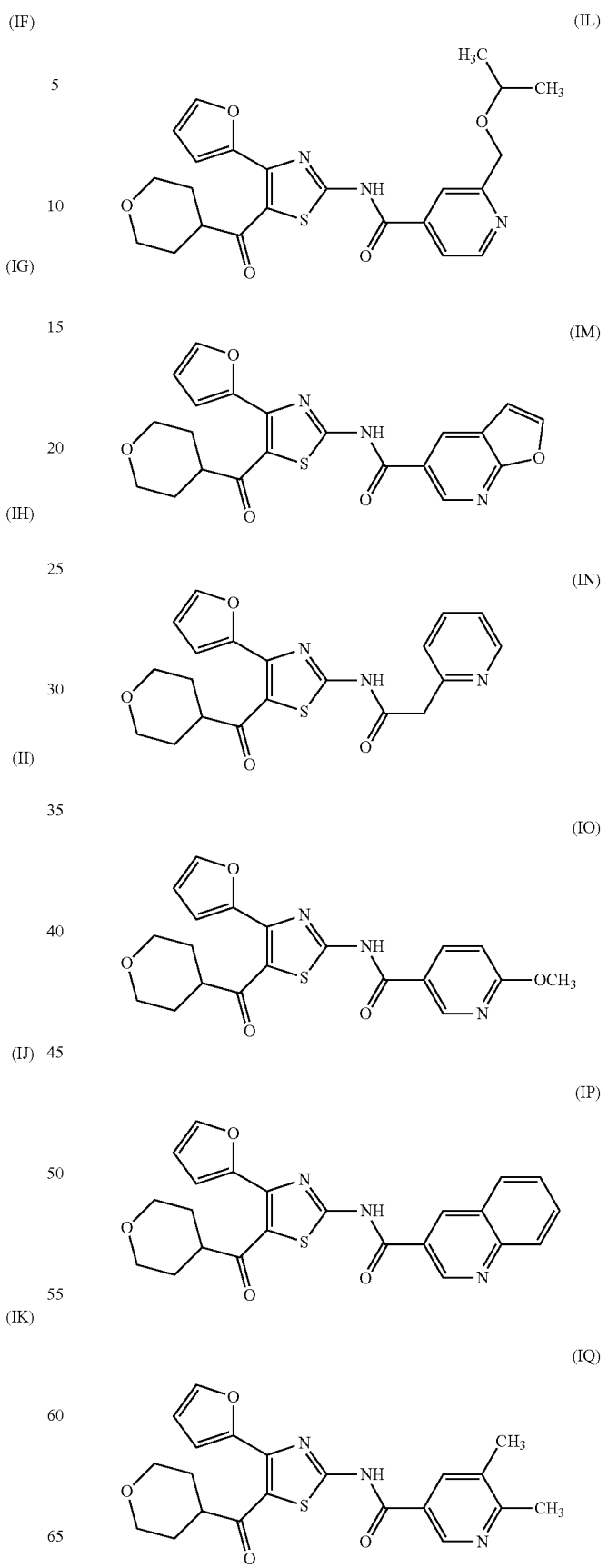

-continued (IR)
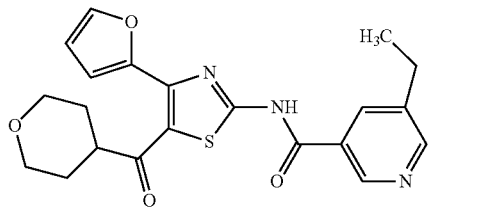

(IS)
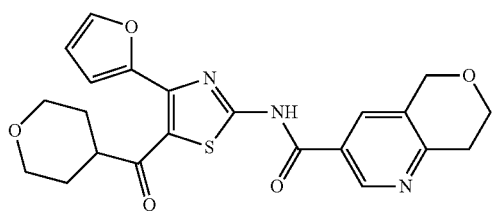

(IT)
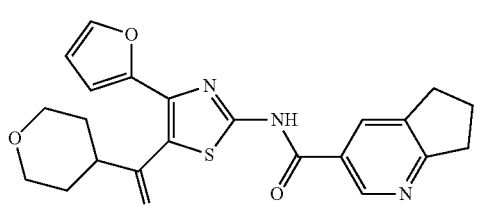

(IU)
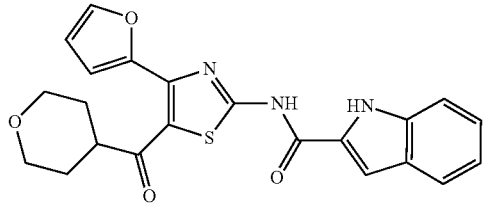

(IV)
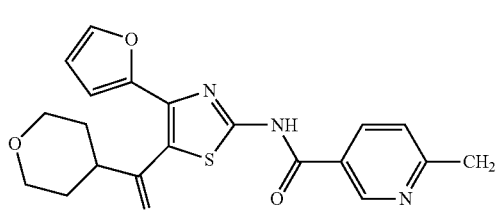

(IW)
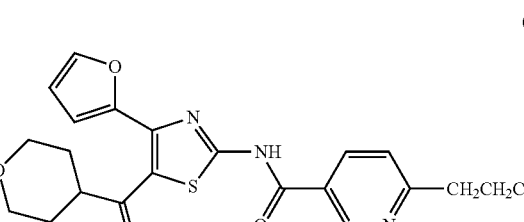

(IX)
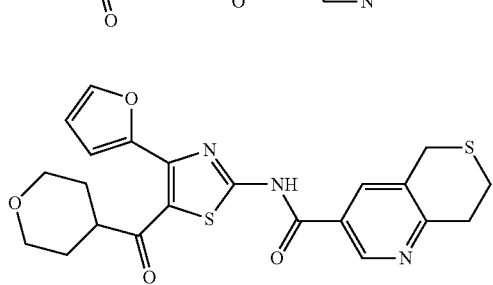

-continued (IY)
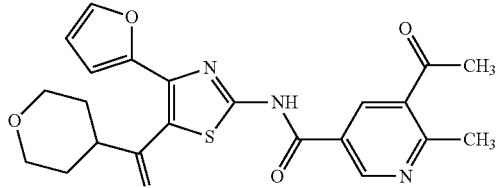

(IZ)
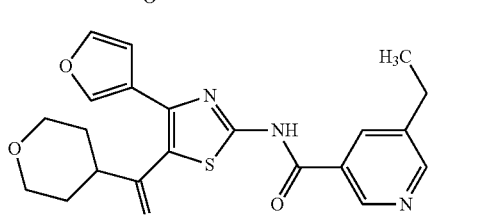

(IAA)
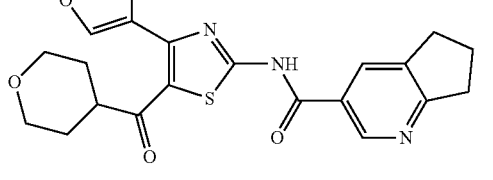

(35) A method of treating and/or preventing a movement disorder, comprising administering an effective amount of a thiazole derivative represented by the formula (I)

(I)
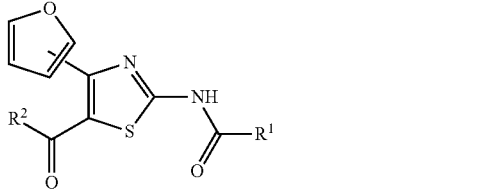

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and $R^2$ represents pyridyl or tetrahydropyranyl, or a pharmaceutically acceptable salt thereof.

(36) The method of (35), wherein $R^1$ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and $R^2$ is pyridyl or tetrahydropyranyl.

(37) The method of (35), wherein $R^1$ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(38) The method of any one of (35)-(37), wherein $R^2$ is pyridyl.

(39) The method of any one of (35)-(37), wherein $R^2$ is tetrahydropyranyl.

(40) The method of (35), wherein the thiazole derivative represented by the formula (I) is a compound represented by any one of the following formulas (IA)-(IAA).
(IA)
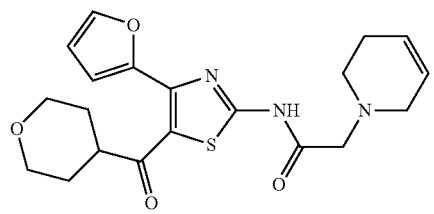
(IB)
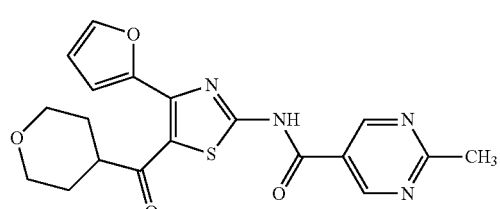
(IC)
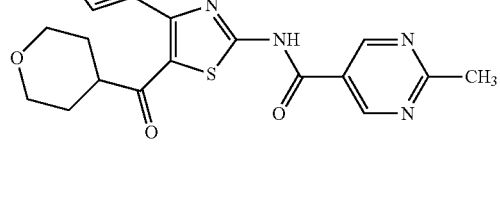
(ID)
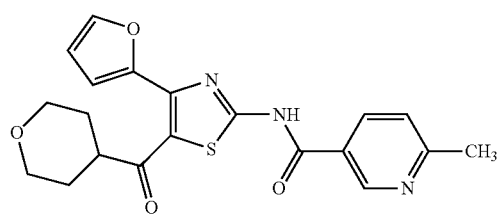
(IE)
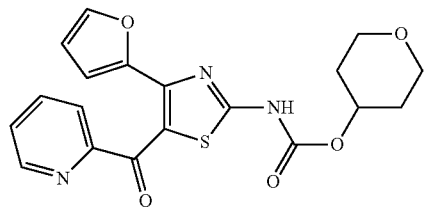
(IF)
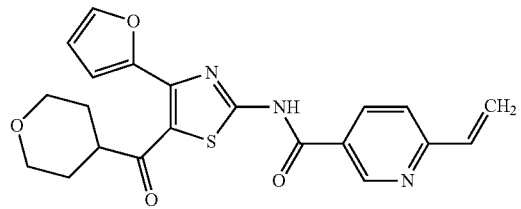
(IF)
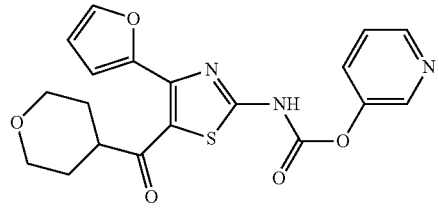
-continued
(IG)
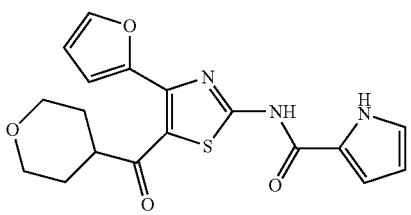
(IH)
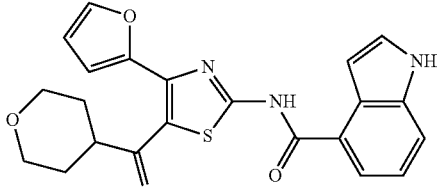
(II)
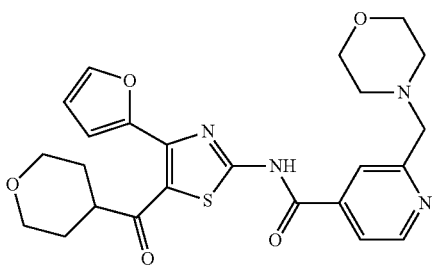
(IJ)
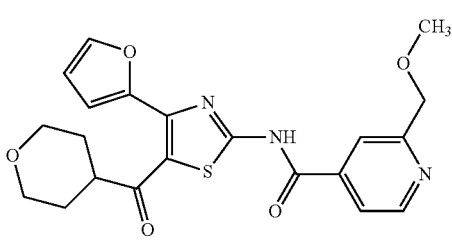
(IK)
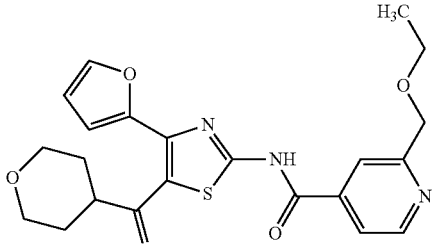
(IL)
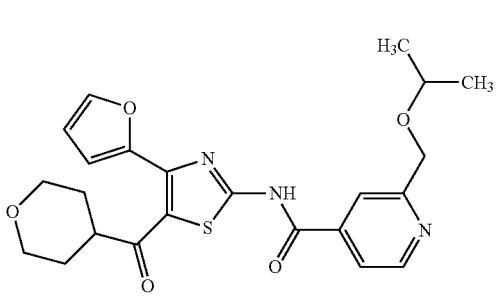

(IM)
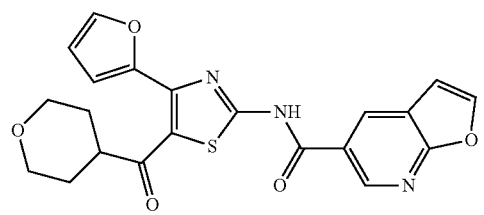
(IN)
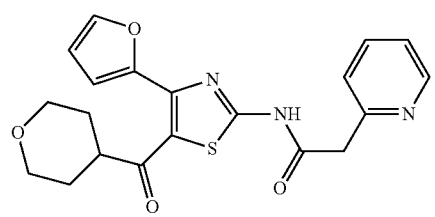
(IO)
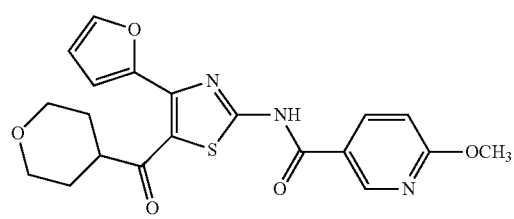
(IP)
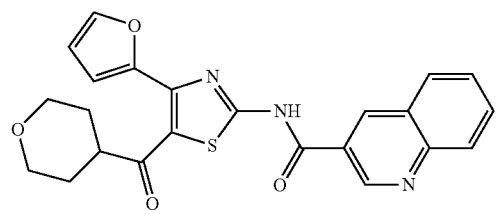
(IQ)
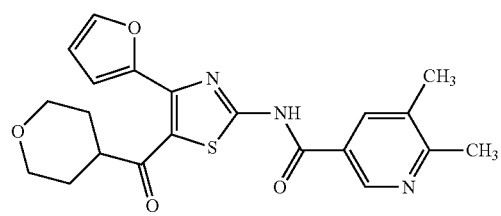
(IR)
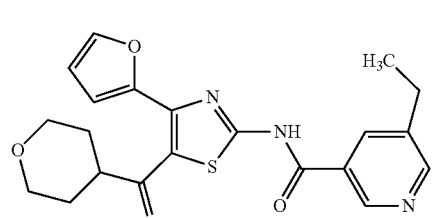
(IS)
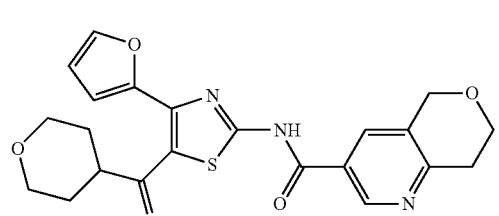
(IT)
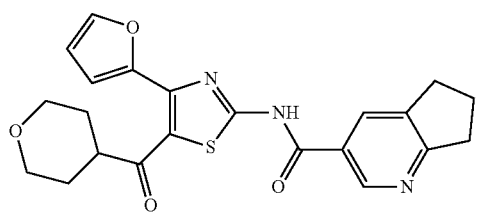
(IU)
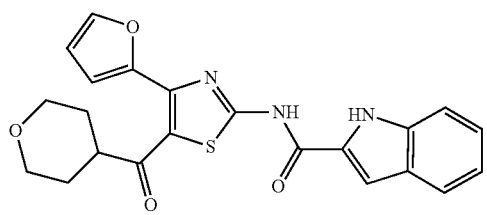
(IV)
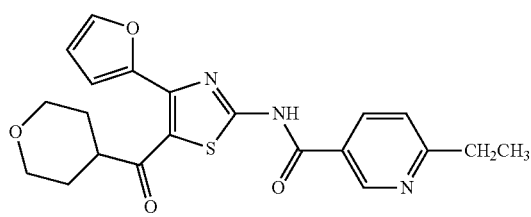
(IW)
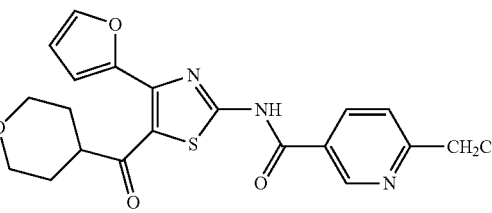
(IX)
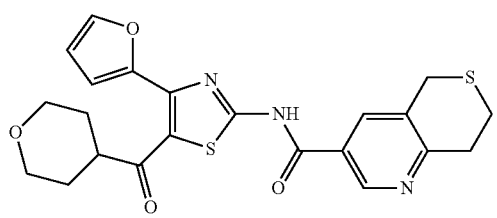
(IY)
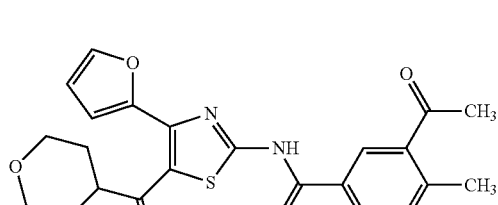
(IZ)
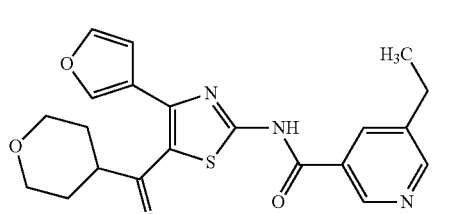

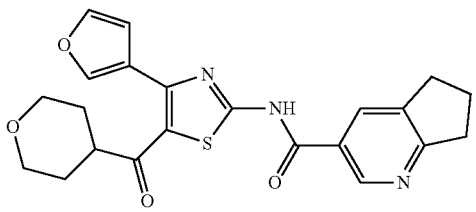
(IAA)

(41) The method of any one of (35)-(40), wherein the movement disorder is extrapyramidal syndrome.
(42) The method of any one of (35)-(40), wherein the movement disorder is bradykinesia, gait disturbance, dystonia, dyskinesia or tardive dyskinesia.
(43) The method of any one of (35)-(40), wherein the movement disorder is a side effect of L-DOPA and/or dopamine agonist therapy.
(44) The method of (43), wherein the side effect is a motor complication.
(45) The method of (44), wherein the motor complication is wearing-off phenomenon.
(46) The method of (44), wherein the motor complication is on-off fluctuation.
(47) The method of (44), wherein the motor complication is dyskinesia.
(48) The method of any one of (35)-(47), wherein the movement disorder is that developed in an advanced stage of Parkinson's disease.
(49) A method of treating and/or preventing. Parkinson's disease, comprising administering (a) an effective amount of a thiazole derivative represented by the formula (I)

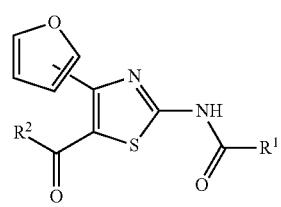
(I)

wherein R¹ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof, and (b) an effective amount of L-DOPA and/or a dopamine agonist, simultaneously or separately at an interval.
(50) The method of (49), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.
(51) The method of (49), wherein R¹ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(52) The method of any one of (49)-(51), wherein R² is pyridyl.
(53) The method of any one of (49)-(51), wherein R² is tetrahydropyranyl.
(54) The method of (49), wherein the thiazole derivative represented by the formula (I) is a compound represented by any one of the following formulas (IA)-(IAA).

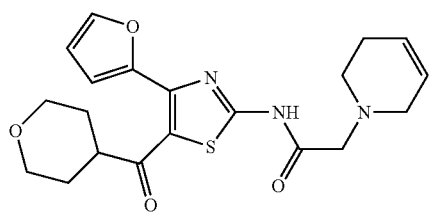
(IA)

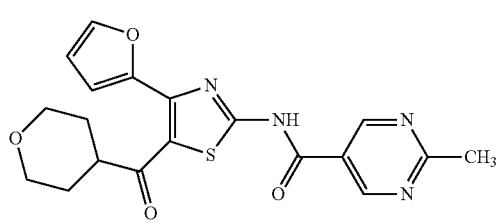
(IB)

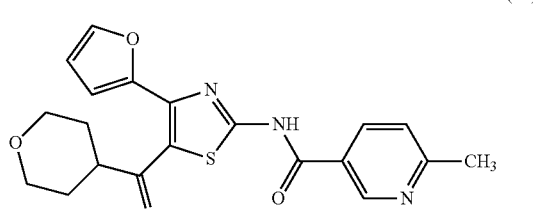
(IC)

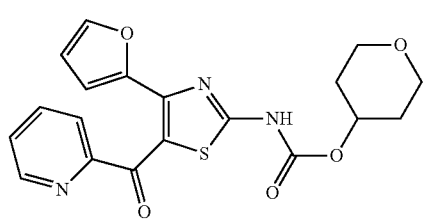
(ID)

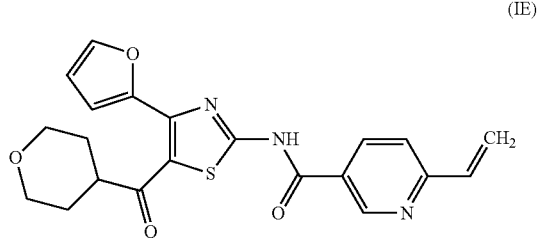
(IE)

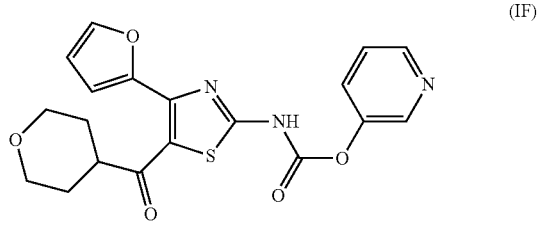
(IF)

(IG)
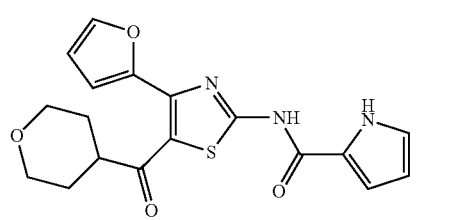
(IH)
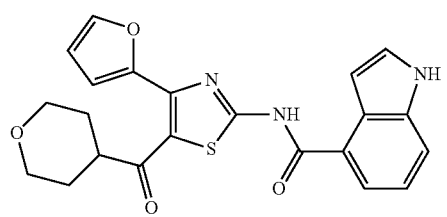
(II)
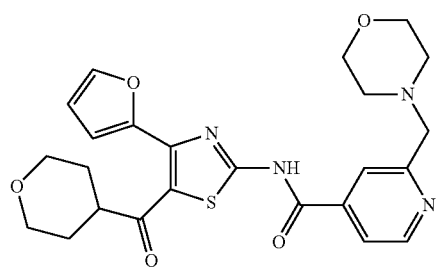
(IJ)
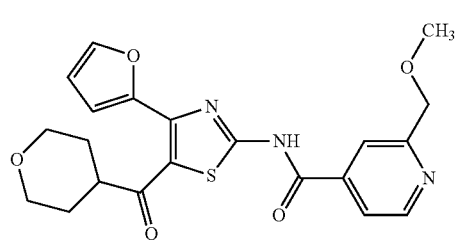
(IK)
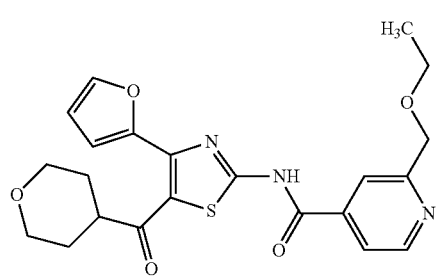
(IL)
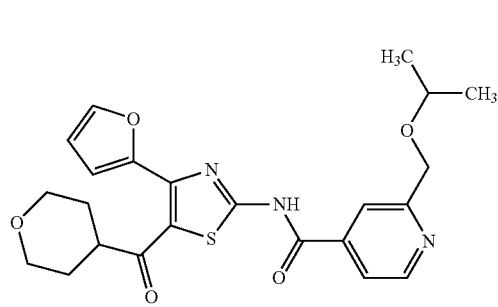
(IM)
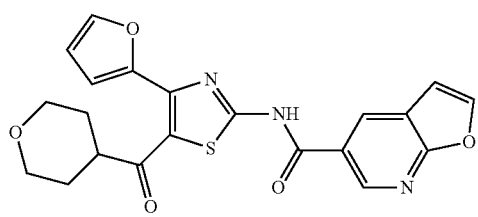
(IN)
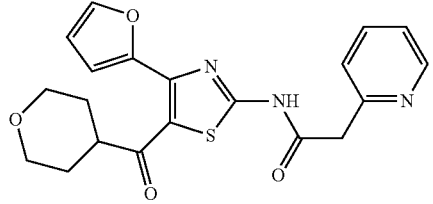
(IO)
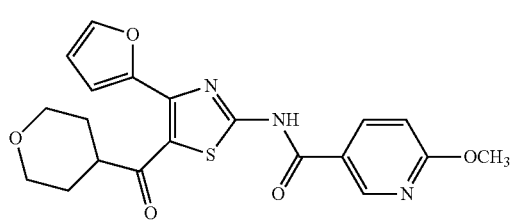
(IP)
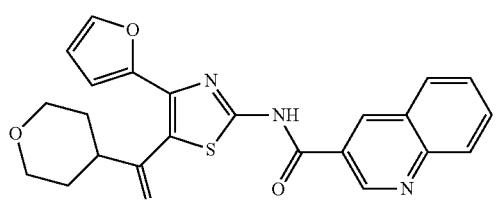
(IQ)
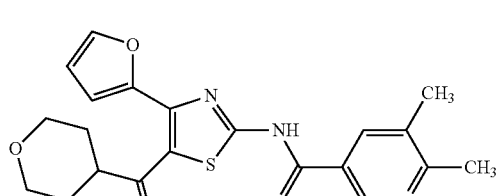
(IR)
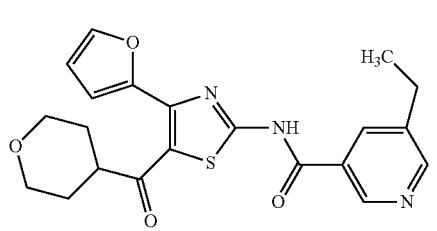
(IS)
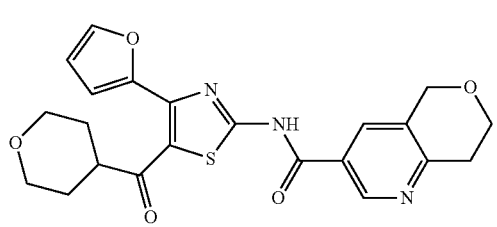

-continued (IT)
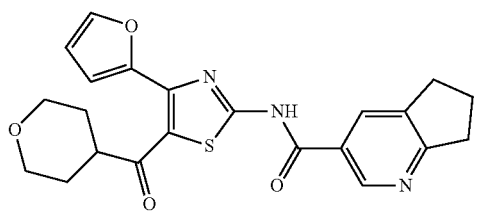

(IU)
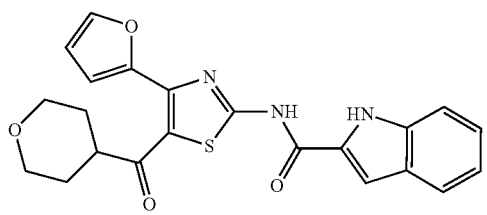

(IV)
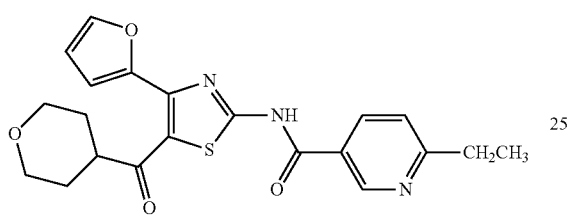

(IW)
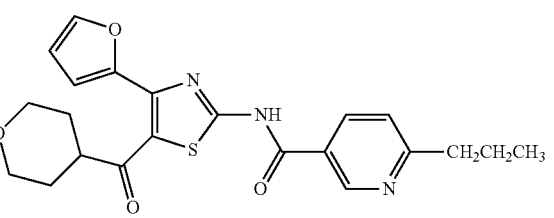

(IX)
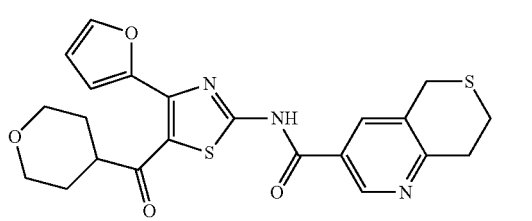

(IY)
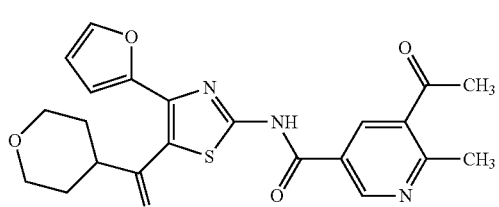

(IZ)
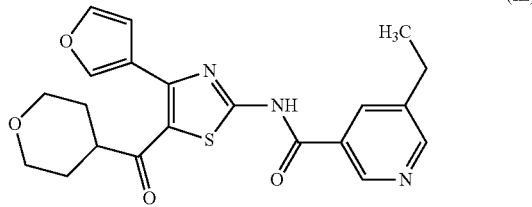

-continued (IAA)
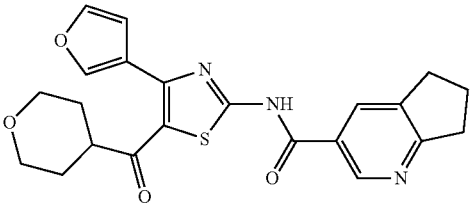

(55) The method of any one of (49)-(54), wherein the Parkinson's disease is that in an advanced stage.

(56) A thiazole derivative represented by the formula (I)

(I)
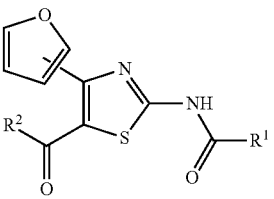

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and $R^2$ represents pyridyl or tetrahydropyranyl, or a pharmaceutically acceptable salt thereof, for use in the treatment and/or prophylaxis of a movement disorder.

(57) The thiazole derivative or a pharmaceutically acceptable salt thereof of (56), wherein $R^1$ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and $R^2$ is pyridyl or tetrahydropyranyl.

(58) The thiazole derivative or a pharmaceutically acceptable salt thereof of (56), wherein $R^1$ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(59) The thiazole derivative or a pharmaceutically acceptable salt thereof of any one of (56)-(58), wherein $R^2$ is pyridyl.

(60) The thiazole derivative or a pharmaceutically acceptable salt thereof of any one of (56)-(58), wherein $R^2$ is tetrahydropyranyl.

(61) The thiazole derivative or a pharmaceutically acceptable salt thereof of (56), wherein the thiazole derivative represented by the formula (I) is a compound represented by any one of the following formulas (IA)-(IAA).

(IA)
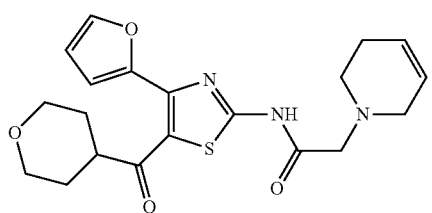
(IB)
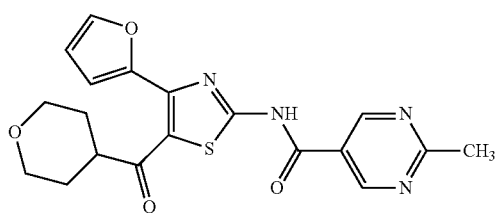
(IC)
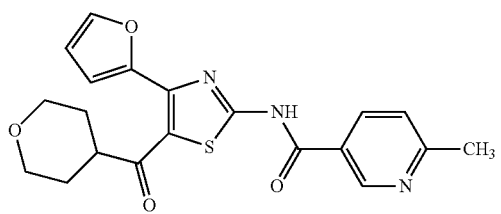
(ID)
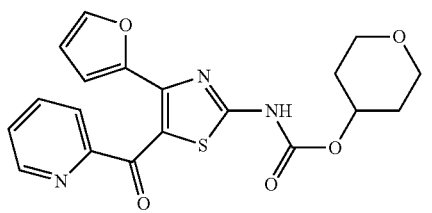
(IE)
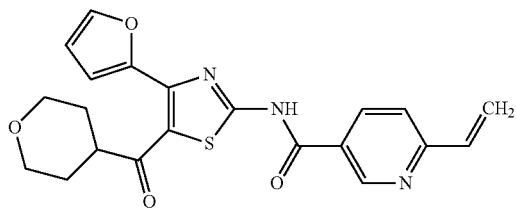
(IF)
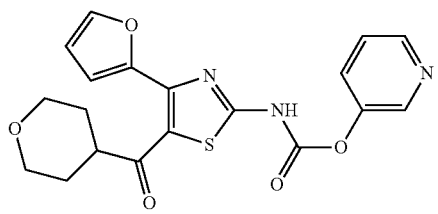
(IG)
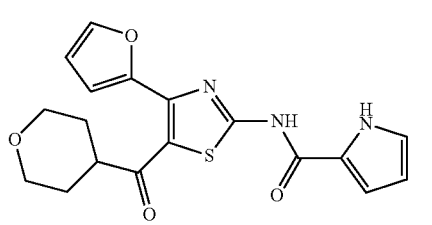
(IH)
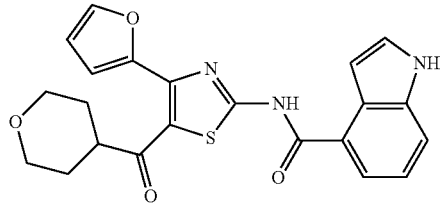
(II)
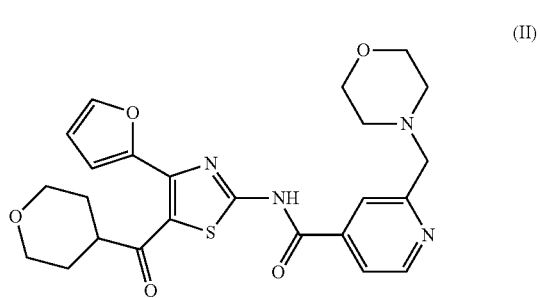
(IJ)
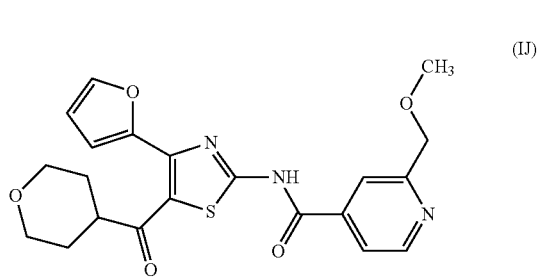
(IK)
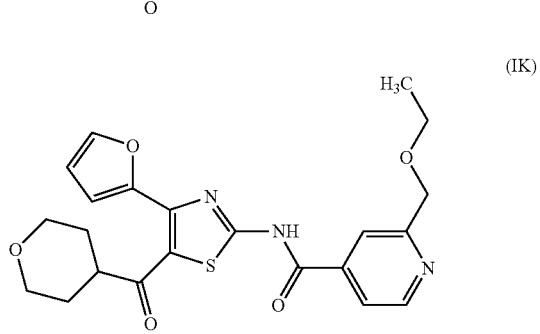
(IL)
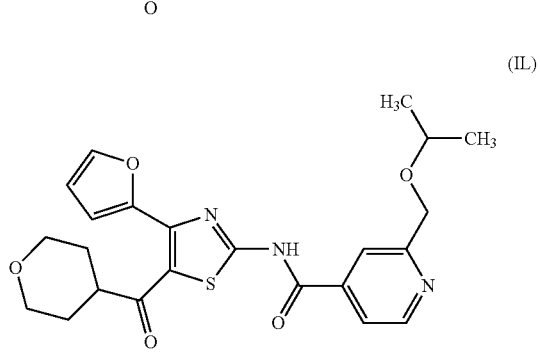
(IM)
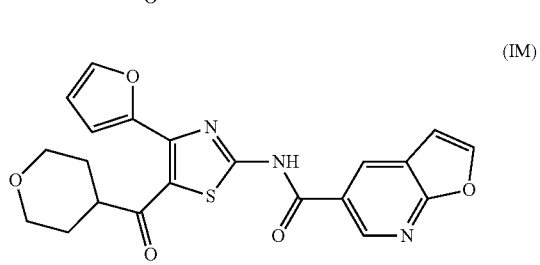

37

-continued (IN)
(IO)
(IP)
(IQ)
(IR)
(IS)
(IT)

38

-continued (IU)
(IV)
(IW)
(IX)
(IY)
(IZ)
(IAA)

(62) The thiazole derivative or a pharmaceutically acceptable salt thereof of any one of (56)-(61), wherein the movement disorder is extrapyramidal syndrome.
(63) The thiazole derivative or a pharmaceutically acceptable salt thereof of any one of (56)-(61), wherein the movement disorder is bradykinesia, gait disturbance, dystonia, dyskinesia or tardive dyskinesia.
(64) The thiazole derivative or a pharmaceutically acceptable salt thereof of any one of (56)-(61), wherein the movement disorder is a side effect of L-DOPA and/or dopamine agonist therapy.
(65) The thiazole derivative or a pharmaceutically acceptable salt thereof of (64), wherein the side effect is a motor complication.
(66) The thiazole derivative or a pharmaceutically acceptable salt thereof of (65), wherein the motor complication is wearing-off phenomenon.
(67) The thiazole derivative or a pharmaceutically acceptable salt thereof of (65), wherein the motor complication is on-off fluctuation.
(68) The thiazole derivative or a pharmaceutically acceptable salt thereof of (65), wherein the motor complication is dyskinesia.
(69) The thiazole derivative or a pharmaceutically acceptable salt thereof of any one of (56)-(68), wherein the movement disorder is that developed in an advanced stage of Parkinson's disease.
(70) A compound represented by any one of the following formulas (IE)-(IAA), or a pharmaceutically acceptable salt thereof.

(IE)

(IF)

(IG)

(IH)

-continued (II)
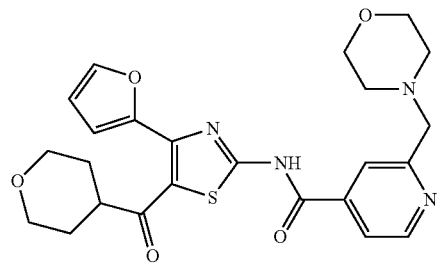

(IJ)
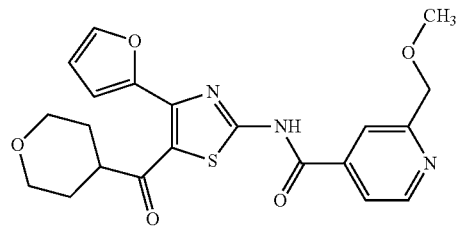

(IK)
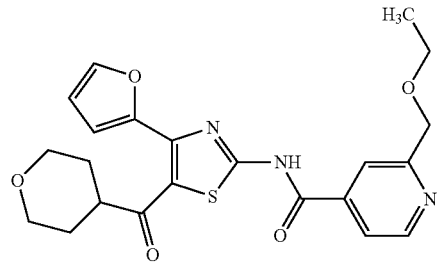

(IL)
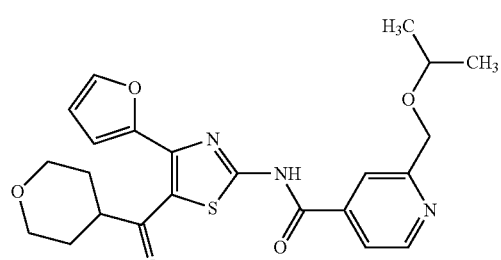

(IM)
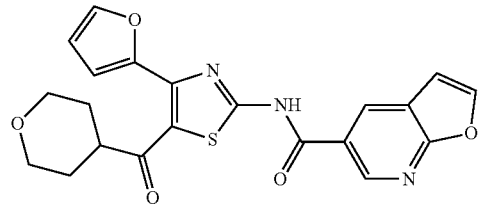

(IN)
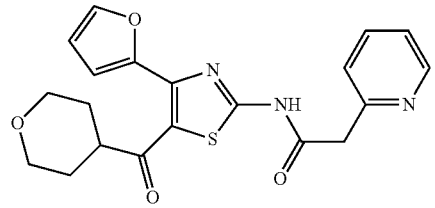

(IO)
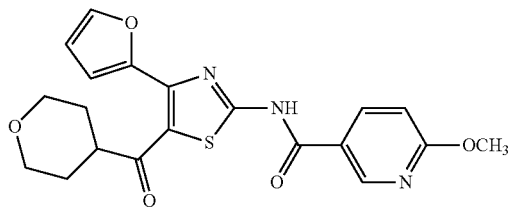
(IP)
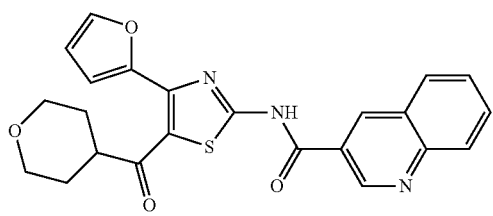
(IQ)
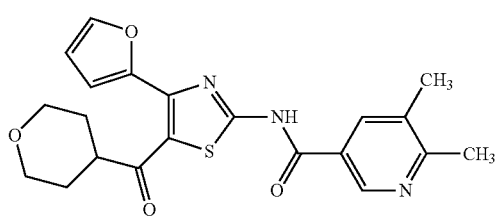
(IR)
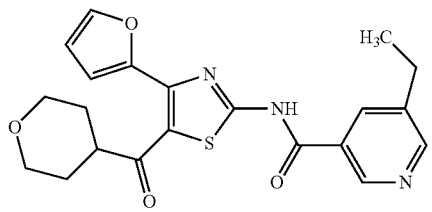
(IS)
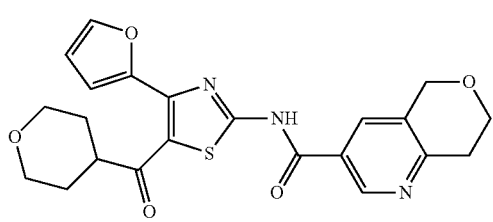
(IT)
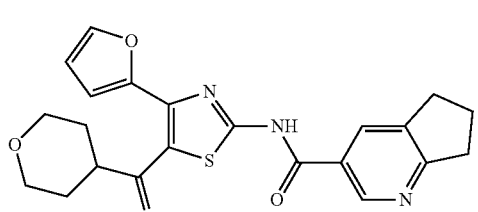
(IU)
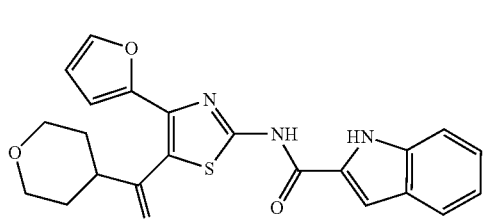
(IV)
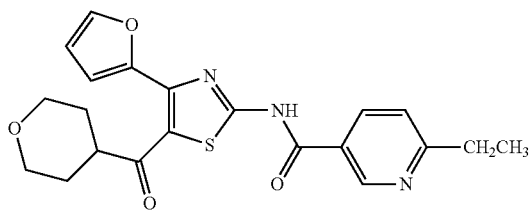
(IW)
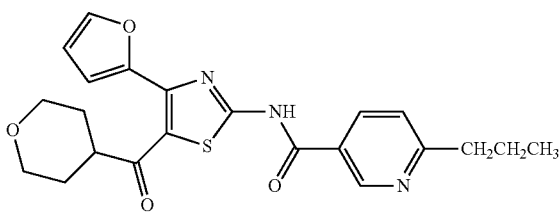
(IX)
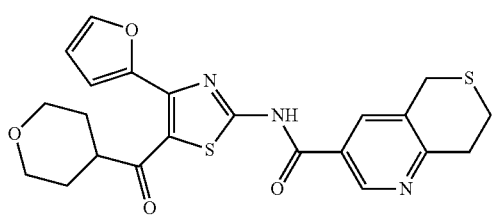
(IY)
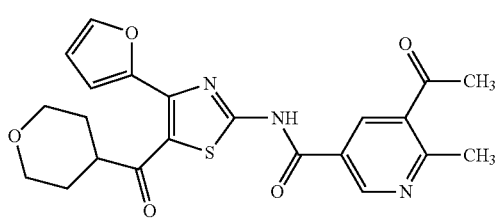
(IZ)
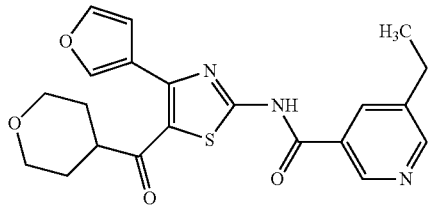
(IAA)
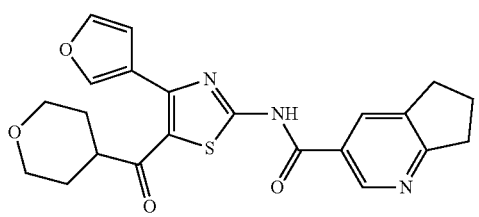
(71) A combination of (a) a thiazole derivative represented by the formula (I)

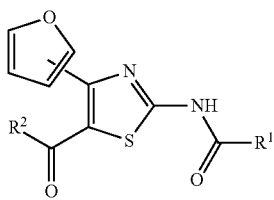
(I)

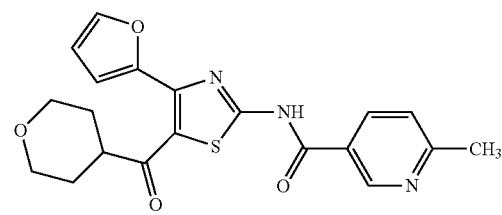
(IC)

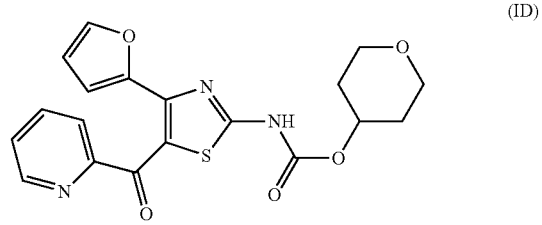
(ID)

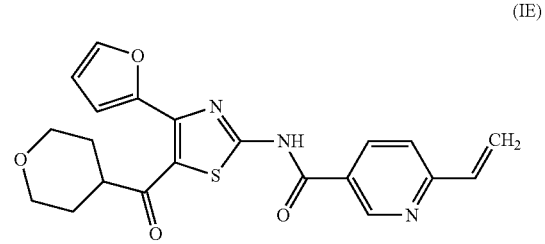
(IE)

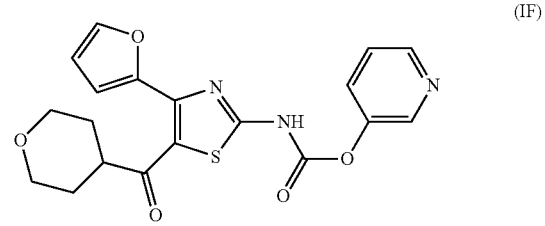
(IF)

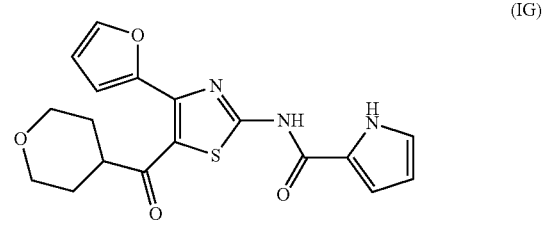
(IG)

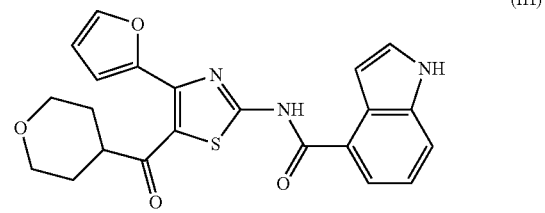
(IH)

wherein R¹ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof, and (b) L-DOPA and/or a dopamine agonist, for use in the treatment and/or prophylaxis of Parkinson's disease.

(72) The combination of (71), wherein the use is for administering (a) and (b) simultaneously or separately at an interval.

(73) The combination of (71) or (72), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.

(74) The combination of (71) or (72), wherein R¹ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(75) The combination of any one of (71)-(74), wherein R² is pyridyl.

(76) The combination of any one of (71)-(74), wherein R² is tetrahydropyranyl.

(77) The combination of (71) or (72), wherein the thiazole derivative represented by the formula (I) is a compound represented by any one of the following formulas (IA)-(IAA).

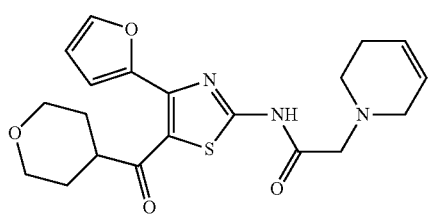
(IA)

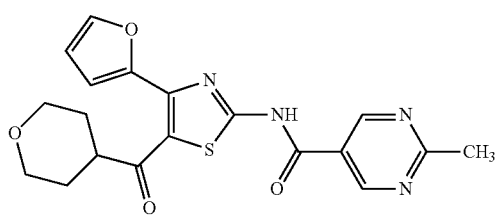
(IB)

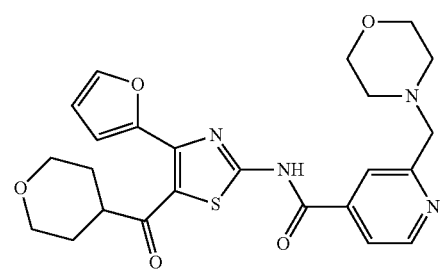
(II)

(IJ)
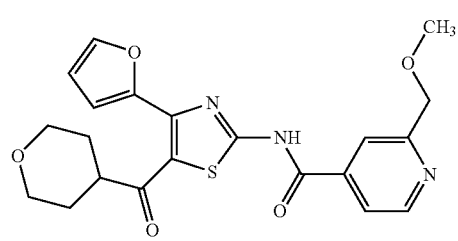
(IK)
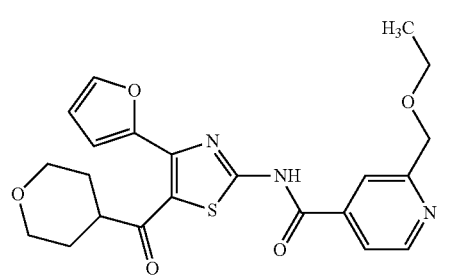
(IL)
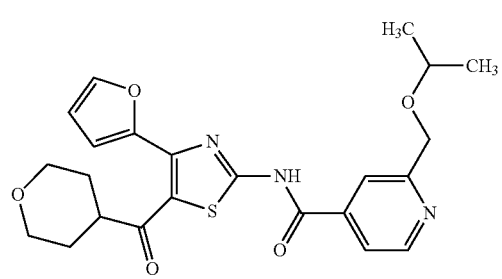
(IM)
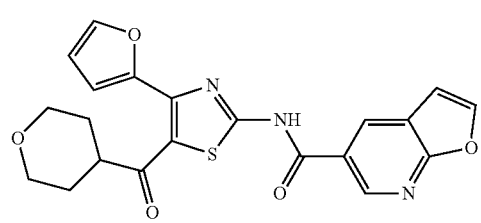
(IN)
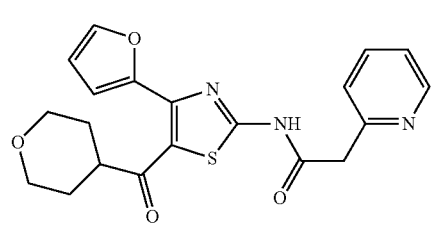
(IO)
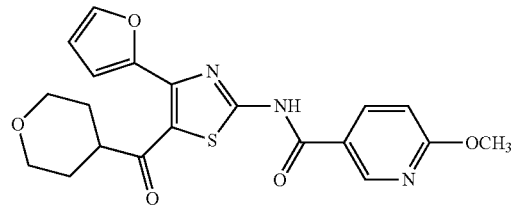
(IP)
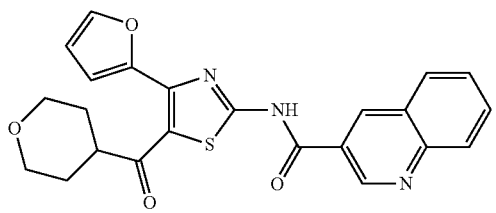
(IQ)
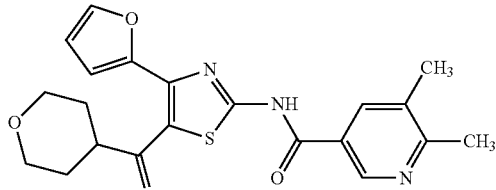
(IR)
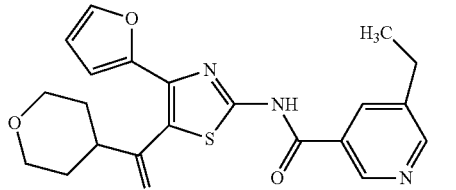
(IS)
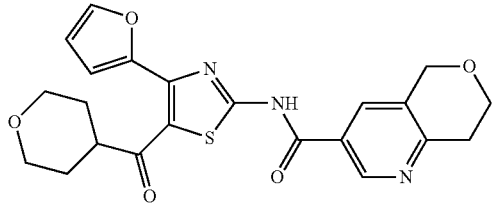
(IT)
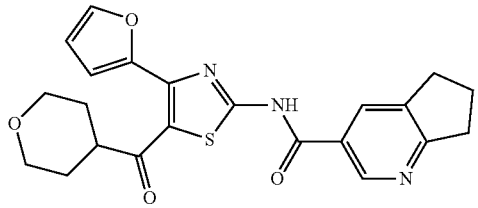
(IU)
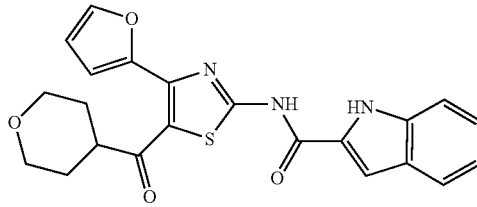
(IV)

-continued

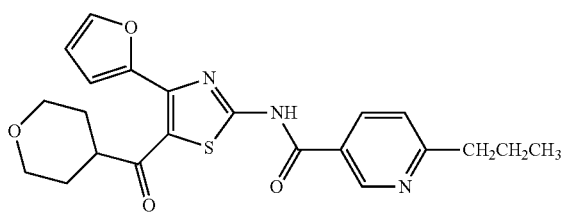
(IW)

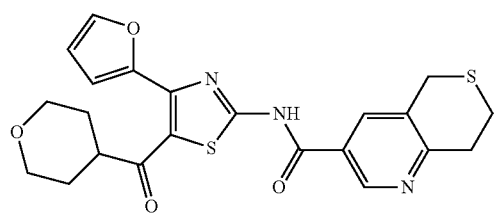
(IX)

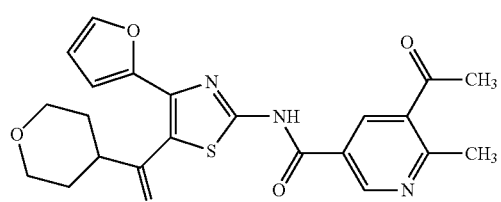
(IY)

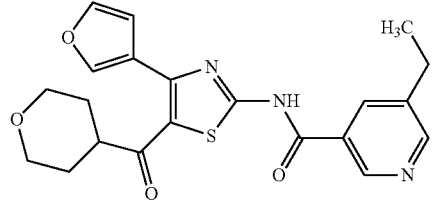
(IZ)

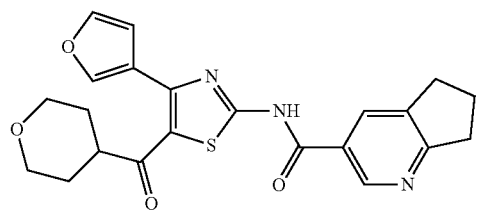
(IAA)

(78) The combination of any one of (71)-(77), wherein the Parkinson's disease is that in an advanced stage.
(79) Use of a thiazole derivative represented by the formula (I)

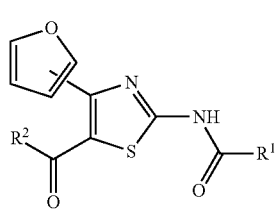
(I)

wherein $R^1$ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and $R^2$ represents pyridyl or tetrahydropyranyl, or a pharmaceutically acceptable salt thereof, for the manufacture of an agent for the treatment and/or prophylaxis of a movement disorder.

(80) The use of (79), wherein $R^1$ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and $R^2$ is pyridyl or tetrahydropyranyl.

(81) The use of (79), wherein $R^1$ is pyridyl or pyrimidinyl, each of which is optionally substituted by 1 to 3 substituents selected from the group consisting of halogen; lower alkyl optionally substituted by lower alkoxy or morpholino; lower alkoxy; lower alkanoyl; and vinyl.

(82) The use of any one of (79)-(81), wherein $R^2$ is pyridyl.

(83) The use of any one of (79)-(81), wherein $R^2$ is tetrahydropyranyl.

(84) The use of (79), wherein the thiazole derivative represented by the formula (I) is a compound represented by any one of the following formulas (IA)-(IAA).

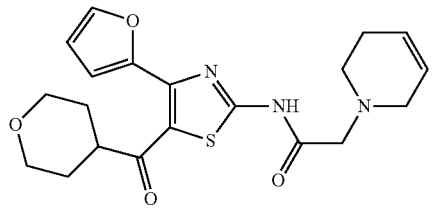
(IA)

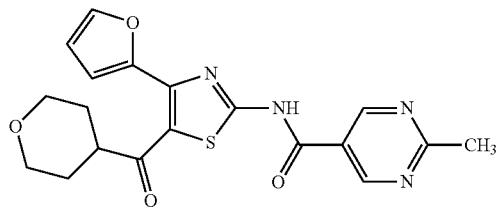
(IB)

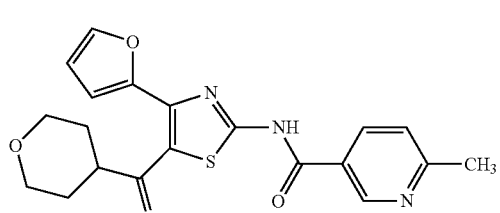
(IC)

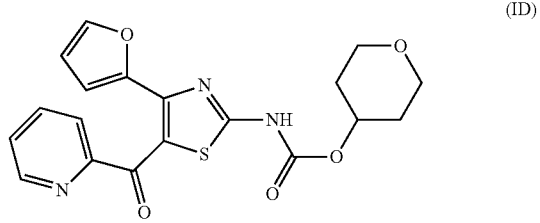
(ID)

(IE)
(IF)
(IG)
(IH)
(II)
(IJ)
(IK)
(IL)
(IM)
(IN)
(IO)
(IP)

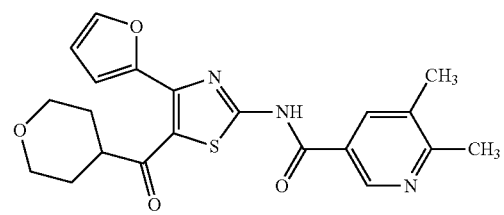 (IQ)

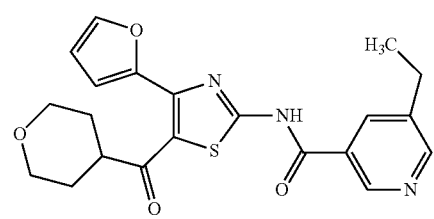 (IR)

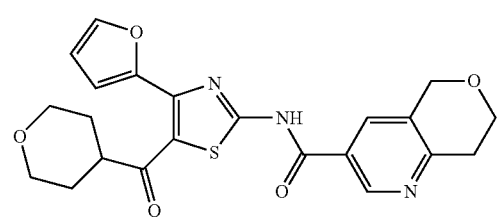 (IS)

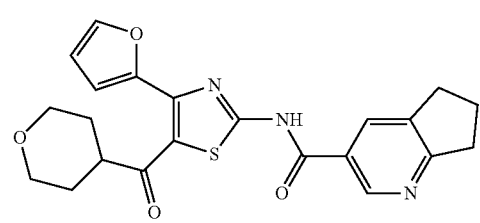 (IT)

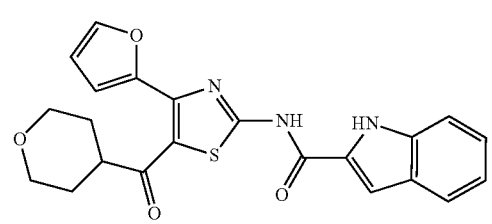 (IU)

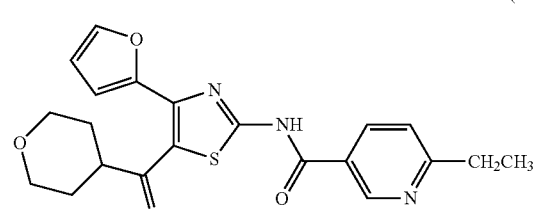 (IV)

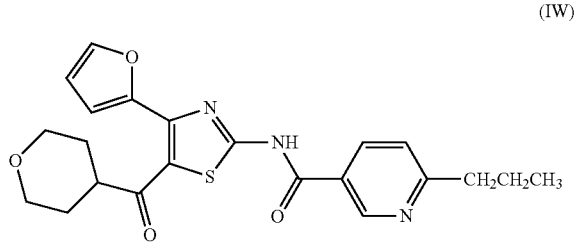 (IW)

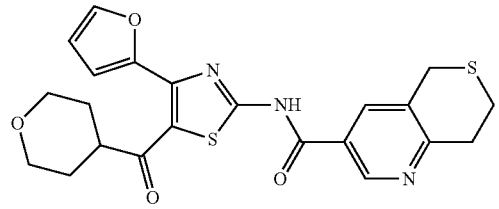 (IX)

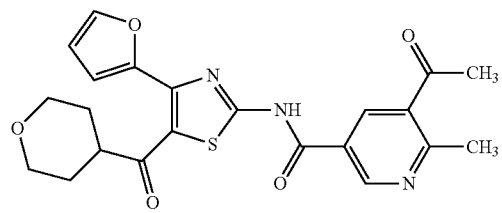 (IY)

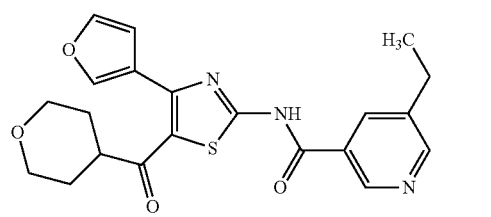 (IZ)

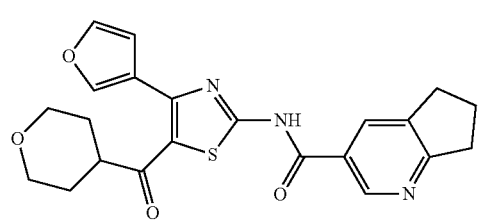 (IAA)

(85) The use of any one of (79)-(84), wherein the movement disorder is extrapyramidal syndrome.

(86) The use of any one of (79)-(84), wherein the movement disorder is bradykinesia, gait disturbance, dystonia, dyskinesia or tardive dyskinesia.

(87) The use of any one of (79)-(84), wherein the movement disorder is a side effect of L-DOPA and/or dopamine agonist therapy.

(88) The use of (87), wherein the side effect is a motor complication.

(89) The use of (88), wherein the motor complication is wearing-off phenomenon.

(90) The use of (88), wherein the motor complication is on-off fluctuation.

(91) The use of (88), wherein the motor complication is dyskinesia.

(92) The use of any one of (79)-(91), wherein the movement disorder is that developed in an advanced stage of Parkinson's disease.

(93) Use of (a) a thiazole derivative represented by the formula (I)

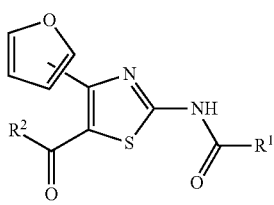
(I)

wherein R¹ represents aryl, aralkyl, an aromatic heterocyclic group, aromatic heterocycle-alkyl, aliphatic heterocycle-alkyl or tetrahydropyranyloxy, each of which is optionally substituted by 1 to 3 substituents selected from the group consisting of halogen; lower alkyl optionally substituted by lower alkoxy or morpholino; lower alkoxy; lower alkanoyl; and vinyl, and R² represents pyridyl or tetrahydropyranyl, or a pharmaceutically acceptable salt thereof, and (b) L-DOPA and/or a dopamine agonist for the manufacture of an agent for the treatment and/or prophylaxis of Parkinson's disease.

(94) The use of (93), wherein the agent for the treatment and/or prophylaxis of Parkinson's disease is that for administering (a) and (b) simultaneously or separately at an interval.

(95) The use of (93) or (94), wherein R¹ is phenyl, pyridyl, pyrimidinyl, 5,6-dihydro-2H-pyridylmethyl or tetrahydropyranyloxy, each of which is optionally substituted by 1 to 3 substituents selected from a fluorine atom, a chlorine atom, a bromine atom, methyl, ethyl, methoxy and ethoxy, and R² is pyridyl or tetrahydropyranyl.

(96) The agent of (93) or (94), wherein R¹ is pyridyl or pyrimidinyl, each of which is optionally substituted by 0.1 to 3 substituents selected from the group consisting of halogen; lower alkyl optionally substituted by lower alkoxy or morpholino; lower alkoxy; lower alkanoyl; and vinyl.

(97) The use of any one of (93)-(96), wherein R² is pyridyl.

(98) The use of any one of (93)-(96), wherein R² is tetrahydropyranyl.

(99) The use of (93) or (94), wherein the thiazole derivative represented by the formula (I) is a compound represented by any one of the following formulas (IA)-(IAA).

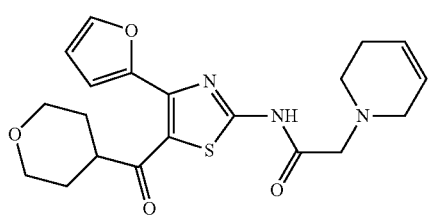
(IA)

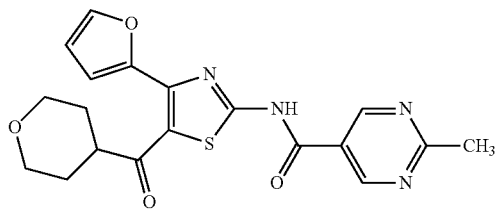
(IB)

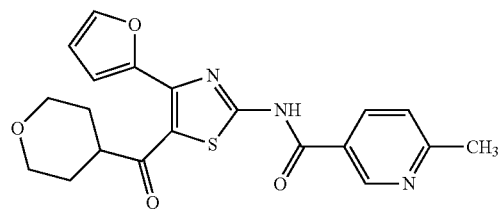
(IC)

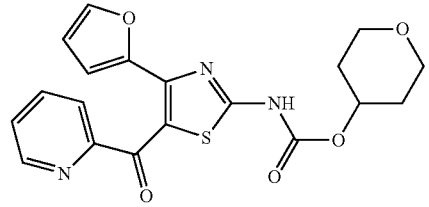
(ID)

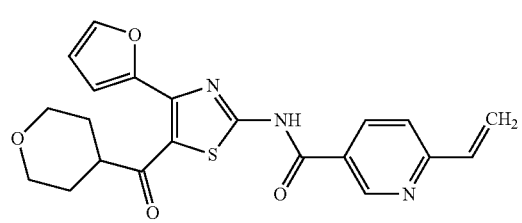
(IE)

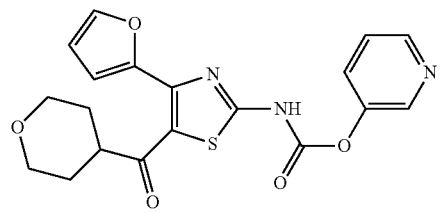
(IF)

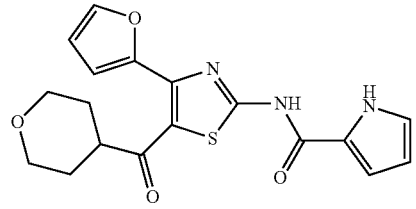
(IG)

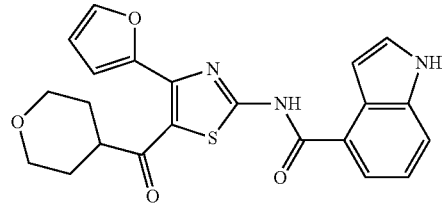
(IH)

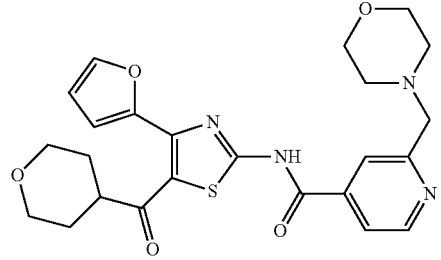
(II)

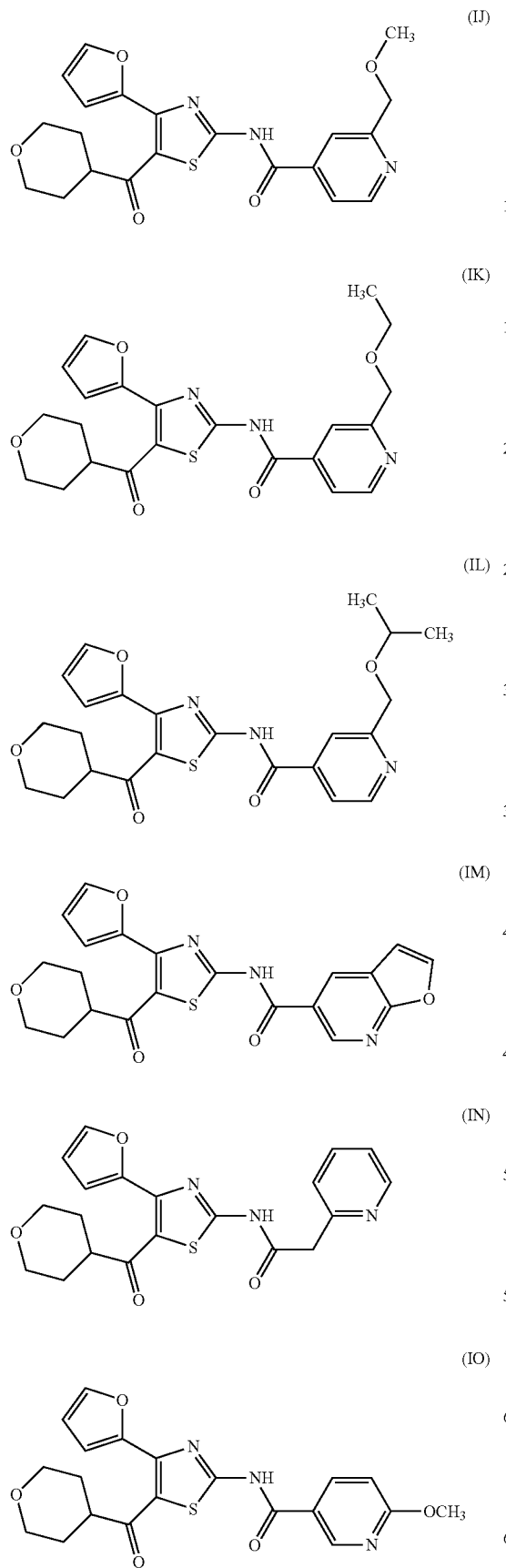
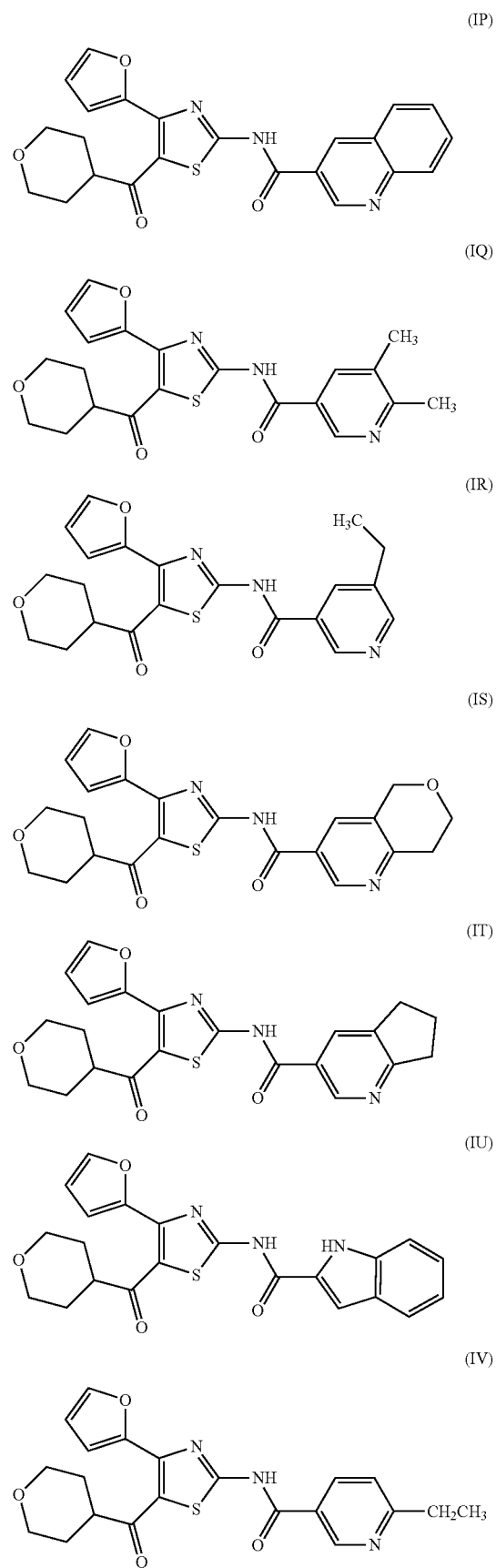

(IW)

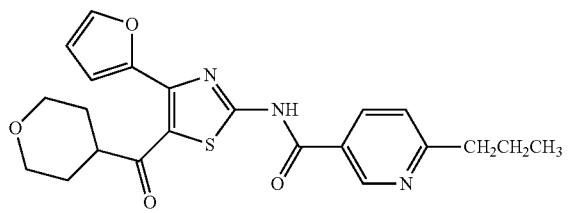

(IX)

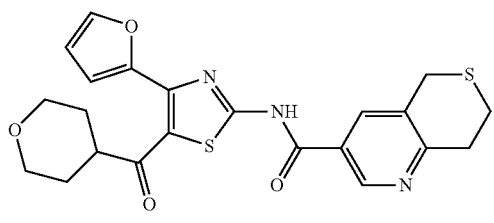

(IY)

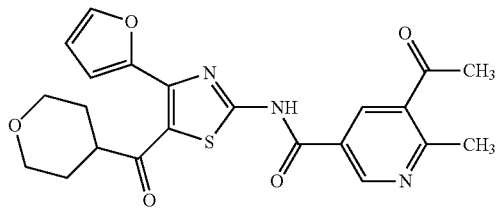

(IZ)

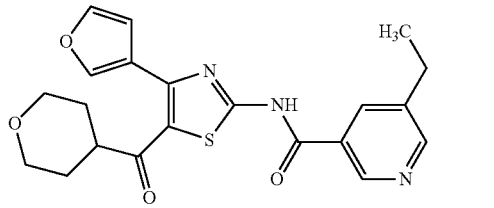

(IAA)

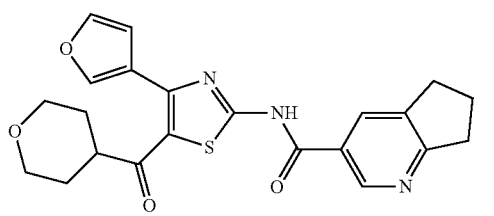

(100) The use of any one of (93)-(99), wherein the Parkinson's disease is that in an advanced stage.

Effect of the Invention

The present invention provides an agent for the treatment and/or prophylaxis of a movement disorder, comprising a thiazole derivative or a pharmaceutically acceptable salt thereof as an active ingredient; a pharmaceutical composition comprising (a) a thiazole derivative or a pharmaceutically acceptable salt thereof and (b) L-DOPA and/or a dopamine agonist; an agent for the treatment and/or prophylaxis of Parkinson's disease comprising (a) a thiazole derivative or a pharmaceutically acceptable salt thereof and (b) L-DOPA and/or a dopamine agonist in combination; a kit comprising (a) a first component comprising a thiazole derivative or a pharmaceutically acceptable salt thereof and (b) a second component comprising L-DOPA and/or a dopamine agonist; a thiazole derivative or a pharmaceutically acceptable salt thereof, which has a selective adenosine $A_{2A}$ antagonistic activity and is useful for the treatment of a movement disorder, and the like.

MODE FOR CARRYING OUT THE INVENTION

Figure 1:
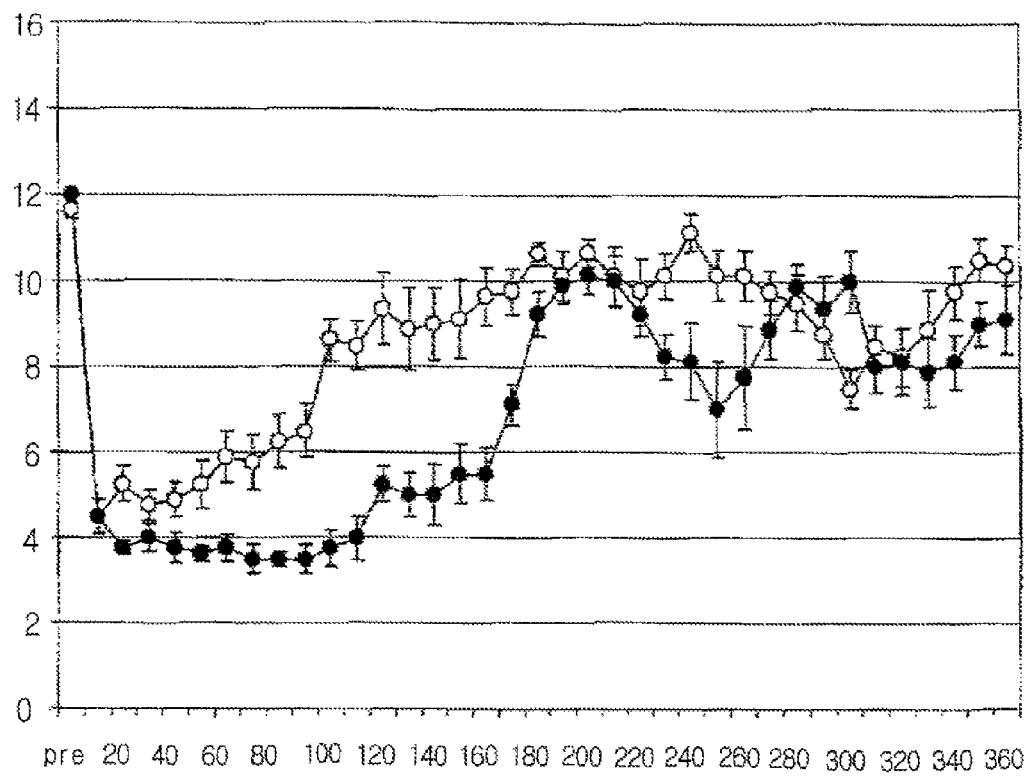
FIG. 1 shows the effect of compound (IC) on the motor disability score in the Test Example 3. The vertical axis shows the motor disability score, and the horizontal axis shows time (min) after administration. ○ shows a combination of solvent and L-DOPA, and ● shows a combination of compound (IC) and L-DOPA.

The movement disorder is a neurological condition characterized by motor control disorder such as paucity or lack of movement, extrapyramidal syndrome or the like, hypermobilities (e.g., dystonia, dyskinesia, tardive dyskinesia, tremor, chorea, ballism, akathisia, athetosis, bradykinesia, gait disturbance, freezing, rigidity, postural instability, myoclonus, tics or Tourette syndrome, postural reflex disorder or the like) or the like.

The movement disorder in the agent for the treatment and/or prophylaxis of a movement disorder of the present invention means the above-mentioned movement disorder, and preferably means, for example, motor control disorder such as extrapyramidal syndrome or the like, tremor, chorea, athetosis, bradykinesia, gait disturbance, dystonia, dyskinesia, tardive dyskinesia, postural reflex disorder or the like. Therefore, the agent for the treatment and/or prophylaxis of a movement disorder of the present invention can treat and/or prevent or reduce or suppress these diseases and/or symptoms (e.g., motor control disorder such as extrapyramidal syndrome or the like, tremor, chorea, athetosis, bradykinesia, gait disturbance, dystonia, dyskinesia, tardive dyskinesia, postural reflex disorder or the like, preferably, for example, extrapyramidal syndrome, bradykinesia, gait disturbance, dystonia, dyskinesia, tardive dyskinesia, postural reflex disorder or the like, and more preferably, extrapyramidal syndrome, bradykinesia, gait disturbance, dystonia, dyskinesia, tardive dyskinesia or the like).

The movement disorder in the agent for the treatment and/or prophylaxis of a movement disorder of the present invention also encompasses side effects of L-DOPA and/or dopamine agonist therapy (e.g., motor complications such as wearing-off phenomenon, on-off fluctuation, dyskinesia or the like).

It is known that although L-DOPA provides robust and rapid therapeutic benefits in Parkinson's disease, eventually, severe and uncomfortable adverse reactions including motor complications such as wearing-off phenomenon, on-off fluctuation, dyskinesia and the like appear (Marsden et al., "Fluctuat ionsind is ability in Parkinson's disease: clinical aspects" In: Marsden, C D, Fahn S., eds. Movement disorders. New York: Butterworth Scientific, p. 96-122 (1982)). It is also known that an administration of L-DOPA alone causes side effects such as nausea, vomiting, anorexia and the like.

A dopamine agonist can also induce dyskinesia. Use of a dopamine agonist is often limited due to neuropsychiatric side effects, particularly, hallucination and psychosis. Although a dopamine agonist provides advantages when used as the adjunct in the treatment with L-DOPA, control thereby of motor complication caused by L-DOPA is extremely difficult or even impossible, as mentioned above (Olanow, Watts and Kollereds., An Algorithm (Decision Tree) for the Management of Parkinson's Disease: Treatment Guidelines, Neurology 56, Suppl. 5 (2001)). Furthermore, it is reported that excessive daytime sleepiness associated with Parkinson's disease may be aggravated by L-DOPA and/or a dopamine agonist (Neurology, vol. 67, p. 853 (2006)).

The side effects in the L-DOPA and/or dopamine agonist therapy in the present invention refer to the above-mentioned side effects that occur in the treatment and/or prophylaxis of Parkinson's disease and the like using L-DOPA and/or a dopamine agonist. For example, they include motor complications such as wearing-off phenomenon, on-off fluctuation, dyskinesia and the like, nausea, vomiting, anorexia, hallucination and psychological symptom, excessive daytime sleepiness, preferably, motor complications such as wearing-off phenomenon, on-off fluctuation, dyskinesia and the like, and the like. That is, the agent for the treatment and/or prophylaxis of a movement disorder of the present invention can reduce or suppress a side effect that appears on administration of L-DOPA and/or a dopamine agonist, specifically, a motor complication such as wearing-off phenomenon, on-off fluctuation, dyskinesia or the like, nausea, vomiting, anorexia, hallucination and psychological symptom, or excessive daytime sleepiness, preferably, a motor complication such as wearing-off phenomenon, on-off fluctuation, dyskinesia or the like, more preferably, a symptom such as wearing-off phenomenon, dyskinesia or the like.

As Parkinson's disease progresses, more dopamine cells die and the remaining cells cannot store sufficient dopamine to maintain its benefits in the L-DOPA and/or dopamine agonist therapy. As a result, the duration of action at each dose decreases and patients need higher or more frequent doses. After 2-5 years, as many as 50-75% of the patients experience fluctuations in their response to L-DOPA, for example, in length of on-time and the like. Along with the fluctuations, the patients develop wearing-off phenomenon, on-off fluctuation, dyskinesia (involuntary movement) or the like which accompany the fluctuations in the duration of action. Thus, continuation of the L-DOPA and/or dopamine agonist therapy may be difficult due to the onset of such side effects and the like. Therefore, the agent for the treatment and/or prophylaxis of a movement disorder of the present invention can extend the effective time of the treatment with L-DOPA and/or a dopamine agonist by reducing or suppressing the above-mentioned side effects. Particularly, the agent for the treatment and/or prophylaxis of a movement disorder of the present invention can effectively suppress the wearing-off phenomenon or the like, which are problematic in L-DOPA therapy of patients with Parkinson's disease in an advanced stage.

L-DOPA used for the above-mentioned L-DOPA and/or dopamine agonist therapy may contain L-DOPA or a salt, hydrate, prodrug or the like thereof as an active ingredient, and examples thereof include preparations containing these as an active ingredient and the like. Examples of the commercially available product include Menesit (registered trade mark), EC Doparl (registered trade mark), Doparl (registered trade mark), Madopar (registered trade mark) and the like. The dopamine agonist may contain a dopamine agonist or a salt, hydrate, prodrug or the like thereof as an active ingredient, and examples thereof include preparations containing pramipexole, talipexole, ropinirole, cabergoline, pergolide or the like, or a hydrochloride, mesylate or prodrug thereof or the like as an active ingredient, and the like. Examples of the commercially available product include Domin (registered trade mark), Permax (registered trade mark), Cabaser (registered trade mark) and the like.

The agent for the treatment and/or prophylaxis of Parkinson's disease of the present invention characteristically comprises a thiazole derivative or a pharmaceutically acceptable salt thereof and L-DOPA and/or a dopamine agonist in combination, and not only can reduce or suppress each symptom of Parkinson's disease, but also can delay the onset of the side effect caused by the administration of the aforementioned L-DOPA and/or a dopamine agonist (e.g., wearing-off phenomenon, on-off fluctuation, dyskinesia or the like) or suppress the symptoms.

In the following, the compound represented by the formula (I) is referred to as Compound (I). The compounds having other formula numbers are also referred to in the same manner.

The definition of each group in the formula (I) is as follows.

Examples of the lower alkyl moiety of the lower alkyl, the lower alkoxy and the lower alkanoyl include straight or branched alkyl having 1 to 10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the aralkyl include aralkyl having 7 to 16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of the aryl include aryl having 6 to 14 carbon atoms, and more specific examples thereof include phenyl, naphthyl, azulenyl, anthryl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic fused aromatic heterocyclic group in which 3 to 8-membered rings are fused, having at least one atom selected from a nitrogen atom, an oxygen atom, and a sulfur atom, and the like. More specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, furo[2,3-b]pyridyl, 6,7-dihydro-5H-cyclopenta[b]pyridyl, 7,8-dihydro-5H-pyrano[4,3-b]pyridyl, 7,8-dihydro-5H-thiopyrano[4,3-b]pyridyl and the like.

Examples of the aromatic heterocycle-alkyl include a group wherein an aromatic heterocyclic group is bonded to alkylene. The aromatic heterocyclic group include those exemplified in the above-mentioned aromatic heterocyclic group, and the alkylene include an alkylene having 1 to 10 carbon atoms, and specific examples thereof include methylene, ethylene, trimethylene, propylene, tetramethylene, pentamethylene, hexamethylene, heptamethylene, octamethylene, nonamethylene, decamethylene and the like. Specific examples of the aromatic heterocycle-alkyl include pyrrolylmethyl, pyrrolylethyl, thiazolylmethyl, pyridylmethyl, pyridylethyl, pyrimidinylmethyl, pyrimidinylethyl, indolylmethyl, benzimidazolylmethyl and the like.

Examples of the aliphatic heterocycle-alkyl include a group wherein the aliphatic heterocyclic group is bonded to alkylene. Examples of the aliphatic heterocyclic group include a 5-membered or 6-membered monocyclic aliphatic heterocyclic group containing at least one atom selected from a nitrogen atom, an oxygen atom and a sulfur atom, a bicyclic or tricyclic fused aliphatic heterocyclic group in which 3 to 8-membered rings are fused, having at least one atom selected from a nitrogen atom, an oxygen atom, and a sulfur atom, and the like. More specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, 5,6-dihydro-2H-pyridyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like. Examples of the alkylene include alkylene having 1 to 10 carbon atoms, and specific examples thereof include methylene, ethylene, trimethylene, propylene, tetramethylene, pentamethylene, hexamethylene, heptamethylene, octamethylene, nonamethylene, decamethylene and the like. Specific examples of the aliphatic heterocycle-alkyl include 5,6-dihydro-2H-pyridylmethyl, 5,6-dihydro-2H-pyridylethyl, tetrahydro-2H-pyranylmethyl, 5,6-dihydro-2H-pyranylmethyl, 5,6-dihydro-2H-pyranylethyl, morpholinomethyl, morpholinoethyl, piperazinylmethyl, oxazolidinylmethyl and the like.

The halogen means each atom of fluorine, chlorine, bromine and iodine.

Compound (I) or a pharmaceutically acceptable salt thereof of the present invention or used in the present invention is preferably a compound having a potent antagonistic activity against adenosine $A_{2A}$ receptors from among various subtypes of adenosine receptors (e.g., adenosine $A_1$, $A_{2A}$, $A_{2B}$ and $A_3$ receptors).

Accordingly, Compound (I) or a pharmaceutically acceptable salt thereof of the present invention or used in the present invention is preferably a compound having a strong affinity for the adenosine $A_{2A}$ receptors. For example, the compound is preferably one having an inhibitory activity of 50% or more at a test compound concentration of $3 \times 10^{-8}$ mol/L, more preferably one having an inhibitory activity of 50% or more at a test compound concentration of $1 \times 10^{-8}$ mol/L, still more preferably one having an inhibitory activity of 50% or more at a test compound concentration of $3 \times 10^{-9}$ mol/L, further preferably one having an inhibitory activity of 50% or more at a test compound concentration of $1 \times 10^{-9}$ mol/L, in the adenosine $A_{2A}$ receptor binding test shown in the below-mentioned Test Example 1. In addition, the compound is preferably one having an inhibitory activity of 30 nmol/L or less in an inhibitory constant (Ki value), more preferably one having an inhibitory activity of 10 nmol/L or less, still more preferably one having an inhibitory activity of 3 nmol/L or less, further preferably one having an inhibitory activity of 1 nmol/L or less.

Further, Compound (I) or a pharmaceutically acceptable salt thereof of the present invention or used in the present invention is preferably a compound having selective affinity for the adenosine $A_{2A}$ receptors from among various subtypes of the adenosine receptors. For example, a compound having a higher affinity for the adenosine $A_{2A}$ receptors than that for the adenosine $A_1$ receptors is preferable. Specifically, for example, the compound is preferably a compound having 5 times or more affinity, more preferably 10 times or more affinity, further preferably 50 times or more affinity, even more preferably 100 times or more affinity, most preferably 500 times or more affinity for the adenosine $A_{2A}$ receptors than that for the adenosine $A_1$ receptors.

The affinity for adenosine receptors can be determined according to a conventional method, for example, according to the method of Test Example 1 to be mentioned below, or the methods described in, for example, a document [for example, Naunyn Schmiedebergs Arch Pharmacol., 355(1), p. 59 (1987); Naunyn Schmiedebergs Arch Pharmacol. 355(2), p. 204 (1987); Br. J. Pharmacol. 117(8), p. 1645 (1996) and the like].

More specifically, Compound (I) is preferably a compound wherein $R^1$ is phenyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; pyridyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; pyrimidinyl optionally substituted by 1 to 3 substituents selected from halogen, $C_{1-6}$ alkyl optionally substituted by $C_{1-6}$ alkoxy or morpholino, $C_{1-6}$ alkanoyl, vinyl and $C_{1-6}$ alkoxy; 5,6-dihydro-2H-pyridylmethyl optionally substituted by 1 to 3 substituents selected from halogen, $C_{1-6}$ alkyl and $C_{1-6}$ alkoxy; 2,3,4,5-tetrahydropyranyloxy; pyrrolyl; indolyl; oxazolopyridyl; quinolyl; 1H-3,4-dihydropyranopyridinyl; 1H-3,4-dihydrothiopyranopyridinyl; cyclopentapyridyl; or pyridylmethyl, more preferably a compound wherein $R^1$ is phenyl optionally substituted by 1 to 3 substituents selected from a fluorine atom, a chlorine atom, methyl and methoxy; pyridyl optionally substituted by 1 to 3 substituents selected from a fluorine atom, a chlorine atom, methyl and methoxy; pyrimidinyl optionally substituted by 1 to 3 substituents selected from a fluorine atom, a chlorine atom, methyl and methoxy; 5,6-dihydro-2H-pyridylmethyl optionally substituted by 1 to 3 substituents selected from a fluorine atom, a chlorine atom, methyl and methoxy; or 2,3,4,5-tetrahydropyranyloxy, still more preferably a compound wherein $R^1$ is pyridyl substituted by 1 to 3 substituents selected from a chlorine atom, methyl and methoxy; pyrimidinyl substituted by 1 to 3 substituents selected from chlorine atom, methyl and methoxy; 5,6-dihydro-2H-pyridylmethyl; or 2,3,4,5-tetrahydropyranyloxy. More specifically, Compound (I) is preferably, for example, compounds of the following formulas (IA)-(IAA), and the like.

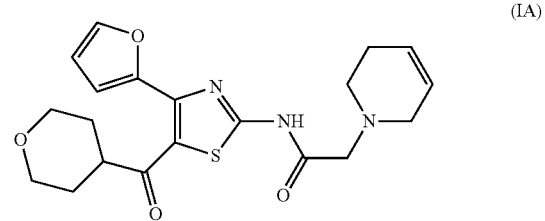

(IA)

(IB)
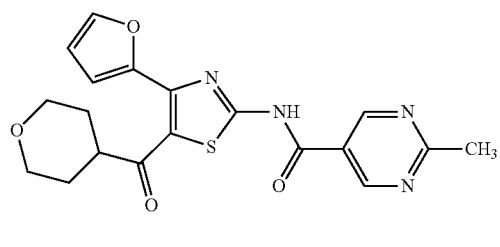
(IC)
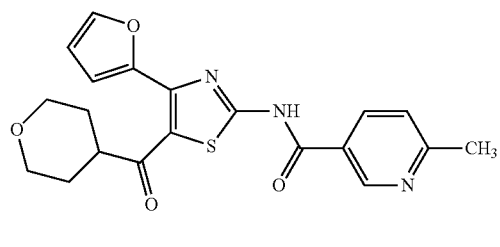
(ID)
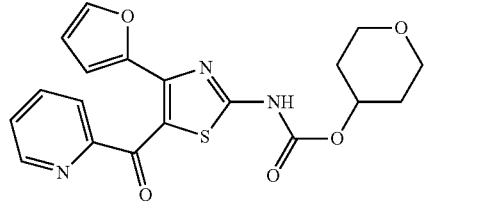
(IE)
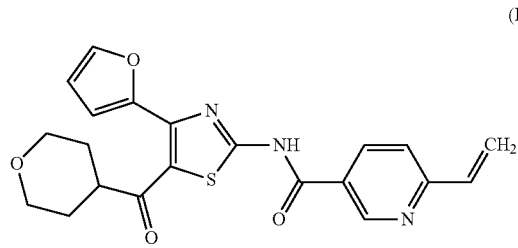
(IF)
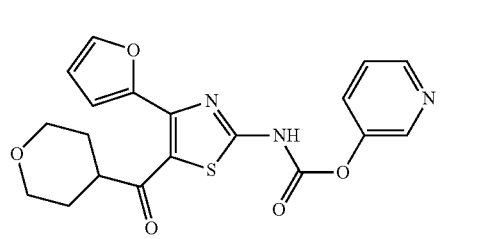
(IG)
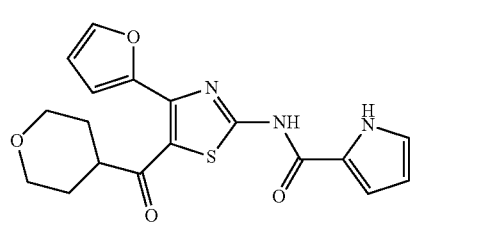
(IH)
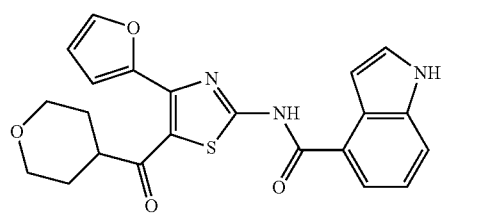
(II)
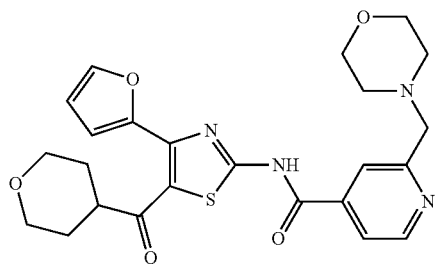
(IJ)
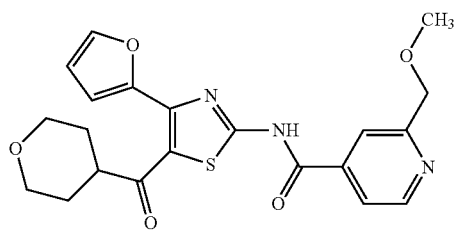
(IK)
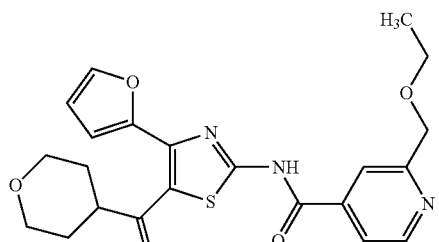
(IL)
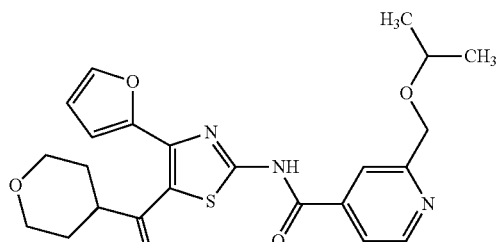
(IM)
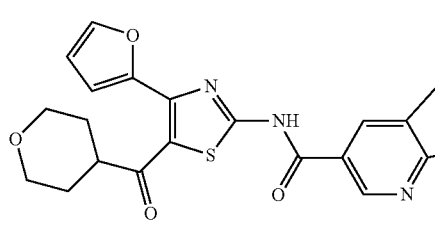
(IN)
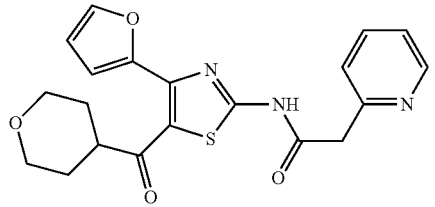

(IO) 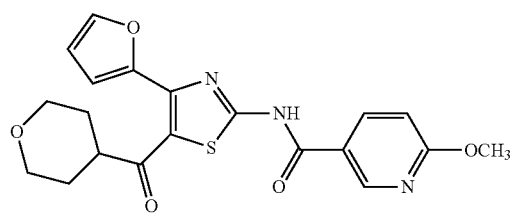
(IP) 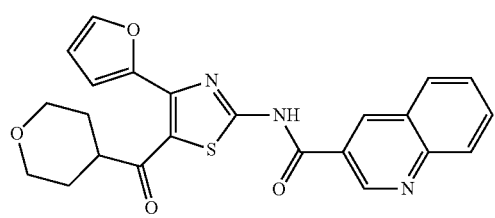
(IQ) 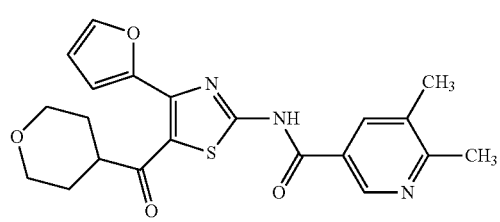
(IR) 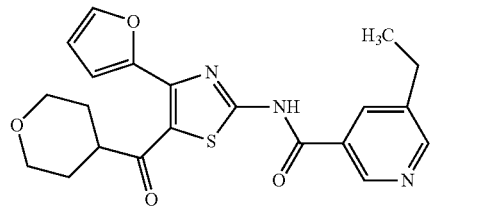
(IS) 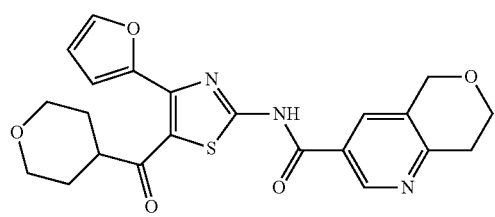
(IT) 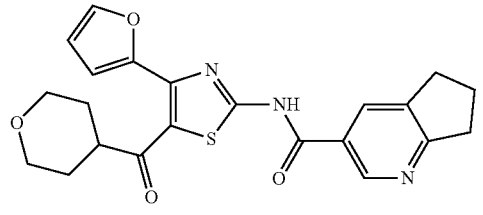
(IU) 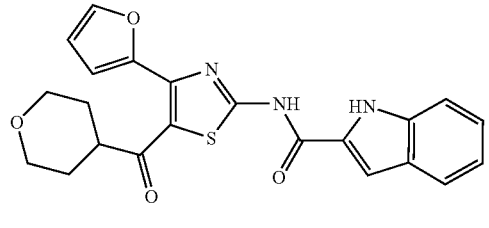

(IV) 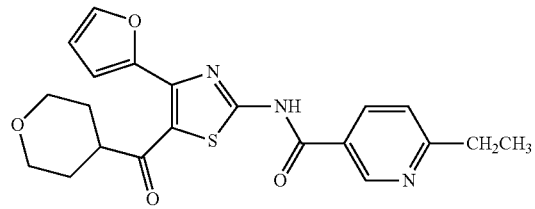
(IW) 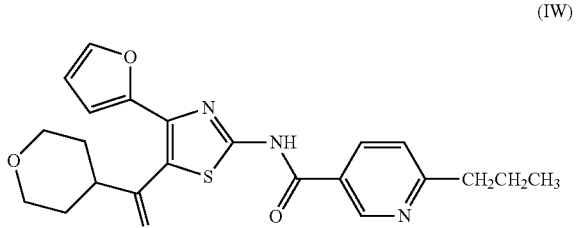
(IX) 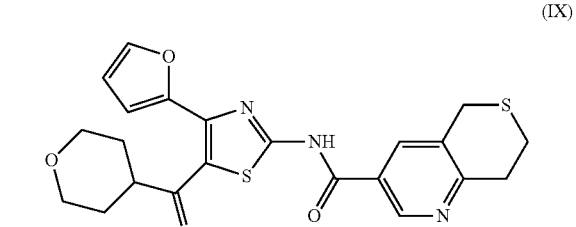
(IY) 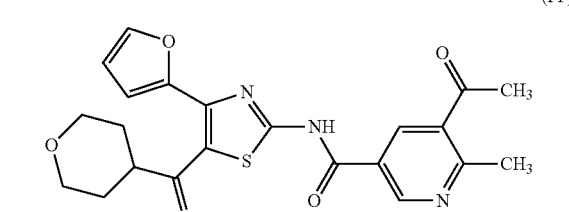
(IZ) 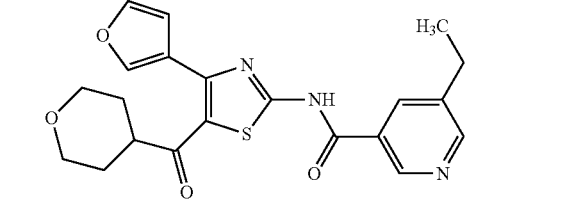
(IAA) 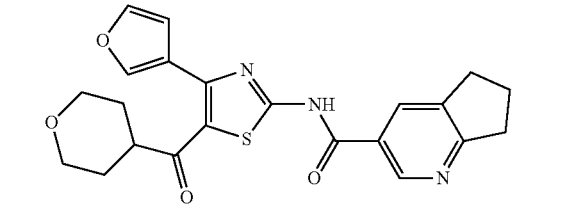

The pharmaceutically acceptable salts of Compound (I) include, for example, pharmaceutically acceptable acid addition salts, metal salts, ammonium salts, organic amine addition salts, amino acid addition salts, and the like. The pharmaceutically acceptable acid addition salts of Compound (I) include, for example, inorganic acid salts such as hydrochloride, hydrobromate, nitrate, sulfate, and phosphate; organic acid salts such as acetate, oxalate, maleate, fumarate, citrate, benzoate, and methane sulfonate, and the like. Examples of the pharmaceutically acceptable metal salts include alkali metal salts such as a sodium salt, and a potassium salt; alkaline earth metal salts such as a magnesium salt, and a calcium salt; an aluminum salt; a zinc salt, and the like. Examples of the pharmaceutically acceptable ammonium salts include salts of ammonium, tetramethylammonium, and the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

Compound (I) can be produced according to a known method, for example, the method described in WO 2005/063743 and the like.

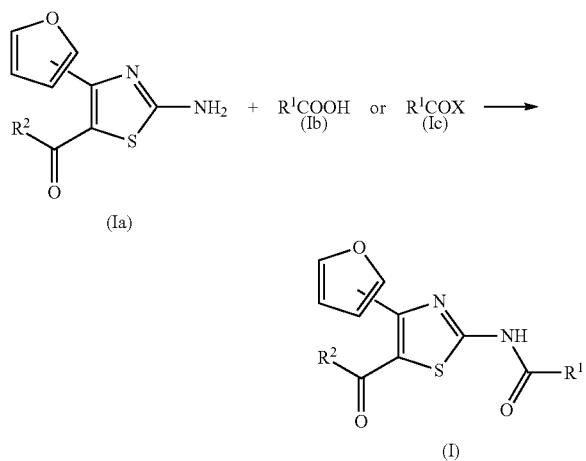

wherein $R^1$ and $R^2$ are as defined above, and X is a chlorine atom, a bromine atom or the like.

Specifically, as shown in the above-mentioned formula, Compound (I) can be produced, for example, by reacting compound (Ia) described in WO 2005/063743 with preferably 0.5 to 5 equivalents of compound (Ib) in a solvent such as methanol, dichloromethane, chloroform, toluene, ethyl acetate, acetonitrile, tetrahydrofuran (THF), N,N-dimethylformamide (DMF), N,N-dimethylacetamide (DMA), pyridine, water, or a mixed solvent thereof and the like, preferably in the presence of 1 to 5 equivalents of a condensing agent such as 1,3-dicyclohexanecarbodiimide (DCC), 1-ethyl-3-(3-dimethylaminopropyl)carbodiimide (EDC) hydrochloride and the like, if necessary, in the presence of preferably 1 to 5 equivalents of 1-hydroxybenzotriazole (HOBt) monohydrate, 4-dimethylaminopyridine (DMAP) and the like, at a temperature between −20° C. and the boiling point of the solvent used, for 5 min to 72 hr.

Alternatively, Compound (I) can also be produced, for example, by reacting compound (Ia) described in WO 2005/063743 with preferably 1 to 10 equivalents of compound (Ic) without solvent or in a solvent such as dichloromethane, chloroform, 1,2-dichloroethane, toluene, ethyl acetate, acetonitrile, THF, DMF, DMA, pyridine and the like, if necessary, in the presence of preferably 1 to 10 equivalents of a base such as potassium carbonate, triethylamine, 4-dimethylaminopyridine (DMAP) and the like, at a temperature between −20° C. and 150° C., for 5 min to 72 hr.

Compound (I) may exist as stereoisomers such as geometrical isomers or optical isomers, or tautomers. The thiazole derivative or a pharmaceutically acceptable salt thereof of the present invention encompasses all possible isomers including those and mixtures thereof. All possible isomers including those and mixtures thereof can be used for an agent for the treatment and/or prophylaxis of a movement disorder, a pharmaceutical composition, an agent for the treatment and/or prophylaxis of Parkinson's disease, a kit, a method for the treatment and/or prophylaxis of a movement disorder, a method for the treatment and/or prophylaxis of Parkinson's disease, a combination, use for the manufacture of an agent for the treatment and/or prophylaxis of a movement disorder and use for the manufacture of an agent for the treatment and/or prophylaxis of Parkinson's disease, of the present invention.

To obtain a salt of Compound (I), when the Compound (I) is obtained in the form of a salt, it may be purified as it is. Further, when the compound is obtained in a free form, the compound may be dissolved or suspended in a suitable solvent, followed by addition of an acid or a base to form a salt. Then, the resulting salt may be isolated and purified.

The Compound (I) or a pharmaceutically acceptable salt thereof may exist in the form of an adduct with water or various solvents. Such adduct is also encompassed in the thiazole derivative or a pharmaceutically acceptable salt thereof of the present invention, and can be used for an agent for the treatment and/or prophylaxis of a movement disorder, a pharmaceutical composition, an agent for the treatment and/or prophylaxis of Parkinson's disease, a kit, a method for the treatment and/or prophylaxis of a movement disorder, a method for the treatment and/or prophylaxis of Parkinson's disease, a combination, use for the manufacture of an agent for the treatment and/or prophylaxis of a movement disorder and use for the manufacture of an agent for the treatment and/or prophylaxis of Parkinson's disease, of the present invention.

L-DOPA used for a pharmaceutical composition, an agent for the treatment and/or prophylaxis of Parkinson's disease, a kit, a method for the treatment and/or prophylaxis of Parkinson's disease, a combination and use for the manufacture of an agent for the treatment and/or prophylaxis of Parkinson's disease, of the present invention may contain, as an active ingredient, L-DOPA or a salt, hydrate, prodrug or the like thereof and, for example, a preparation and the like containing these as active ingredients can be used. Such L-DOPA can be obtained, for example, as a commercially available product, or can be produced by a known method. Specific examples of the commercially available product include Menesit (registered trade mark), EC Doparl (registered trade mark), Doparl (registered trade mark), Madopar (registered trade mark) and the like.

The dopamine agonist used for a pharmaceutical composition, an agent for the treatment and/or prophylaxis of Parkinson's disease, a kit, a method for the treatment and/or prophylaxis of Parkinson's disease, a combination and use for the manufacture of an agent for the treatment and/or prophylaxis of Parkinson's disease, of the present invention may contain, as an active ingredient, a dopamine agonist or a salt, hydrate, prodrug or the like thereof and, for example, a preparation and the like containing these as active ingredients can be used. Specific examples thereof include pramipexole, talipexole, ropinirole, cabergoline, pergolide and the like, or a hydrochloride, mesylate, prodrug thereof and the like, and a preparation and the like containing these as active ingredients can also be used. Such dopamine agonist can be obtained, for example, as a commercially available product, or can be produced by a known method. Specific examples of the commercially available product include Domin (registered trade mark), Permax (registered trade mark), Cabaser (registered trade mark) and the like.

The pharmaceutical preparation according to an agent for the treatment and/or prophylaxis of a movement disorder, a method for the treatment and/or prophylaxis of a movement disorder and use for the manufacture of an agent for the treatment and/or prophylaxis of a movement disorder, of the present invention may contain, as the active ingredient, Compound (I) or a pharmaceutically acceptable salt thereof either alone or as a mixture with any other therapeutic active ingredient. Furthermore, these pharmaceutical preparations are prepared by mixing the active ingredient with one or more pharmaceutically acceptable carriers (for example, diluents, solvents, excipients, or the like), and then subjecting the mixture to any method well-known in the technical field of pharmaceutics.

As for the administration route, it is preferable to select the most effective route of administration for treatment. Examples of the administration route include oral administration, and parenteral administration, for example, such as intravenous or transdermal administration and the like.

Examples of the dosage form include tablets, injections, external preparations, and the like.

Suitable dosage forms for the oral administration, for example, tablets, can be prepared by using excipients such as lactose, disintegrators such as starch, lubricants such as magnesium stearate, or binders such as hydroxypropylcellulose, or the like.

Suitable dosage forms for the parenteral administration, for example, injections, can be prepared by using diluents or solvents such as a saline solution, a glucose solution, or a mixture of brine and glucose solution, or the like. A dosage form suitable for external preparation is not particularly limited and, for example, ointment, cream, liniment, lotion, cataplasm, plaster, tape and the like can be included. For example, ointment, cream and the like can be produced by, for example, dissolving or mixing-dispersing the active ingredient in a base such as white petrolatum and the like.

The dose and administration frequency of Compound (I) or a pharmaceutically acceptable salt thereof varies depending on the efficacy, dose and/or administration form, age and body weight of patients, properties or severity of the symptoms to be treated and the like. For general oral administration, 0.001-1000 mg, preferably 0.05-100 mg, is administered to one adult in one to several portions a day. For parenteral administration such as intravenous administration and the like, 0.001-1000 mg, preferably 0.01-100 mg, is generally administered to one adult in one to several portions a day. For transdermal administration, an external preparation containing 0.001-10% of Compound (I) or a pharmaceutically acceptable salt thereof is generally applied once to several times a day. However, these doses and administration frequencies vary depending on the aforementioned various conditions.

The agent for the treatment and/or prophylaxis of a movement disorder, the method of treating and/or preventing a movement disorder and the thiazole derivative or a pharmaceutically acceptable salt thereof for use in the treatment and/or prophylaxis of a movement disorder of the present invention shows a superior therapeutic and/or prophylactic, or reducing and/or suppressive effect on a movement disorder such as extrapyramidal syndrome, bradykinesia, gait disturbance, dystonia, dyskinesia, tardive dyskinesia or the like; and a side effect of L-DOPA and/or dopamine agonist therapy such as wearing-off phenomenon, on-off fluctuation, dyskinesia or the like. Particularly, it shows a superior therapeutic and/or prophylactic, or reducing and/or suppressive effect on the above-mentioned disease developed in Parkinson's disease in an advanced stage (e.g., a movement disorder such as extrapyramidal syndrome, bradykinesia, gait disturbance, dystonia, dyskinesia, tardive dyskinesia or the like; and a side effect of L-DOPA and/or dopamine agonist therapy such as wearing-off phenomenon, on-off fluctuation, dyskinesia or the like).

As mentioned above, Compound (I) or a pharmaceutically acceptable salt thereof may be used in combination with one or more other pharmaceutical components.

Examples of the other pharmaceutical components used in combination include known drugs useful as therapeutic and/or prophylactic drug for Parkinson's disease and the like, and the like, and the like (Iyaku (Medicine and Drug) Journal, vol. 44, p. 91 (2008)). Specifically, for example, COMT inhibitors (e.g., entacapone, tolcapone and the like), MAO inhibitors (e.g., selegiline, rasagiline and the like) and the like can be included.

When Compound (I) or a pharmaceutically acceptable salt thereof is used in combination with other pharmaceutical component(s), Compound (I) or a pharmaceutically acceptable salt thereof, and other pharmaceutical component(s) may be administered simultaneously or separately at an interval. The doses vary depending on the administration subject, the administration route, the disease, and the combinations of pharmaceutical component, and the like, and should be decided according to the doses used in the clinic.

(a) Compound (I) or a pharmaceutically acceptable salt thereof and (b) L-DOPA and/or a dopamine agonist used for the pharmaceutical composition, the agent for the treatment and/or prophylaxis of Parkinson's disease, the kit, the method for the treatment and/or prophylaxis of Parkinson's disease, the combination and the use for the manufacture of an agent for the treatment and/or prophylaxis of Parkinson's disease, of the present invention may be used or administered as a single preparation (combination agent) or as a combination of more than one preparation, provided that these preparations are formulated together with, for example, a pharmaceutically acceptable carrier to contain these active ingredients. In particular, a combination of two or more preparations is preferred. When used or administered as a combination of more than one preparation, the preparations may be used or administered simultaneously or separately at an interval. Preferably, these preparations are used in the form of, for example, tablets, injections, external preparations or the like.

The dose ratio (weight/weight) of (a) Compound (I) or a pharmaceutically acceptable salt thereof and (b) L-DOPA and/or a dopamine agonist can be appropriately adjusted according to a combination of (a) Compound (I) or a pharmaceutically acceptable salt thereof and (b) L-DOPA and/or a dopamine agonist used, efficacy of each of (a) Compound (I) or a pharmaceutically acceptable salt thereof and (b) L-DOPA and/or a dopamine agonist and the like. Specifically for example, it is 1/100000 ((a) Compound (I) or a pharmaceutically acceptable salt thereof/(b) L-DOPA and/or a dopamine agonist)-1000/1, preferably 1/50000-500/1, more preferably 1/6000-100/1, further more preferably 1/4000-15/1, still further more preferably 1/1000-10/1, most preferably 1/100-10/1.

These preparations are prepared by mixing the active ingredient with one or more pharmaceutically acceptable carriers (for example, diluents, solvents, excipients, or the like), and then subjecting the mixture to any method well known in the technical field of pharmaceutics.

Suitable dosage forms for the oral administration, for example, tablets, can be prepared by using excipients such as lactose, disintegrators such as starch, lubricants such as magnesium stearate, binders such as hydroxypropylcellulose, or the like.

Suitable dosage forms for the parenteral administration, for example, injections, can be prepared by using diluents or solvents such as a saline solution, a glucose solution, or a mixture of brine and glucose solution, or the like. A dosage form suitable for external preparation is not particularly limited to and, for example, ointment, cream, liniment, lotion, cataplasm, plaster, tape and the like can be included. For example, ointment, cream and the like can be produced by, for example, dissolving or mixing-dispersing the active ingredient in a base such as white petrolatum and the like.

When administered as a combination of more than one preparation, for example, (a) a first component comprising Compound (I) or a pharmaceutically acceptable salt thereof, and (b) a second component comprising L-DOPA and/or a dopamine agonist may be separately prepared into a kit, and may be administered to the same subject in the same route or in different routes simultaneously or separately at an interval, using the kit.

As the kit, for example, a kit comprising contents and two or more containers (for example, vials, bags, etc.) whose material, shape, and so on are not particularly limited as long as the containers do not cause degeneration of the components which are the contents due to external temperature or light nor cause elution of chemical components from the containers during storage, and having a form which enables the administration of the above first and second components which are the contents through separate routes (for example, tubes, etc.) or the same route is used. Specific examples thereof include tablet kits, injection kits, and the like.

When (a) Compound (I) or a pharmaceutically acceptable salt thereof and (b) L-DOPA and/or a dopamine agonist are used or administered as a combination of plural preparations for the above-mentioned objects, the dose and administration frequency vary depending on the efficacy of each active ingredient, dosage form, age and body weight of a patient, symptom, and the like. It is preferable to administer each of (a) Compound (I) or a pharmaceutically acceptable salt thereof and (b) L-DOPA and/or a dopamine agonist usually at the following dose per day.

For oral administration as, for example, tablet, (a) Compound (I) or a pharmaceutically acceptable salt thereof and (b) L-DOPA and/or a dopamine agonist are administered at 0.1-1000 mg and 0.1-10000 mg, preferably 0.1-500 mg and 0.1-5000 mg, more preferably 0.5-500 mg and 1-3000 mg, still more preferably 0.5-300 mg and 1-2000 mg, respectively, per one adult simultaneously or separately at an interval in one to several portions a day usually.

For parenteral administration as, for example, injection and the like, (a) Compound (I) or a pharmaceutically acceptable salt thereof and (b) L-DOPA and/or a dopamine agonist are administered at 0.1-1000 mg and 0.1-10000 mg, preferably 0.1-500 mg and 0.1-5000 mg, more preferably 0.5-500 mg and 1-3000 mg, still more preferably 0.5-300 mg and 1-2000 mg, respectively, per one adult simultaneously or separately at an interval in one to several portions a day usually.

When (a) Compound (I) or a pharmaceutically acceptable salt thereof and (b) L-DOPA and/or a dopamine agonist are used or administered as a single preparation for the above-mentioned objects, the dose and administration frequency vary depending on the efficacy of each active ingredient, dosage form, age and body weight of a patient, symptom, and the like. It is preferable to prepare one preparation containing each dose in the use or administration of a combination of the above-mentioned plural preparations, and use or administer same.

However, such dose and administration frequency vary depending on the aforementioned various conditions.

A pharmaceutical composition, an agent for the treatment and/or prophylaxis of Parkinson's disease, a kit, a method for the treatment and/or prophylaxis of Parkinson's disease, and a combination of the present invention can be used for, for example, the treatment and/or prophylaxis of Parkinson's disease, more specifically, for patients, for example, patients with Parkinson's disease in an advanced stage, patients with Parkinson's disease who developed symptoms of on-off fluctuation, wearing-off phenomenon, dyskinesia or the like due to L-DOPA therapy or the like, and the like, and can effectively treat these diseases.

Next, the therapeutic effect of Compound (I) or a pharmaceutically acceptable salt thereof on movement disorders, the effect of combined administration of (a) Compound (I) or a pharmaceutically acceptable salt thereof and (b) L-DOPA and/or a dopamine agonist and the like are specifically explained in the following Test Examples.

Test Example 1 Adenosine Receptor Binding Action (1) Adenosine $A_{2A}$ Receptor Binding Test The test can be performed according to, for example, the method of Varani et al. (British Journal of Pharmacology, 1996, 117, p. 1693).

Specifically, for example, human recombinant receptors are expressed in HEK-293 cells. The cell membranes of the receptor-expressing cells are collected, and a cell membrane suspension is prepared. After dilution with tris(hydroxymethyl)-aminomethane hydrochloride (Tris HCl) buffer, tritium-labeled CGS-21680 ($^3$H-2-[p-(2-carboxyethyl)phenethylamino]-5'-(N-ethylcarboxamido)adenosine: 50 mmol/L) and a test compound solution (dimethyl sulfoxide solution of the test compound) are added to the cell membrane suspension for binding to the receptors. After the reaction, the mixture is subjected to rapid suction filtration using glass-fiber filter paper, and the radioactivity of the glass-fiber filter paper is measured. In this way, the inhibitory rate of the test compound for the human adenosine $A_{2A}$ receptor binding ($^3$H-CGS21680 binding) can be determined.

The test can also be performed according to the method of Bruns et al. (Molecular Pharmacology, Vol. 29, p. 331, 1986).

Specifically, for example, rat striatum is suspended in 50 mL of ice-cooled Tris HCl buffer (50 mmol/L, pH 7.7) using a Polytron homogenizer and the suspension is centrifuged. The resulting precipitate is resuspended by adding Tris HCl buffer (50 mmol/L) thereto, followed by centrifugation in the same manner. The resulting final precipitate is suspended in Tris HCl buffer (50 mmol/L) [containing magnesium chloride (10 mmol/L), and adenosine deaminase (0.02 units/mg tissue)] to prepare the suspension at the tissue concentration of 5 mg (wet weight)/mL. Tritium-labeled CGS-21680 (final concentration of 6.0 mmol/L), and the test compound solution (dimethylsulfoxide solution of test compound diluted with Tris HCl buffer) are added. The mixture is allowed to stand at 25° C. for 120 minutes, followed by rapid suction filtration using glass-fiber filter paper, and then immediately washed with ice-cooled Tris HCl buffer (50 mmol/L). The glass-fiber filter paper is then placed in a vial, and MicroScinti (PKI) is added. Then, the radioactivity is measured with a TopCount (PerkinElmer), whereby the inhibitory rate for rat adenosine $A_{2A}$ receptor binding ($^3$H-CGS21680 binding) of the test compound can be determined.

The inhibitory rate can be calculated by the following equation.

$$\text{Inhibitory rate}(\%) = \left(1 - \frac{\text{Amount of binding in the presence of drug} - \text{amount of non-specific binding}}{\text{Total amount of binding} - \text{amount of non-specific binding}}\right) \times 100$$

In the equation, the total amount of binding refers to the bound radioactivity of $^3$H-CGS21680 in the absence of the test compound. The amount of non-specific binding refers to the bound radioactivity of $^3$H-CGS21680 in the presence of 50 µmol/L of 5'-N-ethylcarboxamideadenosine (NECA) or 100 µmol/L of cyclopentyladenosine (CPA). The amount of binding in the presence of drug refers to the bound radioactivity of $^3$H-CGS21680 in the presence of the test compound.

In the above test, the inhibitory rate for the adenosine $A_{2A}$ receptor at different concentrations of the test compound or a pharmaceutically acceptable salt thereof, and the test compound concentration at which the test compound inhibits binding by 50% ($IC_{50}$) can be calculated by appropriately adjusting the concentration of the test compound.

The inhibition constant (Ki value) of the test compound for the adenosine $A_{2A}$ receptor binding can be calculated according to the following equation.

$$Ki = IC_{50}/(1+L/Kd)$$

In the equation, L denotes the concentration of the $^3$H-CGS21680 used in the test, and Kd is the dissociation constant of the $^3$H-CGS21680 used in the test.

Instead of $^3$H-CGS21680, $^3$H-SCH58261 ($^3$H-5-amino-7-(2-phenylethyl)-2-(2-furyl)pyrazolo[4,3-e]-1,2,4-triazolo[1,5-c]pyrimidine) and the like may be used.

(2) Adenosine $A_1$ Receptor Binding Test

The inhibition constant (Ki value) of the test compound for the adenosine $A_1$ receptor can be calculated in the same manner as in (1), using the materials below.

Specifically, for example, human $A_1$ receptor-expressing CHO cell membranes are used, and, as the labeled compound, for example, tritium-labeled DPCPX (1,3-dipropyl-8-cyclopentylxanthine) is used. The amount of non-specific binding can be determined by measuring the $^3$H-DPCPX bound radioactivity in the presence of, for example, 100 µmol/L of R(-)-PIA((-)-N$^6$-2-phenylisopropyl adenosine). The affinity of the test compound for the human adenosine $A_1$ receptors can be confirmed in this manner.

Alternatively, for example, rat $A_1$ receptor-expressing cell membrane (PerkinElmer) is used, and as the labeled compound, for example, tritium-labeled CHA (N$^6$-cyclohexyladenosine) is used. For the measurement of the amount of non-specific binding, $^3$H-CHA bound radioactivity is measured in the presence of, for example, 10 µmol/L of DPCPX, and the affinity of the test compound for the rat adenosine $A_1$ receptor can be confirmed.

By the foregoing tests (1) and (2), the selective affinities of the thiazole derivative or a pharmaceutically acceptable salt thereof used in the present invention for the adenosine $A_{2A}$ receptor can be confirmed.

(3) Affinity of Compound (I) or a Pharmaceutically Acceptable Salt Thereof for Adenosine Receptors Some of the examples of the affinities of Compound (I) or a pharmaceutically acceptable salt thereof for the adenosine $A_1$ receptor and the adenosine $A_{2A}$ receptor are presented below. Note that the test results below are those measured by MDS Pharma Services Inc. according to the foregoing methods.

TABLE 1

The affinities for adenosine receptors

| compound No. | Inhibitory rate for human adenosine $A_{2A}$ receptor binding ($^3$H-CGS21680 binding)* | Inhibitory rate for human adenosine $A_1$ receptor binding ($^3$H-DPCPX binding)* |
|---|---|---|
| (IA) | 92% | 14% |
| (IB) | 98% | 4% |
| (IC) | 88% | 29% |
| (ID) | 100% | 28% |

*Inhibitory rate at compound of 100 nmol/L

Test Example 2 Adenosine Receptor Binding Activity (2)

In the same manner as in the above-mentioned Test Example 1, the affinity of compound (IE)-(IAA) for adenosine receptor was confirmed (test results were those measured by Ricerca Biosciences, LLC according to the foregoing methods).

TABLE 2

The affinities for adenosine receptors

| compound No. | Inhibitory rate for human adenosine $A_{2A}$ receptor binding ($^3$H-CGS21680 binding)* | Inhibitory rate for human adenosine $A_1$ receptor binding ($^3$H-DPCPX binding)* | compound No. | Inhibitory rate for human adenosine $A_{2A}$ receptor binding ($^3$H-CGS21680 binding)* | Inhibitory rate for human adenosine $A_1$ receptor binding ($^3$H-DPCPX binding)* |
|---|---|---|---|---|---|
| (IE) | 93% | 33% | (IF) | 107% | 50% |
| (IG) | 102% | 91% | (IH) | 98% | 67% |
| (II) | 85% | 19% | (IJ) | 93% | 21% |
| (IK) | 92% | 24% | (IL) | 85% | 20% |
| (IM) | 98% | 47% | (IN) | 93% | 21% |
| (IO) | 97% | 56% | (IP) | 98% | 18% |

TABLE 2-continued

The affinities for adenosine receptors

| compound No. | Inhibitory rate for human adenosine $A_{2A}$ receptor binding ($^3$H-CGS21680 binding)* | Inhibitory rate for human adenosine $A_1$ receptor binding ($^3$H-DPCPX binding)* | compound No. | Inhibitory rate for human adenosine $A_{2A}$ receptor binding ($^3$H-CGS21680 binding)* | Inhibitory rate for human adenosine $A_1$ receptor binding ($^3$H-DPCPX binding)* |
|---|---|---|---|---|---|
| (IQ) | 100% | 18% | (IR) | 107% | 30% |
| (IS) | 90% | 10% | (IT) | 91% | 37% |
| (IU) | 110% | 36% | (IV) | 98% | 23% |
| (IW) | 98% | 23% | (IX) | 101% | 18% |
| (IY) | 97% | 8% | (IZ) | 102% | 21% |
| (IAA) | 98% | 9% | | | |

*Inhibitory rate at compound of 100 nmol/L

From the above tests, it is confirmed that Compound (I) shows selective affinity for the adenosine $A_{2A}$ receptor. Test Example 3 Therapeutic effect of combination of L-DOPA and the thiazole derivative of the present invention or a pharmaceutically acceptable salt thereof on common marmoset that developed Parkinson's disease symptom by treatment with 1-methyl-4-phenyl-1,2,3,6-tetrahydropyridine (MPTP)

Parkinson's disease is a disease based on the progressive degeneration and loss of dopaminergic neuron in substantia nigra-striatum. In primates, a treatment with MPTP, which is a dopamine neurotoxin, causes selective degeneration and loss of dopaminergic neuron in substantia nigra-striatum and induces symptoms of akinesia, muscle rigidity and the like. The primates treated with MPTP are known as the model of Parkinson's disease [Proceedings of the National Academy of Science USA, vol. 80, p. 4546 (1983)]. In addition, common marmoset belongs to Haplorhini and is known to show the symptoms of Parkinson's disease by MPTP, like other Haplorhini [Neuroscience Letter, vol. 57, p. 37 (1985)]. 2 mg/kg of MPTP (Sigma-Aldrich Co. Ltd.) was subcutaneously administered to the back of common marmoset (CLEA Japan, Inc.) once a day for 5 days, and 1-2 mg/kg of MPTP was additionally administered subcutaneously once or twice to the back about 3 weeks after first administration to prepare common marmoset exhibited chronic parkinsonian symptoms (lower locomotor activity, bradykinesia, gait disturbance, abnormal postures, a less coordinated movements, decreased vocalization and the like) (MPTP-treated marmoset), and the marmoset was used for the test. The parkinsonian symptoms were judged using the index described in a previous report [Annales of Neurology, vol. 43, p. 507 (1998)]. The observation items and scores are shown in Table 2. All compounds were used as a suspension in 0.5% MC400, 10% aqueous sucrose solution. The subject animal was placed in an observation cage (with locomotor activity measuring apparatus) one day before the test compound administration for preconditioning to the environment. The symptoms of Parkinson's disease were continuously monitored through one-way mirror and disability score was scored each 10 min for 6 hr.

TABLE 3

Disability Rating Scale Used in Common Marmoset

| | score | | | | |
|---|---|---|---|---|---|
| Items | 0 | 1 | 2 | 3 | 4 |
| Alertness | Normal | Reduced | Sleepy | — | — |
| Checking Movement | Present | Reduced | Absent | — | — |
| Attention Blinking | Normal | Abnormal | — | — | — |
| Posture | Normal | | abnormality of trunk, upper limb, lower limb, tail: each 1 point | | Grossly Abnormal |
| Balance/ Coordination | Normal | Impaired | Unstable | Falls | — |
| Reaction to stimuli | Normal | Reduced | Slow | Absent | — |
| Vocalization | Normal | Reduced | Absent | — | — |

Figure 2:
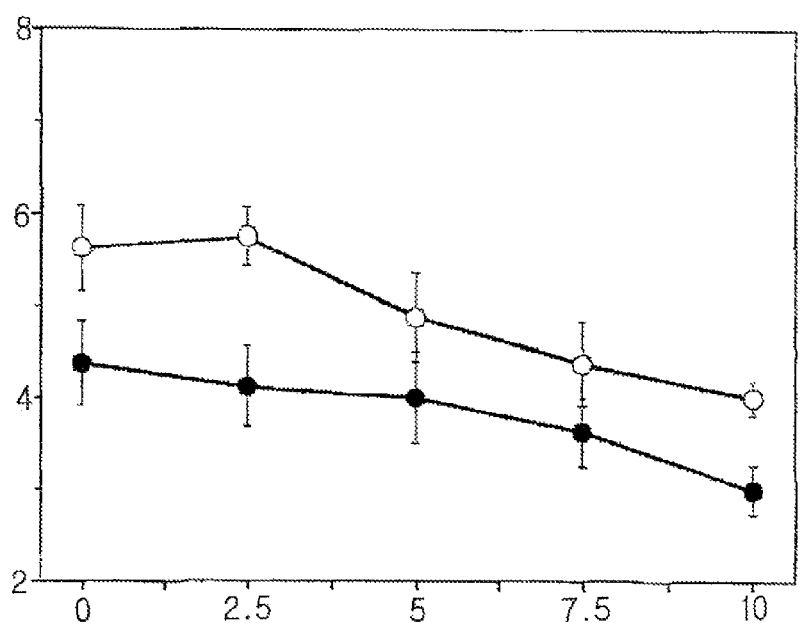
FIG. 2 shows the effect of compound (IC) on the maximum action (minimum motor disability score) in the Test Example 3. The vertical axis shows the minimum motor disability score, and the horizontal axis shows the L-DOPA dosage. ○ shows a combination of solvent and L-DOPA, and ● shows a combination of compound (IC) and L-DOPA.

The locomotor activity was automatically measured using a computer by a measuring apparatus with a photocell. When 2.5, 5.0, 7.5 and 10.0 mg/kg of L-DOPA (each containing ¼ amount of dopa decarboxylase inhibitor (benserazide hydrochloride)) were each administered, the parkinsonian symptoms in MPTP-treated marmoset decreased within increasement of the dosage. 1 mg/kg of compound (IC) and L-DOPA were simultaneously administered orally. Co-administration of compound (IC) (1 mg/kg) with the various doses of L-DOPA (2.5, 5.0, 7.5 and 10.0 mg/kg: each containing ¼ amount of benserazide hydrochloride) prolonged the anti-parkinsonian activity of L-DOPA, and also enhanced maximum effects of L-DOPA alone. The time course of influence on motor disability score when 1 mg/kg of compound (IC) and 10 mg/kg of L-DOPA were simultaneously administered orally in combination is shown in FIG. 1. When 1 mg/kg of compound (IC) and 10 mg/kg of L-DOPA were simultaneously administered orally in combination, the action expression time (on-time) increased as compared to the treatment with 10 mg/kg of L-DOPA alone. In addition, the maximum improvement values of motor disability score when 1 mg/kg of compound (IC) and each dose of L-DOPA (2.5, 5.0, 7.5 and 10.0 mg/kg: each containing ¼ amount of benserazide hydrochloride) were simultaneously administered orally in combination, and when treated with L-DOPA alone are shown in FIG. 2. When 1 mg/kg of compound (IC) and each dose of L-DOPA were simultaneously administered orally in combination, the intensity of the maximum improving maximum effects by each dose of L-DOPA was enhanced.

From the above-mentioned test, Compound (I) is considered to have effects of enhancing the therapeutic effect of L-DOPA on Parkinson's disease and prolonging the duration of therapeutic effect of L-DOPA on Parkinson's disease. Test Example 4 Therapeutic effect of combination of L-DOPA and the thiazole derivative or a pharmaceutically acceptable salt thereof of the present invention in MPTP-treated common marmoset that developed motor complication 10 mg/kg of L-DOPA (containing 2.5 mg/kg of benserazide hydrochloride) was administered by gavage to common marmoset that developed chronic parkinsonian symptoms by treatment with MPTP by the method described in Test Example 3 (MPTP-treated marmoset) twice a day at about 6 hr intervals. L-DOPA was repeatedly administered for more than 3 weeks to induction of motor complication (dyskinesia symptom, wearing-off phenomenon, on-off fluctuation and the like) in MPTP-treated marmoset in addition to parkinsonian symptoms, and the marmoset was used for the test. The parkinsonian symptoms were judged using rating scale described in a previous report [Annales of Neurology, vol. 43, p. 507 (1998)] as in Test Example 2. The locomotor activity was automatically measured using a computer by a measuring apparatus with a photocell. All compounds were used as a suspension in 0.5% MC400, 10% aqueous sucrose solution. The subject animal was placed in an observation cage (with locomotor activity measuring apparatus) one day before the test compound administration for preconditioning to the environment. The symptoms of Parkinson's disease were continuously monitored through one-way mirror and disability score was scored each 10 min for 6 hr. When 2.5 mg/kg or 10 mg/kg of L-DOPA (containing 2.5 or 0.625 mg/kg of benserazide hydrochloride) was administered, the parkinsonian symptoms in MPTP-treated marmoset decreased with the increasement of dosage. 1 mg/kg of compound (IC) and 2.5 mg/kg of L-DOPA were simultaneously administered in combination by gavage. As a result, extension of duration (on-time) of an anti-parkinsonian activities of L-DOPA (about 50 min by treatment with L-DOPA 2.5 mg/kg alone, about 150 min by combined administration of 1 mg/kg of compound (IC)), and enhanced the potency (minimum disability score 5.33±0.80 by treatment with L-DOPA 2.5 mg/kg alone, 3.83±0.17 by combined administration of 1 mg/kg of compound (IC)) were observed.

From the results of the above-mentioned Test Example 4, Compound (I) is considered to have an effect of suppressing wearing-off phenomenon, which is the side effect of L-DOPA. Test Example 5 Influence of combination of L-DOPA and the thiazole derivative or a pharmaceutically acceptable salt thereof of the present invention on dyskinesia in MPTP-treated common marmoset that developed motor complication 10 mg/kg of L-DOPA (containing 2.5 mg/kg of benserazide hydrochloride) was administered to common marmoset that developed chronic parkinsonian symptoms by treatment with MPTP by the method described in Test Example 3 (MPTP-treated marmoset) twice a day at about 6 hr intervals. L-DOPA was repeatedly administered for more than 3 weeks to induction of motor complication (dyskinesia symptom, wearing-off phenomenon, on-off fluctuation and the like) in MPTP-treated marmoset in addition to parkinsonian symptoms, and the marmoset was used for the test. The dyskinesia severity was rating using the rating scale described in a previous report [Annales of Neurology, vol. 43, p. 507 (1998)] as in Test Example 2. The evaluation items and scores are shown in Table 3. All compounds were used as a suspension of 0.5% MC400, 10% aqueous sucrose solution. The subject animal was placed in an observation cage (with locomotor activity measuring apparatus) one day before the test compound administration for preconditioning to the environment. The dyskinesia symptoms were observed through one-way mirror and scored each 20 min for 6 hr.

TABLE 4

Dyskinesia Rating Scale Used in Common Marmoset

| evaluation item | | score |
|---|---|---|
| Dyskinesia | absent | 0 |
| Fleeting and rare dyskinetic postures | mild | 1 |
| More prominent abnormal movements, but not interfering significantly with normal behavior | moderate | 2 |
| Continuous appearance of abnormal behavior to influence normal movement | marked | 3 |
| Mostly occupied by abnormal behavior, and no normal animal movement | severe | 4 |

The locomotor activity was automatically measured using a computer by a measuring apparatus with a photocell. When 1.25, 2.5, 5.0, 7.5 and 10 mg/kg of L-DOPA (each containing 0.3125, 0.625, 1.25, 1.875 and 2.5 mg/kg of benserazide hydrochloride, respectively) were each administered, dyskinesia was induced in MPTP-treated marmoset with increasing dose of L-DOPA. A combination of 1 mg/kg of compound (IC) and L-DOPA was simultaneously administered orally. Combined administration of 1 mg/kg of compound (IC) with the each doses of L-DOPA (1.25, 2.5, 5.0, 7.5 and 10.0 mg/kg: each containing ¼ amount of benserazide hydrochloride) did not exacerbate dyskinesia severity problematic for administration of each dose of L-DOPA alone. When compound (IC) alone was administered from 0.1 to 10 mg/kg, dyskinesia was not induced.

From the above-mentioned test, it was considered that Compound (I) does not exacerbate dyskinesia which is a side effect of L-DOPA. From the results of Test Examples 3-5, it was considered that a combined use of L-DOPA and a thiazole derivative such as Compound (I) and the like does not exacerbate dyskinesia which is a side effect of L-DOPA, but enhance a therapeutic effect of L-DOPA on Parkinson's disease (enhancement and prolongation of effect of L-DOPA).

From the aforementioned Test Examples 3-5, administration of Compound (I) or a pharmaceutically acceptable salt thereof is considered to suppress or reduce side effects (e.g., wearing-off phenomenon, on-off fluctuation, dyskinesia or the like) of L-DOPA and/or dopamine agonist therapy for Parkinson's disease or the like. Particularly, Compound (I) or a pharmaceutically acceptable salt thereof is considered to be effective for the reducing wearing-off phenomenon in L-DOPA and/or dopamine agonist therapy.

Moreover, a combined use of Compound (I) or a pharmaceutically acceptable salt thereof and L-DOPA is considered to effectively treat parkinsonian symptoms (movement disorders relating to bradykinesia, gait, akinesia, or the like). Moreover, when Compound (I) or a pharmaceutically acceptable salt thereof is used in combination with L-DOPA, an improving effect on parkinsonian symptoms and locomotor activity becomes stronger than that by the use of L-DOPA alone. Thus, a combined use of Compound (I) or a pharmaceutically acceptable salt thereof and L-DOPA can reduce the dose of L-DOPA necessary for achieving the same improvement level as a treatment with L-DOPA alone, and can suppress or delay expression of side effects in the circulatory and gastrointestinal systems, as well as the onset of dyskinesia and motor complication due to L-DOPA.

The following more specifically describes the present invention by way of Examples. It should be noted, however, that the scope of the present invention is not limited by the following Examples.

Example 1

Tablets having the following formulations are prepared according to the conventional manner. Compound (IA) (40 g), lactose (286.8 g), and potato starch (60 g) are mixed, and then a 10% aqueous solution of hydroxypropylcellulose (120 g) is added thereto. The resulting mixture is kneaded according to the conventional manner, granulated, and dried to form granules for tableting. After adding thereto 1.2 g of magnesium stearate followed by mixing, the mixture is punched with a tableting machine having a punch measuring 8 mm in diameter (Model RT-15; Kikusui) to obtain tablets (containing 20 mg of an active ingredient per tablet).

TABLE 5

| Formulation | |
| --- | --- |
| Compound (IA) | 20 mg |
| lactose | 143.4 mg |
| potato starch | 30 mg |
| hydroxypropylcellulose | 6 mg |
| magnesium stearate | 0.6 mg |
| | 200 mg |

Example 2

Tablets having the following formulation are prepared in the same manner as in Example 1.

TABLE 6

| Formulation | |
| --- | --- |
| Compound (IB) | 20 mg |
| lactose | 143.4 mg |
| potato starch | 30 mg |
| hydroxypropylcellulose | 6 mg |
| magnesium stearate | 0.6 mg |
| | 200 mg |

Example 3

Tablets having the following formulation are prepared in the same manner as in Example 1.

TABLE 7

| Formulation | |
| --- | --- |
| Compound (IC) | 20 mg |
| lactose | 143.4 mg |
| potato starch | 30 mg |
| hydroxypropylcellulose | 6 mg |
| magnesium stearate | 0.6 mg |
| | 200 mg |

Example 4

Tablets having the following formulation are prepared according to the conventional manner. Compound (IA) (40 g), L-DOPA (40 g), lactose (246.8 g), and potato starch (60 g) are mixed, and then a 10% aqueous solution of hydroxypropylcellulose (120 g) is added thereto. The resulting mixture is kneaded according to the conventional manner, granulated, and dried to form granules for tableting. After adding thereto 1.2 g of magnesium stearate followed by mixing, the mixture is punched with a tableting machine having a punch measuring 8 mm in diameter (Model RT-15; Kikusui) to obtain tablets (containing compound (IA) (20 mg) and L-DOPA (20 mg) per tablet).

TABLE 8

| Formulation | |
| --- | --- |
| Compound (IA) | 20 mg |
| L-DOPA | 20 mg |
| lactose | 123.4 mg |
| potato starch | 30 mg |
| hydroxypropylcellulose | 6 mg |
| magnesium stearate | 0.6 mg |
| | 200 mg |

Example 5

Tablets having the following formulation are prepared in the same manner as in Example 4.

TABLE 9

| Formulation | |
| --- | --- |
| Compound (IB) | 20 mg |
| L-DOPA | 20 mg |
| lactose | 123.4 mg |
| potato starch | 30 mg |
| hydroxypropylcellulose | 6 mg |
| magnesium stearate | 0.6 mg |
| | 200 mg |

Example 6

Tablets having the following formulation are prepared in the same manner as in Example 4.

TABLE 10

| Formulation | |
| --- | --- |
| Compound (IC) | 20 mg |
| L-DOPA | 20 mg |
| lactose | 123.4 mg |
| potato starch | 30 mg |
| hydroxypropylcellulose | 6 mg |
| magnesium stearate | 0.6 mg |
| | 200 mg |

Example 7

Injections having the following formulation are prepared according to the conventional manner. Compound (IA) (1 g) is added to distilled water for injection followed by mixing.

After adjusting the pH of the mixture to 7 by adding hydrochloric acid and a sodium hydroxide aqueous solution thereto, the total volume is adjusted to 1,000 mL with distilled water for injection. The resulting mixture is aseptically charged into glass vials in 2-mL portions to obtain injections (containing 2 mg of an active ingredient per vial).

TABLE 11

| Formulation | |
| --- | --- |
| Compound (IA) | 2 mg |
| hydrochloric acid | Appropriate amount |
| aqueous sodium hydroxide solution | Appropriate amount |
| distilled water for injection | Appropriate amount |
| | 2.00 mL |

Example 8

Injections having the following formulation are prepared in the same manner as in Example 7.

TABLE 12

| Formulation | |
| --- | --- |
| Compound (IB) | 2 mg |
| hydrochloric acid | Appropriate amount |
| aqueous sodium hydroxide solution | Appropriate amount |
| distilled water for injection | Appropriate amount |
| | 2.00 mL |

Example 9

Injections having the following formulation are prepared in the same manner as in Example 7.

TABLE 13

| Formulation | |
| --- | --- |
| L-DOPA | 2 mg |
| hydrochloric acid | Appropriate amount |
| aqueous sodium hydroxide solution | Appropriate amount |
| distilled water for injection | Appropriate amount |
| | 2.00 mL |

Example 10

Injections having the following formulation are prepared according to the conventional manner. Compound IA (1 g) and L-DOPA (1 g) are added to distilled water for injection followed by mixing. After adjusting the pH of the mixture to 7 by adding hydrochloric acid and a sodium hydroxide aqueous solution thereto, the total volume is adjusted to 1,000 mL with distilled water for injection. The resulting mixture is aseptically charged into glass vials in 2-mL portions to obtain injections (containing compound (IA) (2 mg) and L-DOPA (2 mg) per vial).

TABLE 14

| Formulation | |
| --- | --- |
| Compound (IA) | 2 mg |
| L-DOPA | 2 mg |

TABLE 14-continued

| Formulation | |
| --- | --- |
| hydrochloric acid | Appropriate amount |
| aqueous sodium hydroxide solution | Appropriate amount |
| distilled water for injection | Appropriate amount |
| | 2.00 mL |

Example 11

Injections having the following formulation are prepared in the same manner as in Example 10.

TABLE 15

| Formulation | |
| --- | --- |
| Compound (IC) | 2 mg |
| L-DOPA | 2 mg |
| hydrochloric acid | Appropriate amount |
| aqueous sodium hydroxide solution | Appropriate amount |
| distilled water for injection | Appropriate amount |
| | 2.00 mL |

Example 12

N-[4-(2-Furyl)-5-(tetrahydropyran-4-carbonyl)thiazol-2-yl]-6-vinylpyridine-3-carboxamide (Compound IE)

step 1 Methyl 6-chloronicotinate (1.51 g, 8.79 mmol) was dissolved in DMF (35 mL), vinyltributyltin (3.32 mL, 11.4 mmol), dichlorobis(tri-o-tolylphosphine)palladium (206 mg, 0.262 mmol) and lithium chloride (554 mg, 13.1 mmol) were added and the mixture was stirred at 100° C. for 2 hr. The mixture was allowed to cool to room temperature, and an aqueous potassium fluoride solution was added thereto. The mixture was filtered through celite and the residue was washed with ethyl acetate. To the obtained filtrate was added a saturated aqueous sodium hydrogen carbonate solution, and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=70:30) to give methyl 6-vinylnicotinate (1.22 g, 85%) as a colorless transparent oil.

$^1$H NMR (CDCl$_3$, δppm): 3.95 (s, 3H), 5.63 (dd, J=1.1, 10.8 Hz, 1H), 6.35 (dd, J=1.1, 17.4 Hz, 1H), 6.87 (dd, J=10.8, 17.4 Hz, 1H), 7.40 (d, J=8.2 Hz, 1H), 8.25 (dd, J=2.1, 8.2 Hz, 1H), 9.15-9.18 (m, 1H).

step 2 Methyl 6-vinylnicotinate (491 mg, 2.97 mmol) obtained above was dissolved in a 50% methanol aqueous solution (8 mL). Lithium hydroxide monohydrate (276 mg, 6.57 mmol) was added thereto and the mixture was stirred at room temperature for 1 hr. The mixture was cooled to 0° C., then 3 mol/L hydrochloric acid (3 mL) was added, and the precipitated solid was collected by filtration to give 6-vinylnicotinic acid (309 mg, 70%) as a white solid.

$^1$H NMR (DMSO-d$_6$, δppm): 5.61 (dd, J=1.5, 10.8 Hz, 1H), 6.37 (dd, J=1.5, 17.4 Hz, 1H), 6.89 (dd, J=10.8, 17.4 Hz, 1H), 7.62 (d, J=8.2 Hz, 1H), 8.22 (dd, J=2.2, 8.2 Hz, 1H), 9.01 (d, J=2.2 Hz, 1H), 13.35 (brs, 1H).

step 3 2-Amino-4-(2-furyl)thiazol-5-yl=tetrahydropyran-4-yl=ketone (301 mg, 1.08 mmol) described in WO2005/063743 was dissolved in DMF (1.5 mL), EDC hydrochloride (412 mg, 2.15 mmol), DMAP (66 mg, 0.54 mmol) and 6-vinylnicotinic acid (306 mg, 1.65 mmol) were added thereto, and the mixture was stirred at 50° C. for 5 hr. The mixture was allowed to cool to room temperature, water and a saturated aqueous sodium hydrogen carbonate solution were added thereto and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=50:50), and recrystallized from ethanol-water to give Compound IE (1.22 g, 85%) as white crystals.

$^1$H NMR (CDCl$_3$, δppm): 1.80-2.01 (m, 4H), 3.11-3.25 (m, 1H), 3.51 (ddd, J=3.1, 11.4, 11.4 Hz, 2H), 4.02-4.11 (m, 2H), 5.71 (dd, J=0.8, 10.7 Hz, 1H), 6.43 (dd, J=0.8, 17.5 Hz, 1H), 6.57 (dd, J=1.7, 3.8 Hz, 1H), 6.90 (dd, J=10.7, 17.5 Hz, 1H), 7.51 (d, J=8.2 Hz, 1H), 7.58 (dd, J=0.5, 1.7 Hz, 1H), 7.84 (d, J=3.8 Hz, 1H), 8.21 (dd, J=2.4, 8.2 Hz, 1H), 9.13 (d, J=2.4 Hz, 1H), 9.84 (brs, 1H). ESIMS m/z: [M+H]$^+$ 410.

Example 13

N-[4-(2-Furyl)-5-(tetrahydropyran-4-carbonyl)thiazol-2-yl]-2-(pyridin-3-yl)acetamide (Compound IF)

2-Amino-4-(2-furyl)thiazol-5-yl=tetrahydropyran-4-yl=ketone (105 mg, 0.377 mmol) described in WO2005/063743 was dissolved in DMF (2.0 mL), EDC hydrochloride (421 mg, 2.20 mmol), HOBt monohydrate (340 mg, 2.21 mmol) and 3-pyridylacetic acid hydrochloride (370 mg, 2.14 mmol) were added thereto, and the mixture was stirred at 80° C. overnight. The mixture was allowed to cool to room temperature, and water and a saturated aqueous sodium hydrogen carbonate solution were added thereto. The precipitated solid was collected by filtration, and dried under reduced pressure. The obtained solid was purified by silica gel column chromatography (hexane:ethyl acetate=50:50), and recrystallized from ethanol-water to give Compound IF (112 mg, 75%) as white crystals.

$^1$H NMR (CDCl$_3$, δppm): 1.80-2.01 (m, 4H), 3.05-3.16 (m, 1H), 3.45 (ddd, J=2.8, 11.4, 11.4 Hz, 2H), 3.81 (s, 2H), 3.97-4.06 (m, 2H), 6.54 (dd, J=1.8, 3.6 Hz, 1H), 7.32 (dd, J=7.8, 4.8 Hz, 1H), 7.52-7.54 (m, 1H), 7.62-7.68 (m, 2H), 8.55-8.64 (m, 2H), 9.21 (s, 1H). APCIMS m/z: [M+H]$^+$ 398.

Example 14

N-[4-(2-Furyl)-5-(tetrahydropyran-4-carbonyl)thiazol-2-yl]-1H-pyrrole-2-carboxamide (Compound IG)

In the same manner as in Example 13, Compound IG (86.0 mg, 65%) was obtained as pale-brown crystals from 2-amino-4-(2-furyl)thiazol-5-yl=tetrahydropyran-4-yl=ketone (100 mg, 0.360 mmol) described in WO2005/063743 and pyrrole-2-carboxylic acid (240 mg, 2.18 mmol).

$^1$H NMR (CDCl$_3$, δppm): 1.80-2.01 (m, 4H), 3.08-3.24 (m, 1H), 3.47 (ddd, J=2.7, 11.5, 11.5 Hz, 2H), 4.00-4.09 (m, 2H), 6.34-6.36 (m, 1H), 6.56 (dd, J=1.8, 3.6 Hz, 1H), 6.86-6.88 (m, 1H), 7.06-7.10 (m, 1H), 7.55-7.57 (m, 1H), 7.71 (dd, J=0.7, 3.7 Hz, 1H), 9.49 (brs, 1H), 9.65 (brs, 1H). APCIMS m/z: [M+H]$^+$ 372.

Example 15

N-[4-(2-Furyl)-5-(tetrahydropyran-4-carbonyl)thiazol-2-yl]-1H-indole-4-carboxamide (Compound IH)

In the same manner as in Example 13, Compound IH (97.6 mg, 63%) was obtained as milky white crystals from 2-amino-4-(2-furyl)thiazol-5-yl=tetrahydropyran-4-yl=ketone (102 mg, 0.367 mmol) described in WO2005/063743 and indole-4-carboxylic acid (331 mg, 2.05 mmol).

$^1$H NMR (CDCl$_3$, δppm): 1.80-2.01 (m, 4H), 3.17-3.28 (m, 1H), 3.50 (ddd, J=3.0, 11.2, 11.2 Hz, 2H), 4.02-4.11 (m, 2H), 6.58 (dd, J=1.7, 3.5 Hz, 1H), 7.23-7.36 (m, 2H), 7.43-7.48 (m, 1H), 7.58-7.60 (m, 1H), 7.67 (dd, J=4.2, 7.7 Hz, 2H), 7.76 (dd, J=0.7, 3.5 Hz, 1H), 8.46 (brs, 1H), 9.70 (brs, 1H). APCIMS m/z: [M+H]$^+$ 422.

Example 16

N-[4-(2-Furyl)-5-(tetrahydropyran-4-carbonyl)thiazol-2-yl]-2-(morpholin-4-ylmethyl)pyridine-4-carboxamide (Compound II)

step 1 2-Amino-4-(2-furyl)thiazol-5-yl=tetrahydropyran-4-yl=ketone (2.00 g, 7.19 mmol) described in WO2005/063743 was dissolved in DMF (35 mL), EDC hydrochloride (5.50 g, 28.6 mmol), HOBt monohydrate (4.40 g, 28.8 mmol) and 2-(chloromethyl)isonicotinic acid (4.93 g, 28.7 mmol) obtained by the method described in WO03/043636 were added thereto, and the mixture was stirred at 80° C. overnight. The mixture was allowed to cool to room temperature, and water and a saturated aqueous sodium hydrogen carbonate solution were added thereto. The precipitated solid was collected by filtration, and dried under reduced pressure. The obtained solid was purified by silica gel column chromatography (hexane:ethyl acetate=50:50) to give 2-(chloromethyl)-N-[4-(2-furyl)-5-(tetrahydropyran-4-carbonyl)thiazol-2-yl]pyridine-4-carboxamide (700 mg, 23%) as a pale-brown solid.

$^1$H NMR (CDCl$_3$, δppm): 1.84-1.97 (m, 4H), 3.12-3.23 (m, 1H), 3.46-3.57 (m, 2H), 4.02-4.11 (m, 2H), 4.75 (s, 2H), 6.52 (dd, J=3.6, 1.7 Hz, 1H), 7.50 (dd, J=1.7, 0.7 Hz, 1H), 7.70 (dd, J=5.1, 1.7 Hz, 1H), 7.79 (dd, J=3.6, 0.7 Hz, 1H), 7.92-7.95 (m, 1H), 8.79 (dd, J=5.1, 0.7 Hz, 1H).

step 2 2-(Chloromethyl)-N-[4-(2-furyl)-5-(tetrahydropyran-4-carbonyl)thiazol-2-yl]pyridine-4-carboxamide (70.0 mg, 0.162 mmol) obtained in step 1 was dissolved in acetonitrile (2.0 mL), then morpholine (70.0 μL, 2.15 mmol) was added thereto, and the mixture was stirred with heating under reflux for 1 hr. The mixture was allowed to cool to room temperature, water and a saturated aqueous sodium hydrogen carbonate solution were added thereto. The mixture was extracted with ethyl acetate, and the organic layer was washed with saturated brine, dried over anhydrous magnesium sulfate, and concentrated under reduced pressure. The obtained residue was purified by silica gel column chromatography (chloroform:methanol=95:5), and reslurried with hexane-ethyl acetate to give Compound II (54.6 mg, 71%) as a pale-brown solid.

$^1$H NMR (CDCl$_3$, δppm): 1.80-2.01 (m, 4H), 2.51-2.59 (m, 4H), 3.10-3.24 (m, 1H), 3.51 (ddd, J=3.0, 11.3, 11.3 Hz, 2H), 3.75-3.82 (m, 6H), 4.01-4.13 (m, 2H), 6.59 (dd, J=1.8, 3.6 Hz, 1H), 7.60 (dd, J=0.7, 1.8 Hz, 1H), 7.69 (dd, J=1.8, 5.1 Hz, 1H), 7.84 (dd, J=0.7, 3.6 Hz, 1H), 7.93-7.95 (m, 1H), 8.82 (dd, J=0.7, 5.1 Hz, 1H). ESIMS m/z: [M+H]$^+$ 483.

Example 17

N-[4-(2-Furyl)-5-(tetrahydropyran-4-carbonyl)thiazol-2-yl]-2-methoxymethylpyridine-4-carboxamide (Compound IJ)

Under ice-cooling, 60% sodium hydride (10.0 mg, 0.250 mmol) was dissolved in DMF (1.0 mL), methanol (110 μL, 2.72 mmol) was slowly added dropwise thereto, and the mixture was stirred at 0° C. for 10 min. Then, 2-(chloromethyl)-N-[4-(2-furyl)-5-(tetrahydropyran-4-carbonyl)thiazol-2-yl]pyridine-4-carboxamide (81.0 mg, 0.189 mmol) obtained in step 1 of Example 16, which was dissolved in DMF (1.0 mL), was slowly added dropwise thereto, and the mixture was stirred at room temperature for 5 hr. To the mixture were added water and a saturated aqueous sodium hydrogen carbonate solution, and the mixture was extracted with ethyl acetate. The organic layer was washed with saturated brine, dried over anhydrous magnesium sulfate, and concentrated under reduced pressure. The obtained residue was purified by silica gel column chromatography (hexane:ethyl acetate=50:50), and recrystallized from ethanol-water to give Compound IJ (45.0 mg, 56%) as white crystals.

$^1$H NMR (CDCl$_3$, δppm): 1.80-2.01 (m, 4H), 3.14-3.23 (m, 1H), 3.52 (ddd, J=3.0, 11.2, 11.2 Hz, 2H), 3.53 (s, 3H), 4.02-4.18 (m, 2H), 4.65 (s, 2H), 6.52 (dd, J=1.8, 3.6 Hz, 1H), 7.50 (d, J=1.1 Hz, 1H), 7.71 (dd, J=1.3, 5.1 Hz, 1H), 7.79 (d, J=3.6 Hz, 1H), 7.85 (s, 1H), 8.77 (d, J=5.1 Hz, 1H), 10.41 (brs, 1H). APCIMS m/z: [M+H]$^+$ 428.

Example 18

2-Ethoxymethyl-N-[4-(2-furyl)-5-(tetrahydropyran-4-carbonyl)thiazol-2-yl]pyridine-4-carboxamide (Compound IK)

In the same manner as in Example 17, Compound IK (47.0 mg, 57%) was obtained as white crystals from 2-(chloromethyl)-N-[4-(2-furyl)-5-(tetrahydropyran-4-carbonyl)thiazol-2-yl]pyridine-4-carboxamide (80.0 mg, 0.185 mmol) and ethanol (200 μL, 3.54 mmol).

$^1$H NMR (CDCl$_3$, δppm): 1.36 (t, J=7.1 Hz, 3H), 1.80-2.01 (m, 4H), 3.11-3.28 (m, 1H), 3.51 (ddd, J=3.2, 11.4, 11.4 Hz, 2H), 3.72 (q, J=7.1 Hz, 2H), 4.00-4.12 (m, 2H), 4.73 (s, 2H), 6.58 (dd, J=1.7, 3.6 Hz, 1H), 7.58 (dd, J=0.7, 1.7 Hz, 1H), 7.72 (dd, J=1.7, 5.0 Hz, 1H), 7.84 (dd, J=0.7, 3.6 Hz, 1H), 7.92 (dd, J=0.7, 1.7 Hz, 1H), 8.80 (d, J=5.0 Hz, 1H), 9.95 (brs, 1H). APCIMS m/z: [M+H]$^+$ 442.

Example 19

N-[4-(2-Furyl)-5-(tetrahydropyran-4-carbonyl)thiazol-2-yl]-2-isopropoxymethylpyridine-4-carboxamide (Compound IL)

In the same manner as in Example 17, Compound IL (30.2 mg, 36%) was obtained as white crystals from 2-(chloromethyl)-N-[4-(2-furyl)-5-(tetrahydropyran-4-carbonyl)thiazol-2-yl]pyridine-4-carboxamide (80.1 mg, 0.185 mmol) and 2-propanol (350 μL, 4.60 mmol).

$^1$H NMR (CDCl$_3$, δppm): 1.31 (d, J=6.0 Hz, 6H), 1.80-2.01 (m, 4H), 3.15-3.22 (m, 1H), 3.51 (ddd, J=2.8, 11.4, 11.4 Hz, 2H), 3.78-3.86 (qq, J=6.0, 6.0 Hz, 1H), 4.01-4.11 (m, 2H), 4.73 (s, 2H), 6.58 (dd, J=1.8, 3.6 Hz, 1H), 7.59 (dd, J=0.6, 1.8 Hz, 1H), 7.71 (dd, J=1.5, 5.1 Hz, 1H), 7.85 (dd, J=0.4, 3.5 Hz, 1H), 7.93 (d, J=0.6 Hz, 1H), 8.79 (dd, J=0.4, 5.1 Hz, 1H), 9.91 (brs, 1H). APCIMS m/z: [M+H]$^+$ 456.

Example 20

N-[4-(2-Furyl)-5-(tetrahydropyran-4-carbonyl)thiazol-2-yl]furo[2,3-b]pyridine-5-carboxamide (Compound IM)

2-Amino-4-(2-furyl)thiazol-5-yl=tetrahydropyran-4-yl=ketone (125 mg, 0.450 mmol) described in WO2005/063743 was dissolved in DMF (2.2 mL), EDC hydrochloride (173 mg, 0.900 mmol), HOBt monohydrate (138 mg, 0.900 mmol) and furo[2,3-b]pyridine-5-carboxylic acid (147 mg, 0.900 mmol) obtained in the method described in Tetrahedron Letters, vol. 35, p. 9355 (1994) were added thereto, and the mixture was stirred at 50° C. for 2 hr, then at 70° C. for 1 hr. To the mixture were added EDC hydrochloride (173 mg, 0.900 mmol), HOBt monohydrate (138 mg, 0.900 mmol) and furo[2,3-b]pyridine-5-carboxylic acid (147 mg, 0.900 mmol), and the mixture was stirred at 70° C. for 1.5 hr. The mixture was added to water-a saturated aqueous sodium hydrogen carbonate solution (1:1) and the precipitated solid was collected by filtration and dried. The obtained solid was purified by silica gel column chromatography (hexane:ethyl acetate=50:50), and recrystallized from ethanol-water to give Compound IM (81.2 mg, 43%).

$^1$H NMR (DMSO-d$_6$, δppm): 1.56-1.77 (m, 4H), 3.16-3.26 (m, 1H), 3.37-3.47 (m, 2H), 3.87-3.92 (m, 2H), 6.71 (dd, J=1.9, 3.5 Hz, 1H), 7.21 (d, J=2.4 Hz, 1H), 7.45 (dd, J=0.9, 3.5 Hz, 1H), 7.91 (dd, J=0.9, 1.9 Hz, 1H), 8.27 (d, J=2.4 Hz, 1H), 8.86 (d, J=2.4 Hz, 1H), 9.04 (d, J=2.4 Hz, 1H). ESIMS m/z: [M+H]$^+$ 424.

Example 21

N-[4-(2-Furyl)-5-(tetrahydropyran-4-carbonyl)thiazol-2-yl]-2-(pyridin-2-yl)acetamide (Compound IN)

In the same manner as in step 3 of Example 12, Compound IN (125 mg, 58%) was obtained as white crystals from 2-amino-4-(2-furyl)thiazol-5-yl=tetrahydropyran-4-yl=ketone (154 mg, 0.553 mmol) described in WO2005/063743 and 2-pyridylacetic acid hydrochloride (196 mg, 1.13 mmol).

$^1$H NMR (CDCl$_3$, δppm): 1.78-1.95 (m, 4H), 3.01-3.21 (m, 1H), 3.47 (ddd, J=2.6, 11.4, 11.4 Hz, 2H), 3.98-4.09 (m, 2H), 4.03 (s, 2H), 6.57 (dd, J=1.8, 3.6 Hz, 1H), 7.25-7.34 (m, 2H), 7.59 (dd, J=0.7, 1.8 Hz, 1H), 7.70 (dd, J=0.7, 3.5 Hz, 1H), 7.74 (ddd, J=1.8, 7.7, 7.7 Hz, 1H), 8.69-8.73 (m, 1H), 12.09 (brs, 1H). APCIMS m/z: [M+H]$^+$ 398.

Example 22

N-[4-(2-Furyl)-5-(tetrahydropyran-4-carbonyl)thiazol-2-yl]-6-methoxypyridine-3-carboxamide (Compound IO)

In the same manner as in step 3 of Example 12, Compound IO (121 mg, 54%) was obtained as white crystals from 2-amino-4-(2-furyl)thiazol-5-yl=tetrahydropyran-4-yl=ketone (150 mg, 0.539 mmol) described in WO2005/063743 and 6-methoxynicotinic acid (101 mg, 0.659 mmol).

$^1$H NMR (CDCl$_3$, δppm): 1.80-2.01 (m, 4H), 3.10-3.25 (m, 1H), 3.51 (ddd, J=2.9, 11.4, 11.4 Hz, 2H), 4.02-4.11 (m, 2H), 4.04 (s, 3H), 6.55 (dd, J=1.7, 3.5 Hz, 1H), 6.87 (d, J=8.8 Hz, 1H), 7.53-7.57 (m, 1H), 7.83 (dd, J=0.6, 3.5 Hz, 1H), 8.10 (dd, J=2.6, 8.8 Hz, 1H), 8.77 (dd, J=0.6, 2.6 Hz, 1H), 9.93 (brs, 1H). APCIMS m/z: [M+H]$^+$ 414.

Example 23

N-[4-(2-Furyl)-5-(tetrahydropyran-4-carbonyl)thiazol-2-yl]quinoline-3-carboxamide (Compound IP)

In the same manner as in step 3 of Example 12, Compound IP (178 mg, 76%) was obtained as pale-yellow crystals from 2-amino-4-(2-furyl)thiazol-5-yl=tetrahydropyran-4-yl=ketone (151 mg, 0.543 mmol) described in WO2005/063743 and quinoline-3-carboxylic acid (142 mg, 0.820 mmol).

$^1$H NMR (CDCl$_3$, δppm): 1.80-2.01 (m, 4H), 3.15-3.25 (m, 1H), 3.52 (ddd, J=2.9, 11.4, 11.4 Hz, 2H), 4.06-4.10 (m, 2H), 6.47 (dd, J=1.7, 3.5 Hz, 1H), 7.47 (dd, J=0.7, 1.6 Hz, 1H), 7.66-7.74 (m, 2H), 7.87-7.95 (m, 2H), 8.20 (dd, J=0.9, 8.4 Hz, 1H), 8.71 (d, J=1.8 Hz, 1H), 9.43 (d, J=2.4 Hz, 1H), 10.55 (s, 1H). APCIMS m/z: [M+H]$^+$ 434.

Example 24

N-[4-(2-Furyl)-5-(tetrahydropyran-4-carbonyl)thiazol-2-yl]-5,6-dimethylpyridine-3-carboxamide (Compound IQ)

step 1 5,6-Dimethylpyridine-3-carbonitrile (502 mg, 3.79 mmol) obtained by the method described in J. Heterocyclic Chem., vol. 24, p. 351 (1987) was suspended in 70% aqueous ethanol (4.5 mL), sodium hydroxide (444 mg, 11.1 mmol) was added thereto, and the mixture was stirred with heating under reflux for 3 hr. The mixture was ice-cooled to 0° C., and 6 mol/L hydrochloric acid (1.9 mL) was added thereto. The mixture was concentrated under reduced pressure and the obtained residue was suspended in chloroform-methanol. The inorganic salt was removed by filtration, and the obtained filtrate was concentrated under reduced pressure to give 5,6-dimethylpyridine-3-carboxylic acid (569 mg, 99%) as a pale-pink crude solid.

$^1$H NMR (DMSO-d$_6$, δppm): 2.23 (s, 3H), 2.39 (s, 3H), 7.83 (d, J=1.7 Hz, 1H), 8.64 (d, J=1.7 Hz, 1H).

step 2 In the same manner as in step 3 of Example 12, Compound IQ (112 mg, 49%) was obtained as white crystals from 2-amino-4-(2-furyl)thiazol-5-yl=tetrahydropyran-4-yl=ketone (151 mg, 0.550 mmol) described in WO2005/063743 and 5,6-dimethylpyridine-3-carboxylic acid (166 mg, 1.10 mmol) obtained above.

$^1$H NMR (CDCl$_3$, δppm): 1.80-2.01 (m, 4H), 2.34 (s, 3H), 2.59 (s, 3H), 3.12-3.23 (m, 1H), 3.51 (ddd, J=2.9, 11.3, 11.3 Hz, 2H), 4.04-4.09 (m, 2H), 6.49 (dd, J=2.0, 3.6 Hz, 1H), 7.47 (d, J=1.7 Hz, 1H), 7.79 (dd, J=0.5, 3.5 Hz, 1H), 7.89 (d, J=1.7 Hz, 1H), 8.86 (d, J=2.0 Hz, 1H). ESIMS m/z: [M+H]$^+$ 412.

Example 25

5-Ethyl-N-[4-(2-furyl)-5-(tetrahydropyran-4-carbonyl)thiazol-2-yl]pyridine-3-carboxamide (Compound IR)

In the same manner as in step 3 of Example 12, Compound IR (145 mg, 65%) was obtained as white crystals from 2-amino-4-(2-furyl)thiazol-5-yl=tetrahydropyran-4-yl=ketone (151 mg, 0.543 mmol) described in WO2005/063743 and 5-ethylnicotinic acid (128 mg, 0.814 mmol).

$^1$H NMR (CDCl$_3$, δppm): 1.32 (t, J=7.6 Hz, 3H), 1.83-2.01 (m, 4H), 2.77 (q, J=7.6 Hz, 2H), 3.11-3.26 (m, 1H), 3.51 (ddd, J=2.9, 11.4, 11.4 Hz, 2H), 4.01-4.11 (m, 2H), 6.54 (dd, J=1.8, 3.6 Hz, 1H), 7.51-7.53 (m, 1H), 7.80 (dd, J=0.7, 3.6 Hz, 1H), 8.03-8.06 (m, 1H), 8.70 (d, J=2.0 Hz, 1H), 8.99 (d, J=2.0 Hz, 1H), 10.24 (brs, 1H). ESIMS m/z: [M+H]$^+$ 412.

Example 26

N-[4-(2-Furyl)-5-(tetrahydropyran-4-carbonyl)thiazol-2-yl]-7,8-dihydro-5H-pyrano[4,3-b]pyridine-3-carboxamide (Compound IS)

step 1 Sodium hydride (2.06 g, 51.5 mmol) was suspended in diethyl ether (40 mL), and methanol (2.1 mL, 51.8 mmol) was added slowly at −5° C. thereto. To the mixture was added ethanol (6 mL), and the mixture was stirred at room temperature for 5 min, and cooled to 0° C. A mixture of tetrahydro-4H-pyran-4-one (4.61 mL, 49.9 mmol) and ethyl formate (4.11 mL, 51.1 mmol) was slowly added thereto. The mixture was stirred at room temperature for 2 hr, and the resultant product was extracted with water (30 mL) (aqueous solution A).

Then, an aqueous piperidine-acetic acid solution prepared by dissolving acetic acid (1.5 mL) in water (3.5 mL) and adding piperidine (2.6 mL) thereto, and 2-cyanoacetamide (4.62 g, 54.9 mmol) were added to the above-mentioned aqueous solution A, and the mixture was stirred with heating under reflux for 4 hr. To the mixture was added acetic acid (3.6 mL) and, after cooling 0° C., the precipitated solid was collected by filtration to give 2-oxo-1,5,7,8-tetrahydro-2H-pyrano[4,3-b]pyridine-3-carbonitrile (1.72 g, 20%) as a white solid.

$^1$H NMR (CDCl$_3$, δppm): 2.89 (t, J=5.6 Hz, 2H), 3.99 (t, J=5.6 Hz, 2H), 4.54 (s, 2H), 7.59 (s, 1H). APCIMS m/z: [M−H]$^-$ 175.

step 2 2-Oxo-1,5,7,8-tetrahydro-2H-pyrano[4,3-b]pyridine-3-carbonitrile (2.50 g, 14.4 mmol) obtained in step 1 was dissolved in phosphoryl chloride (20 mL), and the mixture was stirred with heating under reflux for 4 hr. The mixture was allowed to cool to room temperature, and slowly added to a saturated aqueous sodium hydrogen carbonate solution at 0° C., then the mixture was extracted with chloroform. The organic layer was washed with saturated brine, dried over anhydrous magnesium sulfate, and concentrated under reduced pressure. The obtained residue was purified by silica gel column chromatography (hexane: ethyl acetate=50:50) to give 2-chloro-7,8-dihydro-5H-pyrano[4,3-b]pyridine-3-carbonitrile (1.85 g, 66%) as a white solid.

$^1$H NMR (CDCl$_3$, δppm): 3.07 (t, J=5.8 Hz, 2H), 4.07 (t, J=5.8 Hz, 2H), 4.75-4.76 (m, 2H), 7.63 (s, 1H).

step 3 2-Chloro-7,8-dihydro-5H-pyrano[4,3-b]pyridine-3-carbonitrile (1.77 g, 9.09 mmol) obtained in step 2 was dissolved in ethanol (30 mL), acetic acid (9 mL) and zinc (2.60 g) were added thereto, and the mixture was stirred with heating under reflux for 4 hr. The mixture was allowed to cool to room temperature, then filtered through celite, and the filtrate was concentrated under reduced pressure. To the obtained residue was added a saturated aqueous sodium hydrogen carbonate solution and the mixture was extracted with chloroform. The organic layer was washed with saturated brine, dried over anhydrous magnesium sulfate, and concentrated under reduced pressure. The obtained residue was purified by silica gel column chromatography (hexane: ethyl acetate=50:50) to give 7,8-dihydro-5H-pyrano[4,3-b]pyridine-3-carbonitrile (1.06 g, 73%) as a white solid.

$^1$H NMR (CDCl$_3$, δppm): 3.10 (t, J=5.8 Hz, 2H), 4.10 (t, J=5.8 Hz, 2H), 4.79 (s, 2H), 7.59 (d, J=1.7 Hz, 1H), 8.71 (d, J=1.7 Hz, 1H). APCIMS m/z: [M+H]$^+$ 161.

step 4 In the same manner as in step 1 of Example 24, 7,8-dihydro-5H-pyrano[4,3-b]pyridine-3-carboxylic acid (318 mg, 47%) was obtained as a white solid from 7,8-dihydro-5H-pyrano[4,3-b]pyridine-3-carbonitrile (609 mg, 3.80 mmol) obtained above.

$^1$H NMR (DMSO-$d_6$, δppm): 2.86 (t, J=5.8 Hz, 2H), 3.95 (t, J=5.8 Hz, 2H), 4.70 (s, 2H), 7.80 (d, J=1.7 Hz, 1H), 8.76 (d, J=1.7 Hz, 1H). ESIMS m/z: [M−H]$^−$ 178.

step 5 In the same manner as in step 3 of Example 12, Compound IS (178 mg, 74%) was obtained as white crystals from 2-amino-4-(2-furyl)thiazol-5-yl=tetrahydropyran-4-yl=ketone (152 mg, 0.546 mmol) described in WO2005/063743 and 7,8-dihydro-5H-pyrano[4,3-b]pyridine-3-carboxylic acid (432 mg, 2.00 mmol) obtained above.

$^1$H NMR (CDCl$_3$, δppm): 1.80-2.01 (m, 4H), 3.10 (t, J=5.6 Hz, 2H), 3.13-3.24 (m, 1H), 3.51 (ddd, J=2.8, 11.4, 11.4 Hz, 2H), 4.03-4.14 (m, 4H), 4.79 (s, 2H), 6.50 (dd, J=1.7, 3.6 Hz, 1H), 7.46 (dd, J=0.6, 1.7 Hz, 1H), 7.78 (dd, J=0.6, 3.6 Hz, 1H), 7.82 (d, J=2.2 Hz, 1H), 8.94 (d, J=2.2 Hz, 1H), 10.58 (s, 1H). ESIMS m/z: [M+H]$^+$ 440.

Example 27

N-[4-(2-Furyl)-5-(tetrahydropyran-4-carbonyl)thiazol-2-yl]-6,7-dihydro-5H-cyclopenta[b]pyridine-3-carboxamide (Compound IT)

step 1 6,7-Dihydro-5H-cyclopenta[b]pyridine-3-carbonitrile (901 mg, 6.25 mmol) obtained by the method described in J. Heterocyclic Chem., vol. 24, p. 351 (1987) was suspended in 6 mol/L hydrochloric acid (9 mL), and the mixture was stirred with heating under reflux for 5 hr. The mixture was ice-cooled to 0° C., and the precipitated solid was collected by filtration to give 6,7-dihydro-5H-cyclopenta[b]pyridine-3-carboxylic acid hydrochloride (543 mg, 44%) as a pale-brown solid.

$^1$H NMR (DMSO-$d_6$, δppm): 2.16 (tt, J=7.4, 7.8 Hz, 2H), 3.02 (t, J=7.4 Hz, 2H), 3.10 (t, J=7.8 Hz, 2H), 8.34 (s, 1H), 8.92 (s, 1H).

step 2 In the same manner as in step 3 of Example 12, Compound IT (134 mg, 58%) was obtained as white crystals from 2-amino-4-(2-furyl)thiazol-5-yl=tetrahydropyran-4-yl=ketone (152 mg, 0.546 mmol) described in WO2005/063743 and 6,7-dihydro-5H-cyclopenta[b]pyridine-3-carboxylic acid hydrochloride (165 mg, 0.827 mmol) obtained above.

$^1$H NMR (CDCl$_3$, δppm): 1.78-2.01 (m, 4H), 2.16-2.28 (m, 2H), 3.01 (t, J=7.6 Hz, 2H), 3.10 (t, J=7.7 Hz, 2H), 3.11-3.25 (m, 1H), 3.51 (ddd, J=3.0, 11.4, 11.4 Hz, 2H), 4.00-4.10 (m, 2H), 6.52 (dd, J=1.8, 3.6 Hz, 1H), 7.51 (dd, J=0.7, 1.7 Hz, 1H), 7.80 (dd, J=0.7, 3.6 Hz, 1H), 7.95-8.00 (m, 1H), 8.87-8.91 (m, 1H), 10.20 (brs, 1H). ESIMS m/z: [M+H]$^+$ 424.

Example 28

N-[4-(2-Furyl)-5-(tetrahydropyran-4-carbonyl)thiazol-2-yl]-1H-indole-2-carboxamide (Compound IU)

In the same manner as in Example 13, Compound IU (97.5 mg, 63%) was obtained as pale-brown crystals from 2-amino-4-(2-furyl)thiazol-5-yl=tetrahydropyran-4-yl=ketone (102 mg, 0.366 mmol) described in WO2005/063743 and indole-2-carboxylic acid (350 mg, 2.17 mmol).

$^1$H NMR (CDCl$_3$, δppm): 1.80-2.01 (m, 4H), 3.10-3.24 (m, 1H), 3.50 (ddd, J=2.7, 11.5, 11.5 Hz, 2H), 4.01-4.11 (m, 2H), 6.59 (dd, J=1.7, 3.5 Hz, 1H), 7.14 (dd, J=0.9, 2.2 Hz, 1H), 7.19-7.25 (m, 1H), 7.36-7.43 (m, 1H), 7.46-7.52 (m, 1H), 7.60 (dd, J=0.7, 1.7 Hz, 1H), 7.72-7.77 (m, 1H), 7.83 (dd, J=0.7, 3.5 Hz, 1H), 9.21 (brs, 1H), 9.66 (brs, 1H). APCIMS m/z: [M+H]$^+$ 422.

Example 29

6-Ethyl-N-[4-(2-furyl)-5-(tetrahydropyran-4-carbonyl)thiazol-2-yl]pyridine-3-carboxamide (Compound IV)

Compound IE (90.0 mg, 0.220 mmol) obtained in Example 12 was dissolved in ethanol (10 mL) under an argon atmosphere, 10% palladium carbon (10%-Pd/C; containing water) (88.9 mg) was added thereto, and mixture was stirred at room temperature overnight under a hydrogen atmosphere. The mixture was filtered through celite, and the filtrate was concentrated under reduced pressure. The obtained residue was purified by preparative thin layer chromatography (hexane:ethyl acetate=30:70), and recrystallized from ethanol-water to give Compound IV (70.0 mg, 77%) as white crystals.

$^1$H NMR (CDCl$_3$, δppm): 1.36 (t, J=7.6 Hz, 3H), 1.80-2.01 (m, 4H), 2.94 (q, J=7.6 Hz, 2H), 3.11-3.27 (m, 1H), 3.51 (ddd, J=3.0, 11.3, 11.3 Hz, 2H), 3.99-4.13 (m, 2H), 6.54 (dd, J=1.7, 3.5 Hz, 1H), 7.35 (d, J=8.1 Hz, 1H), 7.52 (dd, J=0.7, 1.7 Hz, 1H), 7.81 (dd, J=0.7, 3.6 Hz, 1H), 8.15 (dd, J=2.2, 8.2 Hz, 1H), 9.08 (d, J=2.2 Hz, 1H), 10.13 (brs, 1H). ESIMS m/z: [M+H]$^+$ 412.

Example 30

N-[4-(2-Furyl)-5-(tetrahydropyran-4-carbonyl)thiazol-2-yl]-6-propylpyridine-3-carboxamide (Compound IW)

step 1 In the same manner as in step 1 of Example 12, methyl 6-(1-propenyl)nicotinate (327 mg, 37%) was obtained as a colorless transparent oil from methyl 6-chloronicotinate (862 mg, 6.48 mmol) and allyltributyltin (2.20 mL, 7.09 mmol).

$^1$H NMR (CDCl$_3$, δppm): 1.97 (dd, J=1.7, 6.8 Hz, 3H), 3.95 (s, 3H), 6.55 (dq, J=1.7, 15.7 Hz, 1H), 6.92 (dq, J=6.8, 15.7 Hz, 1H), 7.25-7.30 (m, 1H), 8.19 (dd, J=2.2, 8.2 Hz, 1H), 9.11 (dd, J=0.5, 2.2 Hz, 1H).

step 2 In the same manner as in step 2 of Example 12, 6-(1-propenyl)nicotinic acid (251 mg, 84%) was obtained as milk-white crystals from methyl 6-(1-propenyl)nicotinate (326 mg, 1.84 mmol) obtained above.

$^1$H NMR (DMSO-$d_6$, δppm): 1.91 (dd, J=1.8, 6.8 Hz, 3H), 6.58 (dq, J=1.8, 15.5 Hz, 1H), 6.91 (dq, J=6.8, 15.5 Hz, 1H), 7.48 (dd, J=0.5, 8.3 Hz, 1H), 8.15 (dd, J=2.2, 8.3 Hz, 1H), 8.95 (dd, J=0.5, 2.2 Hz, 1H), 13.24 (brs, 1H). ESIMS m/z: [M+H]$^+$ 164.

step 3 In the same manner as in step 3 of Example 12, N-[4-(2-furyl)-5-(tetrahydropyran-4-carbonyl)thiazol-2-yl]-6-(1-propenyl)pyridine-3-carboxamide (125 mg, 33%) was obtained as white crystals from 2-amino-4-(2-furyl)thiazol-5-yl=tetrahydropyran-4-yl=ketone (257 mg, 0.908 mmol) described in WO2005/063743 and 6-(1-propenyl)nicotinic acid (251 mg, 1.26 mmol) obtained above.

$^1$H NMR (CDCl$_3$, δppm): 1.82-1.96 (m, 4H), 2.01 (dd, J=1.4, 6.8 Hz, 3H), 3.12-3.23 (m, 1H), 3.52 (ddd, J=3.0, 11.2, 11.2 Hz, 2H), 4.02-4.11 (m, 2H), 6.54-6.62 (m, 2H), 7.00 (dq, J=6.8, 15.5 Hz, 1H), 7.37 (d, J=8.4 Hz, 1H), 7.55 (dd, J=0.8, 1.6 Hz, 1H), 7.82 (d, J=3.6 Hz, 1H), 8.15 (dd, J=2.4, 8.3 Hz, 1H), 9.08 (d, J=2.4 Hz, 1H), 10.00 (brs, 1H). ESIMS m/z: [M+H]$^+$ 424.

step 4 In the same manner as in Example 29, the title Compound IW (96.0 mg, 76%) was obtained as white crystals from N-[4-(2-furyl)-5-(tetrahydropyran-4-carbonyl)thiazol-2-yl]-6-(1-propenyl)pyridine-3-carboxamide (125 mg, 0.296 mmol) obtained above.

$^1$H NMR (CDCl$_3$, δppm): 1.00 (t, J=7.3 Hz, 3H), 1.75-1.97 (m, 6H), 2.88 (t, J=7.6 Hz, 2H), 3.13-3.24 (m, 1H), 3.51 (ddd, J=3.1, 11.4, 11.4 Hz, 2H), 4.02-4.11 (m, 2H), 6.55 (dd, J=1.8, 3.6 Hz, 1H), 7.33 (d, J=8.2 Hz, 1H), 7.53-7.55 (m, 1H), 7.81 (d, J=3.6 Hz, 1H), 8.15 (dd, J=2.5, 8.2 Hz, 1H), 9.09 (d, J=2.1 Hz, 1H), 10.14 (s, 1H). ESIMS m/z: [M+H]$^+$ 426.

Example 31

N-[4-(2-Furyl)-5-(tetrahydropyran-4-carbonyl)thiazol-2-yl]-7,8-dihydro-5H-thiopyrano[4,3-b]pyridine-3-carboxamide (Compound IX)

step 1 In the same manner as in step 1 of Example 26, 2-oxo-1,5,7,8-tetrahydro-5H-thiopyrano[4,3-b]pyridine-3-carbonitrile (3.06 g, 37%) was obtained as a pale-yellow solid from tetrahydro-4H-thiopyran-4-one (5.00 g, 43.0 mmol).

$^1$H NMR (CDCl$_3$, δppm): 2.93 (t, J=6.0 Hz, 2H), 3.11 (t, J=6.0 Hz, 2H), 3.58 (s, 2H), 7.67 (s, 1H), 13.4 (brs, 1H).

step 2 In the same manner as in step 2 of Example 26, 2-chloro-7,8-dihydro-5H-thiopyrano[4,3-b]pyridine-3-carbonitrile (1.75 g, 58%) was obtained from 2-oxo-1,5,7,8-tetrahydro-5H-thiopyrano[4,3-b]pyridine-3-carbonitrile (2.78 g, 14.4 mmol) obtained above.

$^1$H NMR (CDCl$_3$, δppm): 3.01 (t, J=6.1 Hz, 2H), 3.27 (t, J=6.1 Hz, 2H), 3.78 (s, 2H), 7.71 (s, 1H).

step 3 In the same manner as in step 3 of Example 26, 7,8-dihydro-5H-thiopyrano[4,3-b]pyridine-3-carbonitrile (804 mg, 55%) was obtained from 2-chloro-7,8-dihydro-5H-thiopyrano[4,3-b]pyridine-3-carbonitrile (1.75 g, 8.31 mmol) obtained above.

$^1$H NMR (CDCl$_3$, δppm): 3.04 (t, J=6.2 Hz, 2H), 3.30 (t, J=6.2 Hz, 2H), 3.81 (s, 2H), 7.68 (d, J=2.0 Hz, 1H), 8.69 (d, J=2.0 Hz, 1H).

step 4 In the same manner as in step 1 of Example 27, 7,8-dihydro-5H-thiopyrano[4,3-b]pyridine-3-carboxylic acid hydrochloride (901 mg, 78%) was obtained from 7,8-dihydro-5H-thiopyrano[4,3-b]pyridine-3-carbonitrile (874 mg, 4.96 mmol) obtained above.

$^1$H NMR (DMSO-d$_6$, δppm): 3.01 (t, J=6.2 Hz, 2H), 3.24 (t, J=6.2 Hz, 2H), 3.96 (s, 2H), 8.27-8.36 (m, 1H), 8.92 (d, J=1.8 Hz, 1H). ESIMS m/z: [M−H]$^−$ 194.

step 5 In the same manner as in step 3 of Example 12, Compound IX (79.0 mg, 68%) was obtained as pale-brown crystals from 2-amino-4-(2-furyl)thiazol-5-yl=tetrahydropyran-4-yl=ketone (70.7 mg, 0.254 mmol) described in WO2005/063743 and 7,8-dihydro-5H-thiopyrano[4,3-b]pyridine-3-carboxylic acid hydrochloride (90.9 mg, 0.392 mmol) obtained above.

$^1$H NMR (CDCl$_3$, δppm): 1.81-2.01 (m, 4H), 3.05 (t, J=6.2 Hz, 2H), 3.15-3.22 (m, 1H), 3.33 (t, J=6.0 Hz, 2H), 3.51 (ddd, J=2.9, 11.4, 11.4 Hz, 2H), 3.83 (s, 2H), 4.03-4.10 (m, 2H), 6.53 (dd, J=1.8, 3.5 Hz, 1H), 7.51 (d, J=0.7, 1.8 Hz, 1H), 7.81 (dd, J=0.7, 3.5 Hz, 1H), 7.94-7.96 (m, 1H), 8.95 (d, J=2.2 Hz, 1H). ESIMS m/z: [M+H]$^+$ 456.

Example 32

5-Acetyl-N-[4-(2-furyl)-5-(tetrahydropyran-4-carbonyl)thiazol-2-yl]-6-methylpyridine-3-carboxamide (Compound IY)

step 1 In the same manner as in step 2 of Example 12, 5-acetyl-6-methylpyridine-3-carboxylic acid (462 mg, quantitative) was obtained as a yellow solid from ethyl 5-acetyl-6-methylpyridine-3-carboxylate (561 mg, 2.71 mmol) obtained by the method described in Synthesis, vol. 5, p. 400 (1986).

$^1$H NMR (DMSO-d$_6$, δppm): 2.63 (s, 3H), 2.66 (s, 3H), 8.54 (d, =2.0 Hz, 1H), 9.01 (d, J=2.0 Hz, 1H).

step 2 2-Amino-4-(2-furyl)thiazol-5-yl=tetrahydropyran-4-yl=ketone (71.2 mg, 0.256 mmol) described in WO2005/063743 was dissolved in DMF (0.5 mL), (benzotriazol-1-yloxy)tripyrrolidinophosphonium hexafluorophosphate (PyBOP) (262 mg, 0.510 mmol), diisopropylethylamine (DIPEA) (150 μL, 0.860 mmol) and 5-acetyl-6-methylpyridine-3-carboxylic acid (93.2 mg, 0.520 mmol) obtained above were added thereto, and the mixture was stirred at 80° C. overnight. The mixture was allowed to cool to room temperature, water and a saturated aqueous sodium hydrogen carbonate solution were added thereto and the mixture was extracted with ethyl acetate. The organic layer was washed with saturated brine, and dried over anhydrous magnesium sulfate. The solvent was evaporated under reduced pressure and the obtained residue was purified by silica gel column chromatography (hexane:ethyl acetate=50:50), and reslurried with ethanol-water to give Compound IY (87.4 mg, 77%) as a pale-yellow solid.

$^1$H NMR (CDCl$_3$, δppm): 1.81-2.01 (m, 4H), 2.67 (s, 3H), 2.86 (s, 3H), 3.13-3.23 (m, 1H), 3.51 (ddd, J=2.9, 11.4, 11.4 Hz, 2H), 4.03-4.10 (m, 2H), 6.56 (dd, J=1.7, 3.5 Hz, 1H), 7.55 (dd, J=0.6, 1.7 Hz, 1H), 7.82 (d, J=0.6, 3.5 Hz, 1H), 8.54 (d, J=2.4 Hz, 1H), 9.11 (d, J=2.4 Hz, 1H). ESIMS m/z: [M+H]$^+$ 440.

Example 33

5-Ethyl-N-[4-(3-furyl)-5-(tetrahydropyran-4-carbonyl)thiazol-2-yl]pyridine-3-carboxamide (Compound IZ)

In the same manner as in step 3 of Example 12, Compound IZ (177 mg, 79%) was obtained as white crystals from 2-amino-4-(3-furyl)thiazol-5-yl=tetrahydropyran-4-yl=ketone (151 mg, 0.541 mmol) obtained by the method described in WO2005/063743 and 5-ethylnicotinic acid (249 mg, 1.64 mmol).

$^1$H NMR (CDCl$_3$, δppm): 1.34 (t, J=7.6 Hz, 3H), 1.80-2.01 (m, 4H), 2.80 (q, J=7.6 Hz, 2H), 3.11-3.18 (m, 1H), 3.51 (ddd, J=2.8, 11.4, 11.4 Hz, 2H), 4.01-4.10 (m, 2H), 7.01 (dd, J=0.7, 1.8 Hz, 1H), 7.45-7.48 (m, 1H), 8.10-8.13 (m, 1H), 8.63 (dd, J=0.7, 1.5 Hz, 1H), 8.71-8.76 (m, 1H), 9.02-9.05 (m, 1H). ESIMS m/z: [M+H]$^+$ 412.

Example 34

N-[4-(3-Furyl)-5-(tetrahydropyran-4-carbonyl)thiazol-2-yl]-6,7-dihydro-5H-cyclopenta[b]pyridine-3-carboxamide (Compound IAA)

In the same manner as in step 3 of Example 12, Compound IAA (71.1 mg, 39%) was obtained as white crystals from 2-amino-4-(3-furyl)thiazol-5-yl=tetrahydropyran-4-yl=ketone (120 mg, 0.432 mmol) and 6,7-dihydro-5H-cyclopenta[b]pyridine-3-carboxylic acid hydrochloride (172 mg, 0.870 mmol).

$^1$H NMR (CDCl$_3$, δppm): 1.80-2.01 (m, 4H), 2.18-2.30 (m, 2H), 3.03-3.20 (m, 5H), 3.52 (ddd, J=2.9, 11.3, 11.3 Hz, 2H), 4.01-4.10 (m, 2H), 7.03 (dd, J=0.6, 2.0 Hz, 1H), 7.48 (dd, J=1.7, 1.7 Hz, 1H), 8.08-8.10 (m, 1H), 8.68-8.70 (m, 1H), 8.95-8.97 (m, 1H). ESIMS m/z: [M+H]$^+$ 424.

Reference Example 1

Compounds (IA)-(ID) were obtained according to the method described in WO2005/063743.

INDUSTRIAL APPLICABILITY

The present invention can be utilized for the treatment and/or prophylaxis of, for example, movement disorders (specifically, for example, extrapyramidal syndrome, side effects of L-DOPA and/or dopamine agonist therapy and the like), or the treatment and/or prophylaxis of Parkinson's disease.

EXPLANATION OF SYMBOLS

○ combination of solvent and L-DOPA
● combination of compound (IC) and L-DOPA

The invention claimed is:

1. A method of treating and/or preventing progression of a motor complication caused by L-DOPA and/or dopamine agonist therapy, comprising the steps of:
administering to a patient undergoing L-DOPA and/or dopamine agonist therapy an effective amount of a thiazole derivative represented by formula (IC)

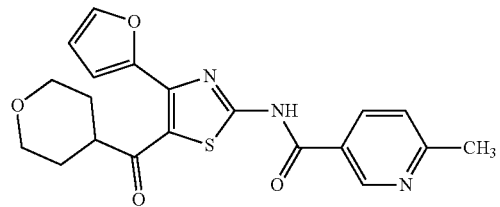

or a pharmaceutically acceptable salt thereof.

2. The method according to claim 1, wherein the motor complication is wearing-off phenomenon.

3. The method according to claim 1, wherein the motor complication is on-off fluctuation.

4. The method according to claim 1, wherein said motor complication is caused by L-DOPA therapy and said patient is undergoing L-DOPA therapy.

5. The method according to claim 1, wherein said motor complication is caused by dopamine agonist therapy and said patient is undergoing dopamine agonist therapy.

6. The method according to claim 2, wherein said motor complication is caused by L-DOPA therapy and said patient is undergoing L-DOPA therapy.

7. The method according to claim 2, wherein said motor complication is caused by dopamine agonist therapy and said patient is undergoing dopamine agonist therapy.

8. The method according to claim 3, wherein said motor complication is caused by L-DOPA therapy and said patient is undergoing L-DOPA therapy.

9. The method according to claim 3, wherein said motor complication is caused by dopamine agonist therapy and said patient is undergoing dopamine agonist therapy.

* * * * *